(12) United States Patent
Emery et al.

(10) Patent No.: US 7,943,150 B2
(45) Date of Patent: *May 17, 2011

(54) IMMUNIZING COMPOSITIONS AND METHODS OF USE

(75) Inventors: Daryll A. Emery, New London, MN (US); Darren E. Straub, New London, MN (US)

(73) Assignee: Epitopix, LLC, Willmar, MN (US)

( * ) Notice: Subject to any disclaimer, the term of this patent is extended or adjusted under 35 U.S.C. 154(b) by 34 days.

This patent is subject to a terminal disclaimer.

(21) Appl. No.: 12/101,802

(22) Filed: Apr. 11, 2008

(65) Prior Publication Data

US 2009/0081236 A1 Mar. 26, 2009

Related U.S. Application Data

(60) Continuation of application No. 11/386,393, filed on Mar. 22, 2006, now Pat. No. 7,371,393, which is a division of application No. 10/454,305, filed on Jun. 3, 2003, now Pat. No. 7,138,124, which is a division of application No. 10/038,504, filed on Jan. 3, 2002, now abandoned.

(60) Provisional application No. 60/259,504, filed on Jan. 3, 2001, provisional application No. 60/262,896, filed on Jan. 19, 2001.

(51) Int. Cl.
| | |
|---|---|
| A61K 39/02 | (2006.01) |
| A61K 39/108 | (2006.01) |
| A61K 39/102 | (2006.01) |
| A61K 39/112 | (2006.01) |
| A61K 39/106 | (2006.01) |

(52) U.S. Cl. ............... 424/234.1; 424/184.1; 424/236.1; 424/241.1; 424/255.1; 424/256.1; 424/257.1; 424/258.1; 424/260.1; 424/261.1

(58) Field of Classification Search .................. None
See application file for complete search history.

(56) References Cited

U.S. PATENT DOCUMENTS

| | | |
|---|---|---|
| 4,167,560 A | 9/1979 | Wohler, Jr. |
| 4,452,775 A | 6/1984 | Kent |
| 4,626,416 A | 12/1986 | DeVoe et al. |
| 4,663,161 A | 5/1987 | Mannino et al. |
| 4,681,761 A | 7/1987 | Mietzner et al. |
| 4,748,018 A | 5/1988 | Stolle et al. |
| 4,871,488 A | 10/1989 | Mannino et al. |
| 4,981,685 A | 1/1991 | Healey |
| 5,141,743 A | 8/1992 | Schryvers |
| 5,292,869 A | 3/1994 | Schryvers |
| 5,439,808 A | 8/1995 | Blake et al. |
| 5,534,256 A | 7/1996 | Potter et al. |
| 5,538,733 A | 7/1996 | Emery et al. |
| 5,587,166 A | 12/1996 | Donachie |
| 5,688,682 A | 11/1997 | Mulks et al. |
| 5,830,479 A | 11/1998 | Emery et al. |
| 5,885,589 A | 3/1999 | Foged et al. |
| 5,906,826 A | 5/1999 | Emery et al. |
| 6,027,736 A | 2/2000 | Emery et al. |
| 6,348,198 B1 | 2/2002 | Schryvers et al. |
| 6,432,412 B1 | 8/2002 | Emery et al. |
| 6,682,754 B2 | 1/2004 | Emery et al. |
| 6,692,739 B1 | 2/2004 | Patti et al. |
| 6,720,160 B2 | 4/2004 | Wolde-Mariam |
| 6,869,607 B1 | 3/2005 | Buschle et al. |
| 6,984,503 B1 | 1/2006 | Wang et al. |
| 7,026,157 B1 | 4/2006 | Stojiljkovic et al. |
| 7,138,124 B2 | 11/2006 | Emery et al. |
| 7,138,125 B2 | 11/2006 | Emery et al. |
| 7,147,857 B2 | 12/2006 | Emery et al. |
| 7,148,191 B2 | 12/2006 | Egyed et al. |
| 7,153,527 B2 | 12/2006 | Gradle et al. |
| 7,160,549 B2 | 1/2007 | Emery et al. |
| 7,341,732 B2 * | 3/2008 | Emery et al. ................ 424/234.1 |
| 7,371,393 B2 * | 5/2008 | Emery et al. ................ 424/234.1 |
| 7,413,743 B2 * | 8/2008 | Emery et al. ................ 424/255.1 |
| 2003/0036639 A1 | 2/2003 | Emery et al. |
| 2003/0064073 A1 | 4/2003 | Emery et al. |
| 2003/0206922 A1 | 11/2003 | Emery et al. |
| 2003/0211118 A1 | 11/2003 | Emery et al. |
| 2004/0197350 A1 | 10/2004 | Emery et al. |
| 2004/0197869 A1 | 10/2004 | Emery et al. |
| 2004/0265329 A1 | 12/2004 | Emery et al. |
| 2005/0095682 A1 | 8/2005 | Emery et al. |
| 2005/0186217 A1 | 8/2005 | Emery et al. |
| 2006/0024323 A1 | 2/2006 | Emery et al. |
| 2006/0083753 A1 | 4/2006 | Emery et al. |
| 2006/0165718 A1 | 7/2006 | Emery et al. |
| 2006/0233824 A1 | 10/2006 | Emery et al. |
| 2006/0269564 A1 | 11/2006 | Emery et al. |
| 2007/0087011 A1 | 4/2007 | Emery et al. |
| 2007/0098733 A1 | 5/2007 | Emery et al. |
| 2008/0200650 A1 | 8/2008 | Emery et al. |
| 2008/0293080 A1 * | 11/2008 | Emery et al. ................ 435/7.37 |
| 2009/0081236 A1 * | 3/2009 | Emery et al. ................ 424/165.1 |
| 2009/0162402 A1 * | 6/2009 | Emery et al. ................ 424/257.1 |

FOREIGN PATENT DOCUMENTS

| | | |
|---|---|---|
| CA | 2029906 | 9/1990 |
| EP | 0 287 206 A1 | 10/1988 |
| EP | 0 287 206 B1 | 8/1993 |
| EP | 0 287 206 B2 | 8/1993 |
| WO | WO 90/11349 A1 | 10/1990 |
| WO | WO 90/12591 A1 | 11/1990 |
| WO | WO 95/21627 A1 | 8/1995 |
| WO | WO 96/01620 A1 | 1/1996 |

OTHER PUBLICATIONS

U.S. Appl. No. 12/269,636, filed Nov. 12, 2008, Emery et al.

(Continued)

*Primary Examiner* — N. M Minnifield
(74) *Attorney, Agent, or Firm* — Mueting, Raasch & Gebhardt, P.A.

(57) ABSTRACT

The present invention provides compositions including siderophore receptor polypeptides and porins from gram negative microbes, and preferably, lipopolysaccharide at a concentration of no greater than about 10.0 endotoxin units per milliliter. The present invention also provides methods of making and methods of using such compositions, including inducing the production of antibody in an animal.

70 Claims, 10 Drawing Sheets

OTHER PUBLICATIONS

U.S. Appl. No. 12/272,021, filed Nov. 17, 2008, Emery et al.
U.S. Appl. No. 12/347,332, filed Dec. 31, 2008, Emery et al.
U.S. Appl. No. 12/393,275, filed Feb. 26, 2009, Emery et al.
International Preliminary Examination report from related International Application No. PCT/US02/00188, 5 pages. Sep. 27, 2004.
Non-Final Office Action from related U.S. Appl. No. 12/393,275, dated Dec. 28, 2009, 6 pgs.
U.S. Appl. No. 11/518,689, filed Sep. 11, 2006, Emery et al.
Acheson et al., "Protective Immunity to Shiga-Like Toxin I Following Oral Immunization with Shiga-Like Toxin I B-Subunit-Producing *Vibrio cholerae* CVD 103-HgR," *Infect. Immun.*, Jan. 1996;64(1):355-357.
Alberti et al., "A porin from *Klebsiella pneumoniae*: sequence homology, three-dimensional model, and complement binding," *Infect Immun.* Mar. 1995;63(3): 903-910.
Alurkar et al., "Immunomodulatory Properties of Porins of Some Members of the family Enterobacteriaceae," *Infection and Immunity*, Jun. 1997; 65(6):2382-2388.
Ames, "Resolution of bacterial proteins by polyacrylamide gel electrophoresis on slabs. Membrane, soluble, and periplasmic fractions," *J Biol Chem.* Jan. 25, 1974; 249(2):634-644. (No abstract available.).
Anwar et al., "Antibody response to acute *Pseudomonas aeruginosa* infection in a burn wound," *FEMS Microbiology Letters*, 1985; 29:225-230.
Arockiasamy et al., "Purification of Integral Outer-Membrane Protein OmpC, a Surface Antigen from *Salmonella typhi* for Structure-Function Studies: A Method Applicable to Enterobacterial Major Outer-Membrane Protein," *Analytical Biochemistry*, 2000, 283:64-70.
Arp, "Response of turkeys to *Escherichia coli*," *Poultry Digest*, pp. 142 and 146 (1994).
Ashkenazi et al., "Safety and Immunogenicity of *Shigella sonnei* and *Shigella flexneri* 2a O-specific Polysaccharide Conjugates in Children," *J. Infect. Dis.*, Jun. 1999;179(6):1565-1568.
Ausubel et al., eds., *Current Protocols in Molecular Biology*, John Wiley & Sons, Inc., 1998; cover pg., publication pg., and table of contents only (12 pgs.).
Babu et al., "Effects of Live Attenuated and Killed *Salmonella* Vaccine on T-Lymphocyte Mediated Immunity in Laying Hens," *Vet. Immunol. Immunopathol.*, Jan. 10, 2003;91(1):39-44.
Banerjee-Bhatnagar et al., "Expression of *Neisseria meningitidis* iron-regulated outer membrane proteins, including a 70-kilodalton transferrin receptor, and their potential for use as vaccines," *Infect Immun.* Sep. 1990; 58(9):2875-2881.
Bannerman et al., "The bovine innate immune response during experimentally-induced *Pseudomonas aeruginosa* mastitis," *Vet. Immunopathol.*, 2005, 107:201-215.
Baumler et al., "IroN, a Novel Outer Membrane Siderophore Receptor Characteristic of *Salmonella enterica*" *Journal of Bacteriology*, Mar. 1988; 180(6):1446-1453.
Blaser et al., "*Campylobacter jejuni* Outer Membrane Proteins are Antigenic for Humans" *Infection and Immunity*, Mar. 1984; 43(3):986-993.
Bokete et al., "Genetic and Phenotypic Analysis of *Escherichia coli* with Enteropathogenic Characteristics Isolated from Seattle Children," *J. Infect. Dis.*, Jun. 1997;175(6):1382-1389.
Bolin et al., "Passive Immunization with Antibodies Against Iron-Regulated Outer Membrane Proteins Protects Turkeys from *Escherichia coli* Septicemia," *Infect Immun.*, May 1997;55(5):1239-1242.
Boothby et al., "Characterization of antigens from mycoplasmas of animal origin," *Am J Vet Res.* Mar. 1983; 44(3):433-439.
Bos et al., "Biogenesis of the gram-negative bacterial outer membrane" *Current Opinion in Microbiology*, 2004; 7:610-616.
Bosworth et al., "Vaccination with Genetically Modified Shiga-Like Toxin IIe Prevents Edema Disease in Swine," *Infect. Immun.*, Jan. 1996;64(1):55-60.

Bouchet et al., "Immunological variants of the aerobactin-cloacin DF13 outer membrane protein receptor IutA among enteric bacteria," *Infect Immun.* Jul. 1994; 62(7):3017-3021.
Bradley, "Bovine Mastitis: An Evolving Disease," *Vet. Journal*, 2002, 164/2:116-128.
Bragg et al., "Organization of proteins in the native and reformed outer membrane of *Escherichia coli*," *Biochim Biophys Acta*. Aug. 9, 1972;274(2):478-488. (No abstract available.).
Brogden et al., "Lysates of turkey-grown *Pasteurella multocida*: effects of solubilizing agents on the immunologic properties of membrane vesicles," *Am J Vet Res.* Mar. 1983;44(3):428-432.
Bruckmaier et al., "Changes of physiochemical indicators during mastitis and the effects of milk ejection on their sensitivity," *J. Dairy Res.*, 2004, 71/3:316-321 (abstract only).
Bruckmaier et al.,"Immunomediator and milk protein gene expression in mammary tissue during endotoxin-induced mastitis," *Livestock Production Science*, 2005; 98(1/2):81-87, abstract only (1 pg).
Burvenich et al., "Severity of *E. coli* mastitis is mainly determined by cow factors," *Vet. Res.*, 2003; 34:521-564.
Butterton et al., "Coexpression of the B Subunit of Shiga Toxin 1 and EaeA from Enterohemorrhagic *Escherichia coli* in *Vibrio cholerae* Vaccine Strains," *Infect. Immun.*, Jun. 1997;65(6):2127-2135.
Callaway et al, "Fecal prevalence and diversity of *Salmonella* species in lactating dairy cattle in four states" *J. Dairy Science*, 2005; 88(10): 3603-3608.
Calnek et al., Diseases of Poultry—9th ed., pp. 99-130, Iowa StateUniversity, Ames Iowa (1991).
CDC National Antimicrobial Resistance Monitoring System:Enteric Bacteria, available at www.cdc.gov/narms/, Apr. 5, 2005.
CDC *Salmonella* Surveillance: Annual Summary, 2002. Atlanta, GA: US Department of Health and Human Services, CDC, 2003.
CDC *Shigella* Surveillance: Annual Summary, 2002. Atlanta, GA: US Department of Health and Human Services, CDC, 2003.
Charles et al., "Adjuvanted Subunit Vaccines for the Control of *Salmonella enteritidis* Infection in Turkeys," *Am. J. Vet. Res.*, May 1994;55(5):636-642.
Chart et al., "Antigenic and Molecular Homology of the Ferric Enterobactin Receptor Protein of *Escherichia coli*," *J. Gen. Microbiol.*, Jun. 1985;131(6):1503-1509.
Chart et al., "Iron-regulated Outer-membrane Proteins of *Eschericia coli* Strains Associated with Enteric or Extraintestinal Diseases of Man and Animals," *J. Gen. Microbio.*, Jun. 1988; 134(6):1549-1559.
Choi-Kim et al., "Relationship between the iron regulated outer membrane proteins and the outer membrane proteins of in vivo grown *Pasteurella multocida*," *Vet Microbiol.* Jun. 1991;28(1):75-92.
Cohen et al., "Double-Blind Vaccine-Controlled Randomised Efficacy Trial of an Investigational *Shigella sonnei* Conjugate Vaccine in Young Adults," *Lancet*, Jan. 18, 1997;349(9046):155-159.
Corbett et al., "Effect of Iron Deprivation on Outer Membrane Proteins of *Pasteurella multocida*," Abstract, published in the Abstracts of the 85th Annual Meeting of the American Society for Microbiology, Las Vegas, Nevada, Mar. 3-7, 1985 (13 pgs).
Coster et al., "Vaccination Against Shigellosis with Attenuated *Shigella flexneri* 2a Strain SC602," *Infect. Immun.*, Jul. 1999;67(7):3437-3443.
Coulton et al., "Protein II influences ferrichrome-iron transport in *Escherichia coli* K12," *J Gen Microbiol.* Jan. 1979;110(1):211-220.
Courcol et al., "Siderophore production by *Staphylococcus aureus* and identification of iron-regulated proteins," *Infect. Immun.*, May 1997; 65(5):1944-1948.
Crichton, "Chapter 3. Microbial iron uptake and intracellular release" In: *Inorganic Biochemistry of Iron Metabolism*, Burgess, (ed)., 1991, Ellis Horwood Limited, Chichester, England, Title page and pp. 59-76.
Crist et al., *Mastits and its Control*, [online]. University of Kentucky, College of Agriculture. [retrieved on Jul. 15, 2002]. Retrieved from the Internet: <URL:http://www.ca.uky.edu/agc/pubs/asc/asc140/asc140.htm>; 22 pgs.

Crosa, "The relationship of plasmid-mediated iron transport and bacterial virulence," *Annu Rev Microbiol.* 1984;38:69-89. Review. (No abstract available.).
Crosa, "Genetics and Molecular Biology of Siderophore-Mediated Iron Transport in Bacteria," *Microbiol. Rev.*, Dec. 1989; 53(4):517-530.
Curtiss, III et al., "Live Oral Avirulent *Salmonella* Vaccines," *Vet. Microbiol.*, Nov. 1993;37(3-4):397-405.
Danve et al., "Transferrin-binding proteins isolated from *Neisseria meningitidis* elicit protective and bactericidal antibodies in laboratory animals," *Vaccine.* Sep. 1993; 11(12):1214-1220.
Davies et al., "Characterisation of bovine strains of *Pasteurella multocida* and comparison with isolates of avian, ovine and porcine origin," *Vet. Microbiology*, 2004, 99:145-158.
Davison et al., "Field Observations with *Salmonella enteritidis* Bacterins," *Avian Dis.*, Oct.-Dec. 1999;43(4):664-669.
Dziaba et al., "An Attempt to Immunize Pigs Against Colibacteriosis Under Field Conditions," *Medycyna Weterynaryjna*, 1984; 40(8):455-457 (English abstract on p. 457).
El-Shobaki et al., "Mucosal transferrin and ferritin factors in the regulation of iron absorption," *Res Exp Med (Berl).* Dec. 15, 1977;171(3):243-253.
Erdei et al., "Lactoferrin binds to porins OmpF and OmpC in *Escherichia coli*," *Infection and Immunity*, Apr. 1994; 62(4):1236-1240.
E-Toxate® (Technical Bulletin No. 210). SIGMA Chemical Company, St. Louis, MO, 1998. pp. 1-4.
Feng et al., "P55, an immunogenic but nonprotective 55-kilodalton *Borrelia burgdorferi* protein in murine Lyme disease," *Infect Immun.* Jan. 1996;64(1):363-365.
Ferguson et al., "Siderophore-mediated iron transport: crystal structure of FhuA with bound lipopolysaccharide," *Science.* Dec. 18, 1998;282(5397):2215-2220.
Field et al., "Influence of Iron on Growth, Morphology, Outer Membrane Protein Composition, and Synthesis of Siderophores in *Campylobacter jejuni*," *Infect. Immun.*, Oct. 1986;54(1):126-132.
Filip et al., "Solubilization of the cytoplasmic membrane of *Escherichia coli* by the ionic detergent sodium-lauryl sarcosinate," *J Bacteriol.* Sep. 1973;115(3):717-722.
Finkelstein et al., "Role of iron in microbe-host interactions," *Rev Infect Dis.* Sep.-Oct. 1983;5 Suppl 4: S759-776.
Francis et al., "Immunological priming with synthetic peptides of foot-and-mouth disease virus," *J Gen Virol.* Nov. 1985;66 ( Pt 11):2347-2354.
Fukutome et al., "Intestinal Mucosal Immune Response in Chickens Following Intraocular Immunization with Liposome-Associated *Salmonella enterica* Serovar *enteritidis* Antigen," *Dev. Comp. Immunol.*, Jun.-Jul. 2001;25(5-6):475-484.
Furugouri, "Iron binding substances in the intestinal mucosa of neonatal piglets," *J Nutr.* Mar. 1977; 107(3):487-494.
Gast et al., "Deposition of Phage Type 4 and 13a *Salmonella enteritidis* Strains in the Yolk and Albumen of Eggs Laid by Experimentally Infected Hens," *Avian Dis.*, Jul.-Sep. 2000;44(3):706-710.
Germanier et al., "Isolation and Characterization of Gal E Mutant Ty 21a of *Salmonella typhi*: A Candidate Strain for a Live, Oral Typhoid Vaccine," *J. Infect. Dis.*, May 1975;131(5):553-558.
Gilleland, Jr. et al., "Use of a purified outer membrane protein F (porin) preparation of *Pseudomonas aeruginosa* as a protective vaccine in mice," *Infect Immun.* Apr. 1984; 44(1):49-54.
Gilleland, Jr. et al., "Perspectives on the potential for successful development of outer membrane protein vaccines," *Eur J Clin Microbiol.* Jun. 1987;6(3):231-233. Review. (No abstract available.).
Gilmour et al., "Vaccine containing iron-regulated proteins of *Pasteurella haemolytica* A2 enhances protection against experimental pasteurellosis in lambs," *Vaccine.* Feb. 1991; 9(2):137-140.
Glisson et al., "In vivo antigen expression by *Pasteurella multocida*," *Avian Dis.* Apr.-Jun. 1991;35(2):392-396.
Glisson et al., "Cross-Protection Studies with *Pasteurella multocida* Bacterins Prepared from Bacteria propagated in Iron-Depleted Medium," *Avian Dis.*, Oct.-Dec. 1993; 37(4):1074-1079.

Goding, "*Monoclonal Antibodies: Principles and Practice*," Academic Press, 162-165 (1986).
Griffiths et al., "Naturally occurring antibodies in human sera that react with the iron-regulated outer membrane proteins of *Escherichia coli*," *Infect Immun.* Mar. 1985; 47(3):808-813.
Griffiths et al., "Pathogenic *Escherichia coli* express new outer membrane proteins when growing in vivo," *FEMS Microbiology Letters*, 16:95-99 (1983).
Gruet et al., "Bovine mastits and intramammary drug delivery: review and perspectives," *Advanced Drug Delivery Reviews*, 2001, 50:245-259.
Haddadi et al., "*E. coli* proteolytic activity in milk and casein breakdown," *Reprod. Nutr. Dev.*, 2005, 45:485-496 (abstract only).
Hancock et al., "Iron transport in *Escherichia coli* K-12: involvement of the colicin B receptor and of a citrate-inducible protein," *J. of Bacteriol.*, 127(3):1370-1375 (1976).
Harlow et al., "*Antibodies: A Laboratory Manual*," Cold Spring Harbor Laboratory, 689 (1988).
Hassan et al., "Development and Evaluation of an Experimental Vaccination Program Using a Live Avirulent *Salmonella typhimurium* Strain to Protect Immunized Chickens Against Challenge with Homologous and Heterologous *Salmonella* Serotypes," *Infect. Immun.*, Dec. 1994;62(12):5519-5527.
Heinrichs et al., "Identification and characterization of SirA, an iron-regulated protein from *Staphylococcus aureus*," *J. Bacteriol.* Mar. 1999; 181(5):1436-1443.
Helenius et al., "Solubilization of membranes by detergents," *Biochim Biophys Acta.* Mar. 25, 1975; 415(1):29-79. Review.
Hirst et al., "Iron-regulated outer membrane proteins of *Aeromonas salmonicida* are important protective antigens in Atlantic salmon against furunculosis," *Fish & Shellfish Immunology*, 1994;4:29-45.
Hjelmeland, "Solubilization of native membrane proteins," *Methods Enzymol.* 1990;182:253-264.
Hohmann et al., "*phoP/phoQ*-Deleted *Salmonella typhi* (Ty800) is a Safe and Immunogenic Single-Dose Typhoid Fever Vaccine in Volunteers," *J. Infect. Dis.*, Jun. 1996;173(6):1408-1414.
Hope et al., "An Overview of the *Salmonella enteritidis* Risk Assessment for Shell Eggs and Egg Products," *Risk Anal.*, Apr. 2002;22(2):203-218.
House et al., "Evaluation of an autogenous *Salmonella* bacterin and a modified live *Salmonella* serotype *choleraesuis* vaccine on a commercial dairy farm," *Am J Vet Res.* Dec. 2001;62(12):1897-1902.
Hudson et al., "Lymphokines and Cytokines," In: *Practical Immunology*, Oxford, Blackwell Scientific Publications, London, UK, 1989, 3rd Edition, 423-441.
Humphrey et al., "Contamination of Egg Shell and Contents with *Salmonella enteritidis*: a Review," *Int. J. Food Microbiol.*, Jan. 1994;21(1-2):31-40.
Hussain et al., "A Lithium Chloride-Extracted, Broad-Spectrum-Adhesive 42-Kilodalton Protein of *Staphylococcus epidermidis* is Ornithine Carbamoyltransferase," [online] *Infection and Immunity*, Dec. 1999; 67(12):6688-6690. [retrieved on Jul. 12, 2002]. Retrieved from the Internet: <URL:http://iai.asm.org/cgi/content/full/67/12/6688?view=full&pmid=10569792>. 8 pgs.
Ikeda et al., "Antigenically Related Iron-Regulated Outer Membrane Proteins Produced by Different Somatic Serotypes of *Pasteurella multocida*," *Infect. Immun.*, Sep. 1988; 56(9):2499-2502.
Jiang et al., "Ligand-Specific Opening of a Gated-Porin Channel in the Outer Membrane of Living Bacteria," *Science*, May 1997, 276:1261-1264.
Johansen et al., "Prevention of Edema Disease in Pigs by Vaccination with Verotoxin 2e Toxoid," *Can. J. Vet. Res.*, 1973; 61:280-285.
Jousimies et al., "Genetic Analysis of *Salmonella minnesota* R mutants with defects in the biosynthesis of the Lipopolysaccharide core," *J Bacteriol.* Sep. 1974;119(3):753-759.
Keler et al., "Metachromatic Assay for the Quantitative Determination of Bacterial Endotoxins," *Analyt. Biochem.* 1986; 156:189-193.
Khan et al., "Reducing Colonization of *Salmonella enteritidis* in Chicken by Targeting Outer Membrane Proteins," *J. Appl. Microbiol.*, 2003;95(1):142-145.

Kizil et al., "Identification and Characterization of TspA, a Major CD4+ T-Cell- and B-Cell-Stimulating *Neisseria*-Specific Antigen," [online]. [retrieved on Jul. 15, 2002]. Retrieved from the Internet: <URL:http://iai.asm.org/cgi/content/full/67/7/3533?maxtoshow= &HITS=10&hits=10&RESULTFORMAT= &searchid=1026752040493_2258&stored_search= &FIRSTINDEX=0&volume=67&firstpage=3533 &journalcode=iai>. 19 pgs.

Klebba et al., "Kinetics of biosynthesis of iron-regulated membrane proteins in *Escherichia coli*," *J Bacteriol.* Mar. 1982;149(3):880-888.

Koebnik et al., "Structure and function of bacterial outer membrane proteins: barrels in a nutshell," *Molecular Microbiology*, 2000, 37/2:239-253.

Köhler et al., "Continuous cultures of fused cells secreting antibody of predefined specificity," *Nature*, Aug. 7, 1975; 256 (5517):495-497.

Konadu et al., "Preparation, Characterization, and Immunological Properties in Mice of *Escherichia coli* O157 O-Specific Polysaccharide-Protein Conjugate Vaccines," *Infect. Immun.*, Nov. 1994;62(11):5048-5054.

Kotloff et al., "Safety, Immunogenicity, and Transmissibility in Humans of CVD 1203, a Live Oral *Shigella flexneri* 2a Vaccine Candidate Attenuated by Deletions in *aroA* and *virG*," *Infect. Immun.*, Nov. 1996;64(11):4542-4548.

Laemmli, "Cleavage of structural proteins during the assembly of the head of bacteriophage T4," *Nature*, Aug. 15, 1970; 227(259):680-685.

Lainson et al., "Identification and localization of an iron-regulated 35 kDa protein of *Pasteurella haemolytica* serotype A2," *J. Gen. Microbio.*, Feb. 1991, vol. 137(2): 219-226.

Lalmanach et al., "Host Cytokine Response and Resistance to *Salmonella* Infection," *Microbes Infect.*, Jul. 1999;1(9):719-726.

Lee et al., "Elevated Milk Soluble CD14 in Bovine Mammary Glands Challenged with *Escherichia coli* Lipopolysaccharide," *J. Dairy Science*, 2003, 86:2382-2389.

Lefcourt, "Method to Monitor the Precision of Milk Yields Recorded at Individual Milking Stalls on a Daily Basis," J. Dairy Sci 1999, 82:953-956.

Leitner et al., "Development of a *Staphylococcus aureus* Vaccine Against Mastitis in Dairy Cows. II. Field Trial," *Veterinary Immunology and Immunopathology*, 2003;93:153-158.

Lindsay et al., "*Staphylococcus aureus* but not *Staphylococcus epidermidis* can acquire iron from transferrin," *Microbiology*, 1995; 141:197-203.

Lindsay et al., "Staphylococcal iron requirements, siderophore production, and iron-regulated protein expression," *Infect. Immun.*, Jun. 1994; 62(6):2309-2314.

Lu et al., "A monoclonal antibody against a *Pasteurella multocida* outer membrane protein protects rabbits and mice against pasteurellosis," *Infect Immun.* Jan. 1991; 59(1):172-180.

Lu et al., "The outer membrane of *Pasteurella multocida* 3:A protects rabbits against homologous challenge," *Infect Immun.* Dec. 1991;59(12):4517-4523.

Lubke et al., "Isolation and partial characterization of the major protein of the outer membrane of *Pasteurella haemolytica* and *Pasteurella multocida*," *Zentralbl Bakteriol.* Jun. 1994;281(1):45-54.

Luderitz et al., "Lipopolysaccharides, the O antigens and endotoxins of gram-negative bacteria: Relationships of chemical structure and biological activity," *The Virulence of Escherichia coli*, Sussman, ed., The Society for General Microbiology, Academic Press, 73-88 (1985).

Lumsden et al., "Resistance to fecal shedding of *Salmonellae* in pigs and chickens vaccinated with an aromatic-dependent mutant of *Salmonella typhimurium*," *Am J Vet Res*. Nov. 1991;52(11):1784-1787.

Mäkelä et al., "Participation of lipopolysaccharide genes in the determination of the enterobacterial common antigen: analysis of R mutants of *Salmonella minnesota*," *J. Bacteriol.* Sep. 1974;119(3):760-764.

Maniatis et al., *Molecular cloning: A Laboratory Manual*, Cold Spring Harbor Lab., New York, 1982, Cover pg., Publication pg., and Table of Contents only (8 pgs.).

Manspeaker, "Metritis and Endometritis," [online]. *Northeast IRM Manual.* [retrieved on Jan. 25, 2005]. Retrieved from the Internet: <URL:http://www.wvu.edu/~exten/infores/pubs/livepoul/dirm22.pdf>. 4 pgs.

Matsui et al., "Specificity of protective immunity induced by porin from *Salmonella typhimurium*," *Microbiologica.* 1991;14:103-112.

Matthews-Greer et al., "Outer membrane protein F (porin) preparation of *Pseudomonas aeruginosa* as a protective vaccine against heterologous immunotype strains in a burned mouse model," *J Infect Dis.* Jun. 1987; 155(6):1282-1291.

Mazurier et al., "Visualization of lactotransferrin brush-border receptors by ligand-blotting," *Biochim Biophys Acta.* Dec. 19, 1985;821(3):453-460.

Mead et al., "Food-Related Illness and Death in the United States," *Emerg. Infect. Dis.*, Sep.-Oct. 1999;5(5):607-625.

Medearis, Jr. et al., "Cell wall composition and virulence in *Escherichia coli*," *J Exp Med*. Sep. 1, 1968; 128(3):399-414.

Meenakshi et al., "Adjuvanted Outer Membrane Protein Vaccine Protects Poultry Against Infection with *Salmonella enteritidis*," *Vet. Res. Commun.*, Mar. 1999; 23(2):81-90.

Merrifield, "Solid Phase Peptide Synthesis. I. The Synthesis of a Tetrapeptide," *J. Am. Chem. Soc.*, Jul. 20, 1963; 85(14):2149-2154.

Modun et al., "The *Staphylococcus aureus* and *Staphylococcus epidermidis* transferrin-binding proteins are expressed in vivo during infection," *Microbiology*, 1998; 144:1005-1012.

Morton et al., "Vaccination of cattle with outer membrane protein-enriched fractions of *Pasteurella haemolytica* and resistance against experimental challenge exposure," Am. J. Vet. Res., Jul. 1995, 56(7), 875-879.

Murray et al., "Antigenic analysis of iron-regulated proteins in *Pasteurella haemolytica* A and T biotypes by immunoblotting reveals biotype-specific epitopes," *J. Gen. Microbiol.* Feb. 1992;138( Pt 2):283-288.

Muthukkaruppan et al., "Monoclonal antibodies against *Salmonella* porins: generation and characterization," *Immunol. Lett.* Jul. 1992;33(2):201-206.

Nagaraja, "Influence of environment and other infectious agents on *E. coli* infections," *Poultry Digest*, p. 150 (1984).

Naiki et al., "Regulatory Role of Peritoneal NK1.1+ αβ T Cells in IL-12 Production During *Salmonella* Infection," *J. Immunol.*, Aug. 15, 1999;163(4): 2057-2063.

Nardelli-Haefliger et al., "Oral and Rectal Immunization of Adult Female Volunteers with a Recombinant Attenuated *Salmonella typhi* Vaccine Strain," *Infect. Immun.*, Dec. 1996;64(12):5219-5224.

Neilands, "Microbial iron compounds," *Annu Rev Biochem.* 1981;50:715-731.

Neilands, "Microbial envelope proteins related to iron," *Ann. Rev. Microbiol.*, 36:285-309 (1982).

Neugebauer, "Chapter 18: Detergents: An Overview," *Methods in Enzymology: Guide to Protein Purification*, Deutscher, Ed., Academic Press, San Diego, CA, 1990; 182:Cover pg., Publication pg., and 239-253.

Nikaido et al., "Chapter 3: Outer Membrane." *Escherichia coli and Salmonella typhimurium: Cellular and Molecular Biology*, Neidhardt et al., eds. *American Society for Microbiology*, Washington, D.C., 1987; Cover page, publication page, and 7-22.

Nilius et al., "Identification of extracellular siderophores of pathogenic strains of *Aspergillus fumigatus*," *J Med Vet Mycol.* 1990;28(5):395-403.

Ochoa-Reparaz et al., "Humoral Immune Response in Hens Naturally Infected with *Salmonella enteritidis* Against Outer Membrane Proteins and Other Surface Structural Antigens," *Vet. Res.*, May-Jun. 2004;35(3):291-298.

Ogawa et al., "Immunochemical and biological characterization of outer membrane proteins of *Porphyromonas endodontalis*," *Infect Immun.* Nov. 1992; 60(11):4528-4533.

Ogunnariwo et al., "Evidence for non-siderophore-mediated acquisition of transferrin-bound iron by *Pasteurella multocida*," *Microb Pathog*. Jul. 1991; 11(1):47-56.

Ogunnariwo et al., "Correlation between the ability of *Haemophilus paragallinarum* to acquire ovotransferrin-bound iron and the expression of ovotransferrin-specific receptors," *Avian Dis*. Jul.-Sep. 1992;36(3):655-663.

Okamura et al., "Differences Among Six *Salmonella* Serovars in Abilities to Colonize Reproductive Organs and to Contaminate Eggs in Laying Hens," *Avian Dis*., Jan.-Mar. 2001;45(1):61-69.

Okamura et al., "Differences in Abilities to Colonize Reproductive Organs and to Contaminate Eggs in Intravaginally Inoculated Hens and in vitro Adherences to Vaginal Explants Between *Salmonella enteritidis* and Other *Salmonella* Serovars," *Avian Dis*., Oct.-Dec. 2001;45(4):962-971.

Okamura et al., "Cell-Mediated Immune Responses to a Killed *Salmonella enteritidis* Vaccine: Lymphocyte Proliferation, T-Cell Changes and Interleukin-6 (IL-6), IL-1, IL-2, and IFN-γ Production," *Comp. Immunol. Microbiol. Infect. Dis*., Jul. 2004;27(4):255-272.

Osborn et al., "Proteins of the outer membrane of gram-negative bacteria," *Annu Rev Microbiol*. 1980;34:369-422.

Overbeek et al., "Carumonam enhances reactivity of *Escherichia coli* with mono- and polyclonal antisera to rough *Escherichia coli* J5," J Clin Microbiol. Jun. 1987; 25(6):1009-1013.

Perkins et al., "Probability-Based Protein Identification by Searching Sequence Databases Using Mass Spectrometry Data," *Electrophoresis*, Dec. 1999;20(18): 3551-3567.

Petsch et al., "Endotoxin removal from protein solutions," *Journal of Biotechnology*, 76: 97-119, 2000.

Product data Handbook: "Gel Filtration, Principles and Methods" handbook [online]. Amersham Biosciences AB, Uppsala, Sweden, 2002 [retrieved on Sep. 30, 2005]. Retrieved from the Internet: <URL:http://www.bioprocess.amershambiosciences.com/aptrix/upp00919.nsf/(FileDownload)?OpenAgent&docid=6EEE47990D9F933EC1256F90000DD697&file=18102218AI.pdf>; 124 pgs.

Product Data Sheet: Young, "Are You Monitoring Your Peak Milk and Days in Milk at Peak? Part A. Peak Milk," Utah State University, published Jan. 1999. [retrieved on Jan. 19, 2006]. Retrieved from the Internet: <URL:http://extension.usu.edu/files/agpubs/peaka.htm> 2 pgs.

Porter et al., "*Escherichia coli* antigens as dietary additives for oral immunisation of pigs: trials with pig creep feeds," *Vet Rec*. Jun. 16, 1973;92(24):630-636.

Rae, "Injection Site Reactions," [online]. University of Florida, Department of Animal Sciences, [retrieved on Oct. 16, 2003]. Retrieved from the Internet: <URL:http://www.animal.ufl.edu/extension/beef/documents/short94/rae.htm>. 3 pgs.

Rimler, "Cross-Protection Factor(s) of *Pasteurella multocida*: Passive-Immunization of Turkeys against Fowl Cholera Caused by Different Serotypes," *Avian Dis*., Oct.-Dec. 1987, 31(4);884-887.

Rimler, "Solubilization of Membrane-Associated Cross-Protection Factor(s) of *Pasteurella multocida*," *Avian Dis*., Apr.-Jun. 1989; 33(2):258-263.

Rimler, "Partial purification of cross-protection factor(s) from *Pasteurella multocida*," *Avian Dis*. Oct.-Dec. 1994;38(4):778-789.

Robledo et al., "Outer membrane proteins of *E. coli* in the host-pathogen interaction in urinary tract infection," *J. Urol*. Feb. 1990;143(2):386-391.

Roof et al., "Safety, efficacy, and duration of immunity induced in swine by use of an avirulent live *Salmonella choleraesuis*-containing vaccine," *Am J Vet Res*. Jan. 1995;56(1):39-44.

Sack et al., "Validation of a Volunteer Model of Cholera with Frozen Bacteria as the Challenge," *Infect. Immun*., May 1998;66(5):1968-1972.

Sanchez et al, "Cholera," *Lancet*, Jun. 21, 1997;349(9068):1825-1830.

Sansonetti et al., "Shigellosis: from Molecular Pathogenesis of Infection to Protective Immunity and Vaccine Development," *Res. Immunol*., Oct.-Dec. 1996;147(8-9):595-602.

Schierack et al., "Composition of intestinal Enterobacteriaceae populations of healthy domestic pigs" Microbiology, 2007; 153:3830-3837.

Schwartz et al., "Iron-regulated Proteins in Outer Membranes of *Campylobacter jejuni* Diarrhoea Isolates and Immune Response to the Proteins in Patients," *Zentralbl Bakteriol*., Jan. 1994;280(3):338-347.

Scopes, "Separation in Solution, Chapter 6," *Protein Purification Principles and Practice*, Second Edition, New York, NY, 1987, Title page, Publication pages, Table of Contents, and pp. 186-220 (23 pages total).

Snipes et al., "Plasma- and iron-regulated expression of high molecular weight outer membrane proteins by *Pasteurella multocida*," *Am J Vet Res*. Aug. 1988; 49(8):1336-1338.

Spier et al., "Persistent Experimental *Salmonella-dublin* Intramammary Infection in Dairy-Cows," *J. Vet. Internal Medicine*, Nov.-Dec. 1991; 5/6:341-350, abstract only (1 pg).

Stewart et al., *Solid Phase Peptide Synthesis*, $2^{nd}$ Edition, Pierce Chemical Co., Rockford IL, 1984; Cover page, Publication page, and Table of Contents only (7 pgs.).

Stocker, "Auxotrophic *Salmonella typhi* as Live Vaccine," *Vaccine*, Apr. 1988;6(2):141-145.

Stuart et al., "Iron-suppressible production of hydroxamate by *Escherichia coli* isolates," *Infect Immun*. Jun. 1982; 36(3):870-875.

Szu et al., "Laboratory and Preliminary Clinical Characterization of Vi Capsular Polysaccharide-Protein Conjugate Vaccines," *Infect. Immun*., Oct. 1994 ;62(10): 4440-4444.

Tabaraie et al., "Evaluation of *Salmonella* porins as a broad spectrum vaccine candidate," *Microbiol. Immunol*. 1994;38:553-559.

Tacket et al., "Comparison of the Safety and Immunogenicity of ΔaroC ΔaroD and Δcya Δcrp *Salmonella typhi* Strains in Adult Volunteers," *Infect. Immun*., Feb. 1992;60(2):536-541.

Tacket et al., "Clinical Acceptability and Immunogenicity of CVD 908 *Salmonella typhi* Vaccine Strain," *Vaccine*, 1992;10(7):443-446.

Tatusova et al., "BLAST 2 Sequences, a New Tool for Comparing Protein and Nucleotide Sequences," *FEMS Microbiol Lett*., May 15, 1999;174(2):247-250, and available at http://www.ncbi.nlm.nih.gov/gorf/b12.html.

Taylor et al., "Evaluation of a Bivalent (CVD 103-HgR/CVD 111) Live Oral Cholera Vaccine in Adult Volunteers from the United States and Peru," *Infect. Immun*., Sep. 1997;65(9):3852-3856.

Title 9: Animals and Animal Products, 9 CFR 113.120, 122, 123, undated, (2 pgs.), 2007.

Tokunaga et al., "Characterization of Porins from the Outer Membrane of *Salmonella typhimurium*," *Eur. J. Biochem*., 1979, 95:433-439.

Todhunter et al., "Antibodies to iron-regulated outer membrane proteins of coliform bacteria isolated from bovine intramammary infections," *Vet. Immunol. Immunopath*. 1991;28:107-115.

Trach et al., "Field Trial of a Locally Produced, Killed, Oral Cholera Vaccine in Vietnam," *Lancet*, Jan. 25, 1997;349(9047):231-235.

Trivier et al., "Influence of iron depletion on growth kinetics, siderophore production, and protein expression of *Staphylococcus aureus*," *FEMS Microbiol. Lett*., 1995; 127:195-199.

Truscott et al., "Demonstration of an outer membrane protein with antiphagocytic activity from *Pasteurella multocida* of avian origin," *Infect Immun*. Jun. 1988; 56(6):1538-1544.

Tufano et al., "Properties of *Yersinia enterocolitica* porins: interference with biological functions of phagocytes, nitric oxide production and selective cytokine release," *Res. Microbiol*. May 1994;145(4):297-307.

van der Helm, "Physical Biochemistry of FEPA and other Siderophore Receptor Proteins," *J. Inorg. Biochem*., 1995;59(2-3):90 (abstract only).

Vangroenweghe et al., "Increase of *Escherichia coli* Inoculum Doses Induces Faster Innate Immune Response in Primiparous Cows," J. Dairy Science, 2004; 87:4132-4144.

van Vliet et al., "Iron-Responsive Gene Regulation in a *Campylobacter jejuni fur* Mutant" *Journal of Bacteriology*, Oct. 1998; 180(20):5291-5298.

Vasfi Marandi et al., "The 32 kDa major outer-membrane protein of *Pasteurella multocida* capsular serotype D," *Microbiology*. Jan. 1996;142 ( Pt 1):199-206.

Villarreal-Ramos et al., "Immune Responses in Calves Immunised Orally or Subcutaneously with a Live *Salmonella typhimurium* aro Vaccine," *Vaccine*, Jan. 1998;16(1):45-54.

Visca et al., "Siderophore production by *Salmonella* species isolated from different sources," *FEMS Microbiol Lett.* Apr. 15, 1991;79(2-3):225-231.

Watson et al., eds. *Endotoxins and Their Detection With the Limulus Amebocyte Lystate Test*, Alan R. Liss, Inc. 150 5$^{th}$ Avenue, New York, 1982; cover page, publication page, and table of contents only (4 pgs.).

Wells et al., "What is the Current Milk Quality in the U.S.?" [online]. National Mastitis Council, [retrieved on Aug. 29, 2000]. Retrieved from the Internet: <URL:http://www.nmconline.org/articles/USQuality.htm>. 7 pgs.

Wellenberg et al., "Simultaneous intramammary and intranasal inoculation of lactating cows with bovine herpesvirus 4 induce subclinical mastitis, " *Vet. Microbiol.*, 2002, 86:115-129.

Williams et al., "Novel aerobactin receptor in *Klebsiella pneumoniae*," *J. Gen. Microbiol.* 1989;135:3173-3181.

Yokoyama et al., "Effect of oral egg antibody in experimental F18+ *Escherichia coli* infection in weaned pigs," *J. Vet. Med. Sci.* Oct. 1997;59(10):917-921.

Zhang et al., "Molecular Pathogenesis of *Salmonella enterica* Serotype *typhimurium*-Induced Diarrhea," *Infect. Immun.*, Jan. 2003; 71(1):1-12.

Zhao et al., "Expression of iron-regulated outer membrane proteins by porcine strains of *Pasteurella multocida*," *Can. J. Vet. Res.* 1995;59(1):46-50.

\* cited by examiner

□ Monthly average from the onset of the first *Salmonella* isolation

□ Monthly average one year after vaccination

IMMUNIZING COMPOSITIONS AND METHODS OF USE

CONTINUING APPLICATION DATA

This application is a continuation of application Ser. No. 11/386,393, filed on Mar. 22, 2006, which is a divisional application of application Ser. No. 10/454,305, filed on Jun. 3, 2003 (now U.S. Pat. No. 7,138,124), which is a divisional application of application Ser. No. 10/038,504, filed on Jan. 3, 2002 (now abandoned), which claims the benefit of U.S. Provisional Application Ser. No. 60/259,504, filed Jan. 3, 2001, and U.S. Provisional Application Ser. No. 60/262,896, filed Jan. 19, 2001 all of which are incorporated by reference herein.

BACKGROUND

The economic impact of infectious diseases in food animal production is well appreciated. Infectious diseases reduce profits, increase production costs, and endanger the overall wholesomeness of the food products, as well as effect the performance, health and welfare of the animal. This disease status can reduce the yield and quality of milk resulting in great economic loss to the dairymen. In some cases, infectious microbial diseases can cause morbidity and mortality of newborn, young (e.g., replacement stock) or adult animals.

The agricultural industry presently relies on antibiotic therapy and vaccines to decrease losses caused by clinical and subclinical infectious diseases, including gastrointestinal disease, respiratory disease, and systemic disease. However, for some conditions, antibiotics are ineffective, may prolong the condition, or induce a carrier state. Vaccines have often proven to be an effective means of controlling infectious diseases, but, concerns relating to adverse effects or lack of protection against multiple microbes have been a major drawback to current vaccines. For instance, vaccines are available that contain one or more immunogens against an individual genus, species, or strain of microbe; however, few, if any, provide cross-protection or stimulate broad-based immunity against multiple strains, species or genera of microbe.

Vaccines containing molecules obtained from gram negative microbes typically include contaminating levels of lipopolysaccharide (LPS), a component of the outer membrane of most gram negative microbes. The presence of LPS in an injectable product can result in an inflammatory response at the site of injection that can result in swelling, tenderness and often the formation of a granuloma at the site of injection. In rare cases, it can result in anaphylactic shock and death. This non-specific inflammatory response in a production animal can result in significant economic losses due to increasing the likelihood of disease by increasing the level of stress of the animal, and negatively effecting performance characteristics of the animal. In addition, the formation of a granuloma at the injection site can result in significant economic losses due to blemishes and scarring of the carcass which are often trimmed during processing resulting in the loss of product and down grading of the carcass. While methods for removal of LPS from compositions exist, this is often not feasible for use with vaccines that include whole cells. Moreover, due to the high costs of removing LPS from solutions, it is typically not economically practical to remove LPS from vaccines for use in non-human animals.

SUMMARY OF THE INVENTION

The presence of LPS in animal vaccines has a significant economic impact. However, the refusal of farmers to pay high fees for vaccines has prevented the use of available, but costly, methods for LPS removal. Accordingly, there is a long standing but unresolved need for methods for economically producing compositions containing molecules from gram negative microbes that contain low amounts of contaminating LPS. The present invention represents an advance in the art of economically isolating polypeptides from gram negative microbes with low levels of contaminating LPS. Accordingly, the present invention provides methods for isolating outer membrane polypeptides. The method includes providing a gram negative microbe, disrupting the gram negative microbe in a buffer, solubilizing the disrupted gram negative microbe, and isolating molecules of the gram negative microbe, wherein the isolated molecules include outer membrane polypeptides including at least two siderophore receptor polypeptides (SRPs) and at least two porins, and LPS at a concentration of no greater than about 10.0 endotoxin units per milliliter (EU/ml). During disrupting, the gram negative microbe may be present in the buffer at a concentration of between about 720 grams of microbe per 1,000 milliliters of buffer and about 1,080 grams of microbe per 1,000 milliliters of buffer. Solubilization of the gram negative microbe may occur for greater than about 24 hours. Solubilization of the gram negative microbe may occur in a solution including sarcosine, where the ratio of the sarcosine to gram weight of disrupted gram negative microbe is between about 0.8 gram sarcosine per about 4.5 grams of disrupted gram negative microbe and about 1.2 grams sarcosine per about 4.5 grams of disrupted gram negative microbe.

The present invention is also directed to a composition including at least two SRPs isolated from a gram negative microbe, at least two porins isolated from the gram negative microbe, and LPS at a concentration of no greater than about 10.0 EU/ml. The composition may further include a pharmaceutically acceptable carrier. The gram negative microbe may be an enteropathogen, preferably, a member of the family Enterobacteriaceae, more preferably, a member of the tribe Escherichieae or Salmonelleae, most preferably, *Salmonella* spp. or *Escherichia coli*. The at least two SRPs may have molecular weights of between about 60 kDa and about 100 kDa, and the at least two porins may have molecular weights of between about 30 kDa and about 43 kDa.

The present invention also represents an advance in the art of stimulating immunity to multiple strains, species, or genera of microbe. Accordingly, the present invention also provides a method for inducing the production of antibody in an animal. The method includes administering to an animal an effective amount of a composition of the present invention further including a pharmaceutically acceptable carrier, where the composition induces in the animal antibody that specifically binds at least one SRPs or at least one porin. The gram negative microbe may be an enteropathogen, preferably, a member of the family Enterobacteriaceae, more preferably, a member of the tribe Escherichieae or Salmonelleae, most preferably, *Salmonella* spp. or *Escherichia coli*. The animal may be an avian, a bovine, a caprine, a porcine, or an ovine. When the animal is a bovine, the bovine may exhibit a phenotype of, for instance, decreased somatic cell count, increased milk production, decreased fecal shedding, or increased weight.

The present invention is further directed to a method for inducing the production of antibody in an animal, where the method includes administering to an animal an effective amount of a composition that includes at least four SRPs isolated from a gram positive microbe and a pharmaceutically acceptable carrier, where the composition induces in the animal antibody to the SRP. The gram positive microbe may be a member of the family Micrococcaceae, for instance, *Staphylococcus aureus*. The SRPs may have molecular weights of between about 60 kDa and about 100 kDa.

Also provided by the present invention are methods for treating conditions in an animal, including, for instance, a high somatic cell count, fecal shedding of a microbe in an animal's intestinal tract, low milk production, mastitis in a milk producing animal, and metritis in an animal. The methods include administering to an animal having or at risk of having the condition an effective amount of a composition of the present invention, where the composition further includes a pharmaceutically acceptable carrier.

DETAILED DESCRIPTION OF PREFERRED EMBODIMENTS OF THE INVENTION

Compositions

Figure 1:
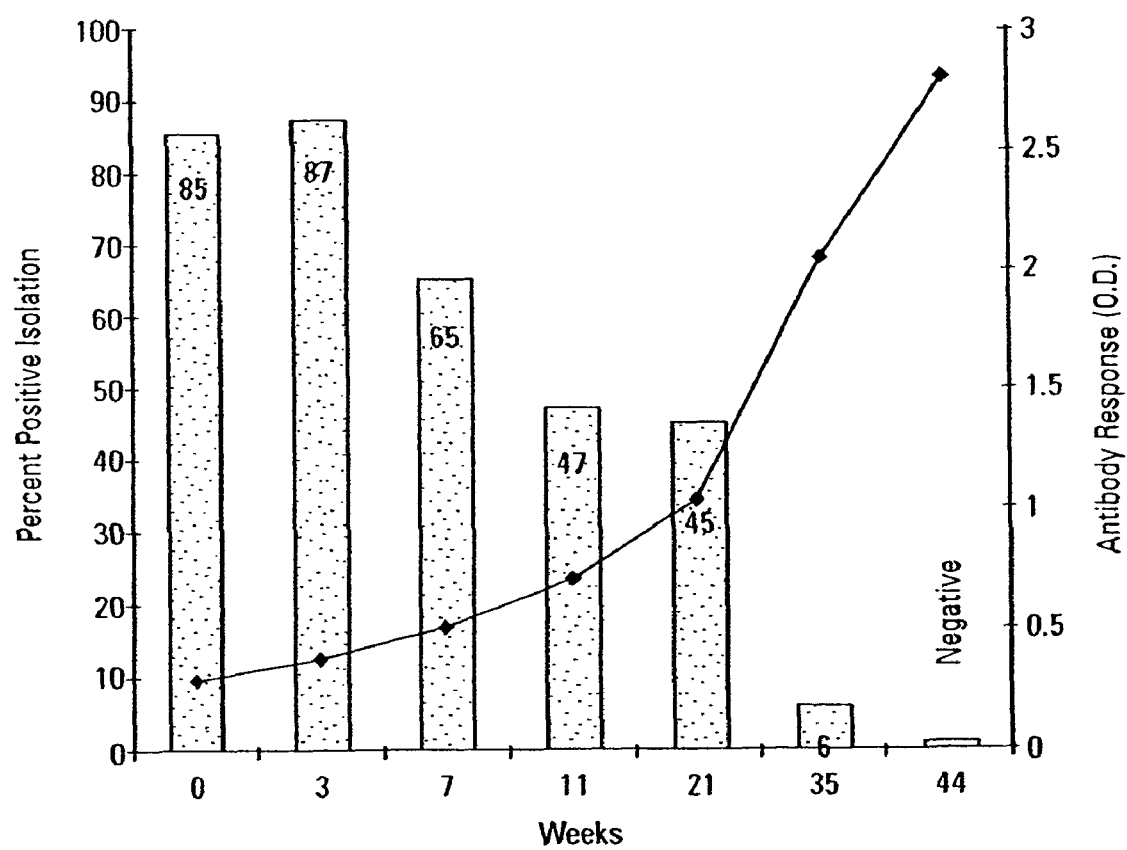
FIG. 1. Comparison of *Salmonella* isolation and serological response to vaccination in lactating cows. Percent positive isolation, percent of vaccinated lactating cows shedding *Salmonella bredeney*; antibody response (O.D.), optical density at 405 nm of antibody response as measured by ELISA. The bars correspond to the y-axis on the left (Percent Positive Isolation) and the open diamonds correspond to the y-axis on the right (Antibody Response (O.D.)).

One aspect of the present invention provides compositions including siderophore receptor polypeptides (SRPs) and porins obtained from a microbe. Unless otherwise specified, the term "microbe" includes both gram negative microbes and gram positive microbes. As used herein, "polypeptide" refers to a polymer of amino acids linked by peptide bonds and does not refer to a specific length of a polymer of amino acids. Thus, for example, the terms peptide, oligopeptide, protein, and enzyme are included within the definition of polypeptide. This term also includes post-expression modifications of the polypeptide, for example, glycosylations, acetylations, phosphorylations, and the like. A polypeptide can be produced using recombinant techniques, or chemically or enzymatically synthesized. Preferably, the polypeptides of the compositions of the present invention are isolated. An "isolated" polypeptide means a polypeptide that has been either removed from its natural environment, produced using recombinant techniques, or chemically or enzymatically synthesized. Unless otherwise specified, "a," "an," "the," and "at least one" are used interchangeably and mean one or more than one.

Gram negative microbes suitable for use in obtaining SRPs are those capable of producing SRPs when incubated under low iron conditions. Low iron conditions are described herein. Such gram negative microbes include enteropathogens, preferably, members of the family Enterobacteriaceae, more preferably, members of the family Enterobacteriaceae that are members of the tribe Escherichieae or Salmonelleae, even more preferably, *E. coli* or *Salmonella* spp. Examples of preferred enteropathogens include members of the family Enterobacteriaceae, members of the family Vibrionaceae (including, for instance, *Vibrio cholerae*), and *Campylobacter* spp. (including, for instance, *C. jejuni*). Examples of preferred members of the family Enterobacteriaceae include, for instance, *E. coli*, *Shigella* spp., *Salmonella* spp., *Proteus* spp., *Klebsiella* spp. (for instance, *Klebsiella pneumoniae*), *Serratia* spp., and *Yersinia* spp. Preferred examples of *Salmonella* spp. include *Salmonella enterica* serovars., *Bredeney, Dublin, Agona, Blockley, Enteriditis, Typhimurium, Hadar, Heidelberg, Montevideo, Muenster, Newport senftenberg, Salmonella cholerasuis*, and *S. typhi*. *Salmonella enterica* serovars *Bredeney, Dublin* and *Typhimurium* are referred to herein as *Salmonella bredeney, S. dublin*, and *S. typhimurium*, respectively. Preferred examples of strains of *E. coli* include, for example, *E. coli* scrotypes O1a, O2a, O78, and O157, different O:H serotypes including 0104, 0111, 026, 0113, 091, and hemolytic strains of enterotoxigenic *E. coli* such as K88$^+$, F4$^+$, F18ab$^+$, and F18ac$^+$. As used herein, the term "strain" refers to members of a species of microbe where the members have different genotypes and/or phenotypes. Other gram negative microbes include members of the family Pasteurellaceae, preferably *Pasturella* spp., more preferably, *Pasturella multocida* and *Pasteurella haemolytica*, and members of the family Pseudomonadaceae, preferably *Pseudomonas* spp., most preferably, *Pseudomonas aeruginosa*, Yet other gram negative microbes include *Actinobacillus* spp., *Haemophilus* spp., *Myxcobacteria* spp., *Sporocytophaga* spp., *Chondrococcus* spp., *Cytophaga* spp., *Flexibacter* spp., *Flavobacterium* spp., *Aeromonas* spp., among other gram-negative bacteria.

Gram positive microbes from which polypeptides may be obtained include members of the family Micrococcaceae, preferably, *Staphylococcus* spp., more preferably, *Staphylococcus aureus*. Other gram positive microbes include members of the family Deinococcaceae, preferably, *Streptococcus agalactiae, Streptococcus uberis, Streptococcus bovis, Streptococcus equi, Streptococcus zooepidemicus*, or *Streptococcus dysgalatiae*. Other gram positive microbes from which polypeptides can be isolated include *Bacillus* spp., *Clostridium* spp., *Corynebacterium* spp., *Erysipelothrix* spp., *Listeria* spp., and *Mycobacterium* spp., *Erysipelothrix* spp., and *Clostridium* spp.

These microbes are commercially available from a depository such as American Type Culture Collection (ATCC). In addition, such microbes are readily obtainable by isolation techniques known and used in the art. The microbes may be derived from an infected animal as a field isolate, and screened for production of SRPs, and introduced directly into low iron conditions, or stored for future use, for example, in a frozen repository at about −20° C. to about −95° C., preferably about −40° C. to about −50° C., in bacteriological media containing 20% glycerol, and other like media.

The present invention provides compositions including at least two, preferably, at least three, siderophore receptor polypeptides (SRPs). SRPs of gram negative microbes are polypeptides present in the outer membrane of gram negative microbes, and SRPs of gram positive microbes are polypeptides present in the membrane of gram positive microbes. In some aspects of the invention, SRPs are expressed by a microbe at high levels when the microbe is exposed to low iron conditions, and expressed at a substantially lower level when the microbe is exposed to high iron conditions. Preferably, SRPs are expressed by a microbe when the microbe is exposed to low iron conditions, and not expressed at detectable levels when the microbe is exposed to high iron conditions. Low iron conditions and high iron conditions are described in greater detail herein. Without intending to be limited by theory, it is believed that the SRPs of the present compositions are receptors of iron-binding siderophores. Examples of siderophore receptors expressed by gram negative microbes include, for instance, receptors for the uptake of aerobactin, enterobactin, ferric citrate, ferrichrome, rhodotorulic, and coprogen, as well as receptors for the transferrins (for instance the serotransferrins, lactotransferrin, and ovotransferrin), and other binding proteins, (see, for instance, Emery et al., U.S. Pat. No. 5,830,479, and Crichton, Microbial Iron Uptake and Intracellular Release. In: Inorganic Biochemistry of Iron Metabolism, Burgess, (ed)., Ellis Horwood Limited, Chichester, England, 59-76 (1991)).

Preferably, SRPs of the compositions of the present invention have immunogenic activity. "Immunogenic activity" refers to the ability of a polypeptide to elicit an immunological response in an animal. An immunological response to a polypeptide is the development in an animal of a cellular and/or antibody-mediated immune response to the polypeptide. Usually, an immunological response includes but is not limited to one or more of the following effects: the production of antibodies, B cells, helper T cells, suppressor T cells, and/or cytotoxic T cells, directed to an epitope or epitopes of the polypeptide. "Epitope" refers to the site on an antigen to which specific B cells and/or T cells respond so that antibody is produced.

It is known to the art that receptors of siderophores typically include epitopes that are conserved in the SRPs of different species and different genera of microbes (see, for instance, Emery et al. (U.S. Pat. No. 5,830,479) and Example 8). For instance, antibodies produced against an aerobactin receptor protein of one species, strain or genus of the family Enterobacteriaceae (for instance, *E. coli, Salmonella* spp., and *Klebsiella* spp.) have been found to cross-react with other microbes within the family. Species of *Pseudomonas* of the family Pseudomonadaceae also express siderophore receptor proteins that can be isolated as described herein and produce antibodies that cross-react with the receptor proteins of *E. coli, Salmonella* spp., and *Klebsiella* spp., among other members of the family Enterobacteriaceae. Moreover, antibodies produced against SRPs of *Salmonella* and against SRPs of *E. coli* have been found to cross react with the gram positive microbe *Staphylococcus aureus* (see Example 11).

A composition of the present invention may contain at least two, preferably, at least three, SRPs isolated from one or more genera or one or more species of microbe. In some aspects of the present invention, preferably the SRPs of a composition are derived from multiple species of the same genus of microbe, or from multiple strains of the same species of microbe. The present invention also includes compositions including SRPs isolated from at least one gram negative microbe and at least one gram positive microbe. Preferably, the molecular weights of SRPs, as determined by separation of the SRPs using an about 12% sodium dodecyl-polyacrylamide gel electrophoresis (SDS-PAGE) gel under reducing and denaturing conditions, are between about 60 kDa (kiloDaltons) and about 100 kDa, more preferably, between about 65 kDa and about 95 kDa.

Typically, different species of *Salmonella* each produce three SRPs. Without intending to be limited by theory, it is believed that the three SRPs produced by *Salmonella* spp. are receptors for the siderophores enterochelin, aerobactin, and ferrichrome. Preferably, SRPs obtained from *S. dublin* and *S. typhimurium* are combined. Preferably, the molecular weights of SRPs isolated from *Salmonella*, as determined by separation of the SRPs using an about 12% SDS-PAGE gel under reducing and denaturing conditions, are between about 60 kDa and about 100 kDa, more preferably, between about 65 kDa and about 95 kDa. More preferably, the molecular weights of SRPs isolated from *Salmonella* are as follows: between about 87 kDa and about 91 kDa, preferably about 89 kDa; between about 82 kDa and about 86 kDa, preferably about 84 kDa; and between about 69 kDa and about 75 kDa, preferably about 72 kDa.

*E. coli* have been found to produce 2, 3, 4, or 6 SRPs, depending on the serotype. Preferably, a composition that includes SRPs from *E. coli* includes, in increasing preference, at least two, at least three, at least four, or at least six SRPs isolated from *E. coli*. SRPs isolated from different *E. coli* strains can be combined. Preferably, the molecular weights of SRPs isolated from an *E. coli*, as determined by separation of the SRPs using an about 12% SDS-PAGE gel under reducing and denaturing conditions, are between about 60 kDa and about 100 kDa, more preferably, between about 65 kDa and about 95 kDa. More preferably, in a composition including SRPs isolated from an *E. coli*, the SRPs have molecular weights selected from between about 91 kDa and about 93 kDa, preferably about 92 kDa; between about 88 kDa and about 90 kDa, preferably about 89 kDa; between about 82 kDa and about 86 kDa, preferably about 84 kDa; between about 76 kDa and about 80 kDa, preferably about 78 kDa; between about 73 kDa and about 75 kDa, preferably about 74 kDa; and between about 71 kDa and about 73 kDa, preferably about 72 kDa. A preferred composition that includes SRPs isolated from *E. coli* is isolated from the *E. coli* deposited with the American Type Culture Collection, 10801 University Blvd., Manassas, Va., 20110-2209, USA, on Dec. 29, 1994, and designated ATCC #55652. The deposit was made under the Budapest Treaty on the International Recognition of the Deposit of Microorganisms for the Purposes of Patent Procedure.

Field isolates of the gram positive microbe *Staphylococcus aureus* has been found to produce at least about 4 SRPs. Preferably, when the composition includes SRPs from *S. aureus*, the SRPs are isolated from at least one species of *S. aureus*, more preferably, from one species of *S. aureus*. Preferably, the *S. aureus* is isolated from an avian animal suffering from a disease caused by *S. aureus*. Preferably, the molecular weights of four of the SRPs isolated from an *S. aureus*, as determined by separation of the SRPs using an about 10% SDS-PAGE gel under reducing and denaturing conditions, are between about 60 kDa and about 100 kDa, more preferably, between about 65 kDa and about 95 kDa. More preferably, the molecular weights of SRPs isolated from *S. aureus* are as follows: between about 88 kDa and about 92 kDa, preferably about 90 kDa; between about 82 kDa and about 86 kDa, preferably about 84 kDa; between about 70 kDa and about 74 kDa, preferably about 72 kDa; and between about 64 kDa and about 68 kDa, preferably about 66 kDa. Preferably, the molecular weights of the other three SRPs isolated from *S. aureus* are between about 35 kDa and about 37 kDa, preferably about 36 kDa; between about 30 kDa and about 34 kDa, preferably about 32 kDa; and between about 20 kDa and about 24 kDa, preferably about 22 kDa. Preferably, an *S. aureus* from which the SRPs are isolated is obtained from a bird, for instance a chicken or a turkey, displaying symptoms of a disease caused by the *S. aureus*, for instance, septicemia.

Preferably, SRPs of the present compositions can be identified using antibodies that specifically bind SRPs. As used herein, an antibody that can "specifically bind" a polypeptide is an antibody that interacts with the epitope of the antigen that induced the synthesis of the antibody, or interacts with a structurally related epitope. Such antibodies can be made using the *E. coli* strain having the designation ATCC #55652. Typically, ATCC #55652 is grown under low iron conditions, and SRPs are isolated from the strain as described in Example 1, or as described by, for example, Emery et al. (U.S. Pat. No. 5,830,479). Antibody is then made that specifically binds the SRPs using laboratory methods for producing polyclonal and monoclonal antibodies. Such laboratory methods are routine and known in the art (see, for instance, Harlow E. et al. *Antibodies: A laboratory manual* Cold Spring Harbor Laboratory Press, Cold Spring Harbor (1988) and Ausubel, R. M., ed. *Current Protocols in Molecular Biology* (1994)). Methods for determining whether SRPs of the present compositions are specifically bound by antibodies made using SRPs isolated from ATCC #55652 are routine and known to the art, and include, for instance, western immunoblot and enzyme linked immunosorbant assay.

The compositions of the present invention also include at least two porin polypeptides. Porin polypeptides are transmembraneous pore forming-proteins of the outer membrane of gram negative microbes. Gram negative bacteria have a cell wall with a thin peptidoglycan membrane layer in which small hydrophilic compounds can diffuse through the outer membrane by the porin pathway. Gram positive microbes have a thick peptidoglycan layer, which is porous and does not form a permeability barrier on the surface. It has been widely accepted that gram positive bacteria do not possess well-defined pore-forming proteins as compared to gram-negative bacteria. Nevertheless, recent evidence has shown identification of channel-forming activity in some members of the family Corynebacteriaceae. Unlike SRPs, the expression of porins does not change in response to the level of iron present in the medium in which a microbe is grown, and porin expression is typically constitutive. Without intending to be limited by theory, it is believed that the porins of the present compositions are polypeptides that produce pores or channels allowing passage of molecules across the outer membrane of gram negative microbes (see, for instance, Nikaido and Vaara, Outer Membrane, In: *Escherichia coli* and *Salmonella typhimurium*, Cellular and Molecular Biology, Neidhardt et al., (eds.) American Society for Microbiology, Washington, D.C., pp 7-22 (1987)) and the membrane of gram positive microbes. For instance, it is believed that the porins produced by gram negative microbes may include OmpA, OmpC, OmpD, OmpF, or PhoE. The porins are relatively conserved between gram negative bacteria, and play a role in iron binding. For example, OmpF and OmpC will bind lactoferrin (Erdei et al., *Infec. Immun.*, 62, 1236-1240 (1994)), while OmpA will bind ferrichrome (Coulton et al., *J. Gen. Microbiol.*, 110, 211-220 (1979)). Antibodies early in infection particularly of the IgM class have been found to cross-react with porins of *E. coli, Salmonella, Pasteurella, Pseudomonas* and *Klebsiella*, and will bind lactoferrin and/or ferrichrome, precluding the availability of an iron source for microbial growth. Without intending to be limited by theory, antibodies to these polypeptides will also bind to the porins on the surface to enhance opsonization and/or complement-mediated bacterial lysis.

A composition of the present invention may contain at least two porins isolated from one or more genera or one or more species of microbe. In some aspects of the present invention, preferably the porins of a composition are derived from multiple species of microbes of the same genus of microbe, or from multiple strains of the same species of microbe. In some aspects of the present invention, preferably the porins of a composition are derived from the same microbe from which the SRPs of the composition were isolated.

Preferably, porins of the compositions of the present invention have immunogenic activity. Without intending to be limiting, porins of the present composition act as an adjuvant to enhance the immune response of an animal to porins and SRPs present in a composition of the present invention when administered to an animal as described herein.

Preferably, the molecular weights of porins of the compositions of the present invention, as determined by separation of the porins using an about 12% SDS-PAGE gel under reducing and denaturing conditions, are between about 30 kDa and about 43 kDa, more preferably, between about 33 kDa and about 40 kDa. Preferably, the porins are obtained from a gram negative microbe. Typically, different species of *Salmonella* each produce at least two porins. Preferably, when the composition includes porins from a *Salmonella*, the porins are isolated from one species of *Salmonella*. Preferably, the molecular weights of porins isolated from *Salmonella* spp. are between about 37 kDa to about 40 kDa, more preferably, between about 38 kDa and about 39 kDa. Typically, *E. coli* produces at least two porins. Preferably, the molecular weights of porins isolated from *E. coli* are between about 33 kDa to about 39 kDa, more preferably, between about 34 kDa and about 38 kDa.

Preferably, porins of the present compositions can be identified using antibodies that specifically bind porins. Such antibodies can be made using the *E. coli* strain having the designation ATCC #55652. Typically, ATCC #55652 is grown under low iron conditions, and porins are isolated from the strain as described in Example 1, or as described by Emery et al. (U.S. Pat. No. 5,830,479). Antibody is then made that specifically binds the porins. Laboratory methods for producing polyclonal and monoclonal antibodies are routine and known in the art (see, for instance, Harlow E. et al. *Antibodies: A laboratory manual* Cold Spring Harbor Laboratory Press, Cold Spring Harbor (1988) and Ausubel, R. M., ed. *Current Protocols in Molecular Biology* (1994)). Methods for determining whether porins of the present compositions are specifically bound by antibodies made using porins isolated from ATCC #55652 are routine and known to the art, and include, for instance, western immunoblot and enzyme linked immunosorbant assay.

Preferably, the compositions of the present invention include low concentrations, more preferably, undetectable concentrations, of lipopolysaccharide (LPS). LPS is a component of the outer membrane of most gram negative microbes (see, for instance, Nikaido and Vaara, Outer Membrane, In: *Escherichia coli* and *Salmonella typhimurium*, Cellular and Molecular Biology, Neidhardt et al., (eds.) American Society for Microbiology, Washington, D.C., pp. 7-22 (1987), and typically includes polysaccharides (O-specific chain, the outer and inner core) and the lipid A region. The lipid A component of LPS is the most biologically active component of the LPS structure and together induce a wide spectrum of pathophysiological effects in mammals. The most dramatic effects are fever, disseminated intravascular coagulation, complement activation, hypotensive shock, and death. LPS plays a major role in the activation of various cell types, particularly those of lymphoid origin. This activation results in the production of an impressive array of endogenous mediators that, in turn, activate the complement system, impair mitochondrial function, activate lysosomal activity, stimulate prostaglandin activity, and cause macrophage cytotoxicity and tumoricidal activity. This non-specific immunostimulatory activity of LPS can enhance the formation of a granuloma at the site of administration of compositions that include LPS. Such reactions can result in undue stress on the animal by which the animal may back off feed or water for a period of time, and exasperate infectious conditions in the animal. In addition, the formation of a granuloma at the site of injection can increase the likelihood of possible down grading of the carcass due to scaring or blemishes of the tissue at the injection site (see, for instance, Rae, Injection Site Reactions, available on the world wide web at animal.uft-edu/short94/rae.htm.

The concentration of LPS can be determined using routine methods known to the art. Such methods typically include measurement of dye binding by LPS (see, for instance, Keler and Nowotny, *Analyt. Biochem.*, 156, 189 (1986)) or the use of a *Limulus* amebocyte lysate (LAL) test (see, for instance, Endotoxins and Their Detection With the *Limulus* Amebocyte Lystate Test, Alan R. Liss, Inc., 150 Fifth Avenue, New York, N.Y. (1982)). There are four basic commercially available methods that are typically used with an LAL test: the gel-clot test; the turbidimetric (spectrophotometric) test; the colorimetric test; and the chromogenic test. An example of a gel-clot assay is available under the tradename E-TOXATE (Sigma Chemical Co., St. Louis, Mo.; see Sigma Technical Bulletin No. 210). Typically, assay conditions include contacting the composition with a preparation containing a lysate of the circulating amebocytes of the horseshoe crab, *Limulus polyphemus*. When exposed to LPS, the lysate increases in opacity as well as viscosity and may gel. About 0.1 milliliter of the composition is added to lysate. Typically, the pH of the composition is between 6 and 8, preferably, between 6.8 and 7.5. The mixture of composition and lysate is incubated for about 1 hour undisturbed at about 37° C. After incubation, the mixture is observed to determine if there was gelation of the mixture. Gelation indicates the presence of endotoxin. To determine the amount of endotoxin present in the composition, dilutions of a standardized solution of endotoxin are made and tested at the same time that the composition is tested. Standardized solutions of endotoxin are commercially available from, for instance, Sigma Chemical (Catalog No. 210-SE) and U.S. Pharmacopeia (Rockville, Md., Catalog No. 235503). In increasing order of preference, a composition of the present invention has no greater than about 10.0 endotoxin units per milliliter (EU/ml), no greater than about 5.0 EU/ml, no greater than about 1.0 EU/ml, no greater than about 0.5 EU/ml, no greater than about 0.2 EU/ml, no greater than about 0.1 EU/ml, most preferably, no greater than about 0.05 EU/ml. An endotoxin unit (EU) is defined in comparison to the current FDA Endotoxin Reference Standard Lot EC-5. One vial of lot EC-5 contains 10,000 EU. In general, about 1 nanogram (ng) of pure LPS is equal to between about 5 and about 10 endotoxin units.

The compositions of the present invention optionally further include a pharmaceutically acceptable carrier. "Pharmaceutically acceptable" refers to a diluent, carrier, excipient, salt, etc, that is compatible with the other ingredients of the composition, and not deleterious to the recipient thereof. Typically, the composition includes a pharmaceutically acceptable carrier when the composition is used as described below in "Methods of Use." The compositions of the present invention may be formulated in pharmaceutical preparations in a variety of forms adapted to the chosen route of administration, preferably, routes suitable for stimulating an immune response to an antigen. Thus, a composition of the present invention can be administered via known routes including, for example, oral; parental including intradermal, subcutaneous, intramuscular, intravenous, intraperitoneal, etc., and topically, such as, intranasal, intrapulmonary, intramammary, intravaginal, intrauterine, etc. It is foreseen that a composition can be administered to a mucosal surface, such as by administration to the nasal or respiratory mucosa (e.g. spray or aerosol), to stimulate mucosal immunity, such as production of secretory IgA antibodies, throughout the animal's body.

A composition of the present invention can also be administered via a sustained or delayed release implant. Suitable implants are known. Some examples of implants suitable for use according to the invention are disclosed in Emery and Straub (WO 01/37810). Implants can be produced at sizes small enough to be administered by aerosol or spray. Implants also include nanospheres and microspheres.

A composition of the present invention is administered in an amount sufficient to provide an immunological response to SRPs and/or porins present in the composition, and/or increase performance characteristics. Performance characteristics are described in greater detail herein. The amount of the polypeptide present in a composition of the present invention can vary. For instance, the dosage of polypeptide can be between about 0.01 micrograms (μg) and about 300 milligrams (mg), typically between about 0.1 mg and about 10 mg. For an injectable composition (e.g. subcutaneous, intramuscular, etc.) the polypeptide is preferably present in the composition in an amount such that the total volume of the composition administered is about 0.5 ml to 5.0 ml, typically about 1.0-2.0 ml. The amount administered will vary depending on various factors including, but not limited to, the specific polypeptides chosen, the weight, physical condition and age of the animal, and the route of administration. Thus, the absolute weight of the polypeptide included in a given unit dosage form can vary widely, and depends upon factors such as the species, age, weight and physical condition of the animal, as well as the method of administration. Such factors can be determined by one of skill in the art. Other examples of dosages suitable for the invention are disclosed in Emery et al. (U.S. Pat. No. 6,027,736).

The formulations may be conveniently presented in unit dosage form and may be prepared by methods well known in the art of pharmacy. All methods of preparing a composition including a pharmaceutically acceptable carrier include the step of bringing the active compound (e.g., SRPs and/or porins as described herein) into association with a carrier that constitutes one or more accessory ingredients. In general, the formulations are prepared by uniformly and intimately bringing the active compound into association with a liquid carrier, a finely divided solid carrier, or both, and then, if necessary, shaping the product into the desired formulations.

A composition including a pharmaceutically acceptable carrier can also include an adjuvant. An "adjuvant" refers to an agent that can act in a nonspecific manner to enhance an immune response to a particular antigen, thus potentially reducing the quantity of antigen necessary in any given immunizing composition, and/or the frequency of injection necessary in order to generate an adequate immune response to the antigen of interest. Adjuvants may include for example, IL-1, IL-2, emulsifiers, muramyl dipeptides, dimethyldiocradecylammonium bromide (DDA), pyridine, aluminum hydroxide, oils, saponins, alpha-tocopberol, polysaccharides, emulsified paraffins (available from under the tradename EMULSIGEN from MVP Laboratories, Ralston, Nebr.), ISA-70, RIBI and other substances known in the art.

In another embodiment, an composition of the invention including a pharmaceutically acceptable carrier can include a biological response modifier, such as, for example, IL-2, IL-4 and/or IL-6, TNF, IFN-alpha, IFN-gamma, and other cytokines that effect immune cells. An immunizing composition can also include an antibiotic, preservative, anti-oxidant, chelating agent, etc. Such components are known in the art.

Another aspect of the present invention provides improved methods for obtaining SRPs from gram negative microbes and improved methods for obtaining porin polypeptides from gram negative microbes. The methods include providing a gram negative microbe, disrupting the microbe, solubilizing the microbe, and isolating the polypeptides.

A gram negative microbe to be provided in the method is incubated under conditions that promote the expression of SRPs. Typically, such conditions are low iron conditions. As used herein, the phrase "low iron conditions" refers to an environment, typically bacteriological media, that contains amounts of free iron that cause a microbe to express SRPs. As used herein, the phrase "high iron conditions" refers to an environment that contains amounts of free iron that cause a microbe to not express SRPs. Preferably, low iron conditions are the result of the addition of an iron chelating compound to media, and high iron conditions are present when a chelator is not present in the media. Examples of iron chelators include 2,2'-dipyridyl (also referred to in the art as α,α'-bipyridyl), 8-hydroxyquinoline, ethylenediamine-di-O-hydroxyphenylacetic acid (EDDHA), desferrioxamine methanesulphonate (desferol), transferrin, lactoferrin, ovotransferrin, biological siderophores, such as, the catecholates and hydroxamates, and citrate. Preferably, 2,2'-dipyridyl is used. Typically, 2,2'-dipyridyl is added to the media at a concentration of about 25 micrograms/milliliter ($\lambda$g/ml), more preferably, at about 50 µg/ml, most preferably, at about 100 µg/ml. The media used to incubate the microbe is not critical, and varies depending on the microbe. For instance, when the microbe is *Salmonella* spp. or *E. coli*, tryptic soy broth or brain heart infusion may be used. The volume of media used to incubate the microbe can vary. When a microbe is being evaluated for the ability to produce SRPs and porins, the microbe can be grown in a suitable volume, for instance, 10 milliliters to 1 liter of medium. When a microbe is being grown to obtain SRPs and porins for use in, for instance, administration to animals, the microbe may be grown in a fermentor to allow the isolation of larger amounts of polypeptides. Methods for growing microbes in a fermentor are routine and known to the art. The conditions used for growing a microbe preferably include an iron chelator, preferably 2,2'-dipyridyl, a pH of between about 6.5 and about 7.5, preferably between about 6.9 and 7.1, and a temperature of about 37° C. Optionally, when a fermentor is used, dissolved oxygen is maintained at between about 20% and about 40%, preferably, about 30%, but may vary depending on the metabolic requirements of the organism.

After growth, the gram negative microbe that is to be provided in the method is harvested. Harvesting includes concentrating the microbe into a smaller volume and suspending in a media different than the growth media. Methods for concentrating a microbe are routine and known to the art, and include, for example, centrifugation. Typically, the concentrated microbe is suspended in decreasing amounts of buffer. Preferably, the final buffer includes a metal chelator, preferably, ethylenediaminetetraacetic acid (EDTA), which also aids in the release of lipopolysaccharide from the cell wall. Preferably, the final buffer also minimizes proteolytic degradation. This can be accomplished by having the final buffer at a pH of greater than about 8.0, preferably, at least about 8.5, and/or including one or more proteinase inhibitors (e.g., phenylmethanesulfonyl fluoride). Optionally and preferably, the concentrated microbe is frozen at −20° C. or below until disrupted.

The gram negative microbe may be disrupted using chemical, physical, or mechanical methods routine and known to the art, including, for example, french press, sonication, or homoginization. Preferably, homoginization is used. As used herein, "disruption" refers to the breaking up of the cell. Disruption of a microbe can be measured by methods that are routine and known to the art, including, for instance, changes in optical density. Typically, a microbe is subjected to disruption until the optical density does not change after further disruption. For instance, if percent transmittance is measured, the microbe is disrupted until the percent transmittance does not increase after further disruption. Preferably, the microbe is present in a buffer that minimizes proteolytic degradation. Preferably, the microbe is present in the buffer at a concentration of between about 720 grams of microbe per 1,000 milliliters of buffer and about 1,080 grams of microbe per 1,000 milliliters of buffer, more preferably, between about 810 grams of microbe per 1,000 milliliters of buffer to about 990 grams of microbe per 1,000 milliliters of buffer, most preferably, about 900 grams microbe per 1,000 milliliters of buffer. The temperature during disruption is typically kept low, preferably at about 4° C., to further minimize proteolytic degradation.

The disrupted microbe is solubilized in a detergent, for instance, an anionic, zwitterionic, nonionic, or cationic detergent. Preferably, the detergent is sarcosine, more preferably, sodium lauroyl sarcosinate. As used herein, the term "solubilize" refers to dissolving cellular materials (e.g., polypeptides, nucleic acids, carbohydrates) into the aqueous phase of the buffer in which the microbe was disrupted, and the formation of aggregates of insoluble cellular materials. The conditions for solubilization preferably result in the aggregation of SRPs and/or porins into insoluble aggregates that are large enough to allow easy isolation by, for instance, centrifugation. The ability to produce insoluble aggregates was unexpected, and provides for an economical way to isolate SRPs and porins.

Preferably, the sarcosine is added such that the final ratio of sarcosine to gram weight of disrupted microbe is between about 0.8 gram sarcosine per about 4.5 grams pellet mass and about 1.2 grams sarcosine per about 4.5 grams pellet mass, preferably, about 1.0 gram sarcosine per about 4.5 grams pellet mass. The solubilization of the microbe may be measured by methods that are routine and known to the art, including, for instance, changes in optical density. Typically, a disrupted microbe is allowed to solubilize until the percent transmittance at about 540 nm is between about 25% and about 30%. Preferably, the solubilization is allowed to occur for at least about 24 hours, more preferably, at least about 48 hours, most preferably, at least about 60 hours. The temperature during disruption is typically kept low, preferably at about 4° C.

The insoluble aggregates that include the SRPs and porins may be isolated by methods that are routine and known to the art. Preferably, the insoluble aggregates are isolated by centrifugation. Typically, centrifugation of outer membrane polypeptides that are insoluble in detergents requires centrifugal forces of at least 50,000×g, typically about 100,000×g. The use of such centrifugal forces requires the use of ultracentrifuges, and scale-up to process large volumes of sample is often difficult and not economical with these types of centrifuges. Surprisingly and unexpectedly, the methods described herein provide for the production of insoluble aggregates large enough to allow the use of significantly lower centrifugal forces (for instance, about 46,000×g). Methods for processing large volumes at these lower centrifugal forces are available and known to the art. Thus, the insoluble aggregates can be isolated at a significantly lower cost.

Optionally and preferably, the sarcosine is removed from the isolated SRPs and porins. Methods for removing sarcosine from the isolated polypeptides are known to the art, and include, for instance, diafiltration, precipitation, hydrophobic, ion-exchange, and/or affinity chromatography, and ultra filtration and washing the polypeptides in alcohol by diafiltration. After isolation, the polypeptides suspended in buffer and stored at low temperature, for instance, −20° C. or below.

Another unexpected observation was that this method for obtaining SRPs and proins from a gram negative microbe also resulted in SRPs and porins containing low amounts of LPS. LPS is a potent immunostimulant, and when present in compositions that are administered to animals, especially mammals, can result in decreases in certain performance characteristics, and/or injection site reactions that can result in the downgrading of carcasses due to scaring or blemishes of tissue at the injection site. The ability to isolate SRPs and porins with low amounts of LPS results in decreased economic losses associated with administration of preparations from gram negative microbes. The decreased amount of LPS results in fewer condemned and/or downgraded carcasses at slaughter, and fewer decreases in performance characteristics.

SRPs may also be isolated from gram positive microbes using methods that are known to the art. The isolation of SRPs from gram positive microbes can be accomplished as described in, for instance, Hussain, et al. *Infect. Immun.*, 67, 6688-6690 (1999); Trivier, et al., *FEMS Microbiol. Lett.*, 127, 195-199 (1995); Heinrichs, et al., *J. Bacteriol.*, 181, 1436-1443 (1999).

Methods of Use

An aspect of the present invention is further directed to methods of using the compositions of the present invention. The methods include administering to an animal an effective amount of a composition of the present invention. Preferably, the composition includes LPS at a concentration of, in increasing order of preference, no greater than about 10.0 endotoxin units per milliliter (EU/ml), no greater than about 5.0 EU/ml, no greater than about 1.0 EU/ml, no greater than about 0.5 EU/ml, no greater than about 0.1 EU/ml, most preferably, no greater than about 0.05 EU/ml. Preferably, the composition further includes a pharmaceutically acceptable carrier. The animal can be, for instance, avian (including, for instance, chickens or turkeys), bovine (including, for instance, cattle), caprine (including, for instance, goats), ovine (including, for instance, sheep), porcine (including, for instance, swine), Bison (including, for instance, buffalo), companion animals (including, for instance, horses), members of the family Cervidae (including, for instance, deer, elk, moose, caribou and reindeer), and humans.

In some aspects, the methods may further include additional administrations (e.g., one or more booster administrations) of the composition to the animal to enhance or stimulate a secondary immune response. A booster can be administered at about 1 week to about 8 weeks, preferably about 2 to about 4 weeks, after the first administration of the composition. Subsequent boosters can be administered one, two, three, four, or more times annually. Without intending to be limited by theory, it is expected that annual boosters will not be necessary, as an animal will be challenged in the field by exposure to microbes expressing SRPs and/or porins having epitopes that are identical to or structurally related to epitopes present on the SRPs and/or porins of the composition administered to the animal.

In one aspect, the invention is directed to methods for inducing the production of antibody in an animal. The antibody produced includes antibody that specifically binds at least one polypeptide (an SRP and/or a porin) present in the composition. In this aspect of the invention, an "effective amount" is an amount effective to result in the production of antibody in the animal. Methods for determining whether an animal has produced antibodies that specifically bind polypeptides present in a composition of the present invention can be determined as described herein.

The method may be used to produce antibody that specifically binds polypeptides, preferably, SRPs and/or porins, present on the surface of a microbe other than the microbe from which the SRPs and porins of the composition were isolated. As discussed herein, SRPs and porins typically include epitopes that are conserved in the SRPs and porins of different species and different genera of microbes. Accordingly, antibody produced using SRPs and porins from one microbe are expected to bind to SRPs and/or porins present on other microbes (see, for instance, Examples 8 and 10) and provide broad spectrum protection against gram positive and gram negative organisms. Examples of gram positive microbes to which the antibody specifically binds are members of the family Micrococcaceae, members of the family Deinococcaceae, or other gram positive microbes as described in the section "Compositions." Preferably, gram positive microbes to which the antibody binds are *Staphylococcus aureus, Streptococcus agalactiae, Streptococcus uberis, Streptococcus bovis* and *Streptococcus dysgalatiae, Streptococcus zooepidemicus*, and *Streptococcus equi*, most preferably, *Staphylococcus aureus*. Examples of gram negative microbes to which the antibody specifically binds are enteropathogens, more preferably, members of the family Enterobacteriaceae, even more preferably, members of the Enterobacteriaceae tribes Escherichieae or Salmonelleae, as described in the section "Compositions." Most preferably, gram negative microbes to which the antibody specifically binds are *Salmonella* spp. and *E. coli*.

In an alternative aspect, methods for inducing the production of antibody in an animal include administering a composition prepared from a whole cell preparation. According to this embodiment, the whole cell preparation can be prepared from, for example, a modified *Escherichia coli* such as a virulent R-mutant, as for example, *E. coli* J5 (commercially available from ATCC as ATCC #43745; described by Overbeck et al., *J. Clin. Microbiol.*, 25, 1009-1013 (1987)), or *Salmonella minnesota* (commercially available from ATCC as ATCC number #49284; as described by Sanderson et al., *J. Bacteriol.*, 119, 753-759, 760-764 (1974)) that lack outer oligosaccharide side chains of LPS. In a non-immunized animal outer oligosaccharide side chains tend to mask SRPs on the cell membrane in such a way that the immune system does not recognize the SRPs and production of anti-SRP antibody titers are depressed. Thus, to enhance the immune stimulating capability of an immunizing composition made with intact bacterial cells to elicit an anti-SRP immune response, the cell membrane can be chemically altered to eliminate the interfering oligosaccharide side chains or a mutant organism such as the *E. coli* J5 organism discussed above can be used. Chemically modified cells or mutants are then grown under iron-restriction conditions to enhance SRP production as described in, for example, U.S. Pat. No. 6,027,736.

In another aspect, the present invention is directed to methods for treating certain conditions in animals that may be caused by, or associated with, a microbe. Such conditions include, for instance, gram negative microbial infections and gram positive microbial infections. Examples of conditions caused by microbial infections include mastitis, fecal shedding of a microbe, metritis, strangles, intrauterine infections, odema disease, enteritis, chronic reproductive infections, laminitis, and acute or chronic Chlamydiosis, Colibacillosis, Ehrlichiosis, Leptospirosis, Pasteurellosis, Pseudotuberculosis, Salmonellosis. Examples of conditions that may be caused by microbial infections include performance characteristics such as decreased milk production, high somatic cell counts, and weight loss. Treatment of these conditions can be prophylactic or, alternatively, can be initiated after the development of a condition described herein. Treatment that is prophylactic, for instance, initiated before a subject manifests symptoms of a condition caused by a microbe, is referred to herein as treatment of a subject that is "at risk" of developing the condition. Typically, an animal "at risk" of developing a condition is an animal present in an area where the condition has been diagnosed and/or is likely to be exposed to a microbe causing the condition. Accordingly, administration of a composition can be performed before, during, or after the occurrence of the conditions described herein. Treatment initiated after the development of a condition may result in decreasing the severity of the symptoms of one of the conditions, or completely removing the symptoms. Preferably, administration of a compound is performed before the occurrence of the conditions described herein. In this aspect of the invention, an "effective amount" is an amount effective to prevent the manifestation of symptoms of a disease, decrease the severity of the symptoms of a disease, and/or completely remove the symptoms. The potency of a composition of the present invention can be tested according to standard methods established by 9 CFR §113. For instance, 9 CFR §113.120(c) and 9 CFR §13.123(c) describe standard methods for determining the potency of the composition against a standard reference bacterin of *Salmonella typhimurium* and *Salmonella dublin*, respectively. Methods for determining whether an animal has the conditions disclosed herein and symptoms associated with the conditions are routine and known to the art.

In one aspect the invention is also directed to treating a gram negative microbial infection in an animal, and/or a gram positive infection in an animal. The method includes administering an effective amount of the composition of the present invention to an animal having or at risk of having a gram positive or a gram negative infection, and determining whether at least one symptom of infection is reduced.

In another aspect, the invention provides for treatment of mastitis in milk producing animals, such as cattle. The method includes administering an effective amount of the composition of the present invention to a milk producing animal having or at risk of having mastitis, and determining whether at least one symptom of mastitis is reduced. Mastitis refers to inflammation of the mammary gland. Physical, chemical and usually bacteriological changes in the milk and pathological changes in the glandular tissue characterize it. These glandular changes often result in a number of symptomatic conditions such as, discoloration of the milk, the presence of clots and the presence of large numbers of leukocytes. Clinically, mastitis is seen as swelling, heat, pain and induration in the mammary gland often resulting in deformation of the udder. In many cases the diagnosis of subclinical infections has come to depend largely on indirect tests which depend on the leukocyte content of the milk or somatic cell count (SCC). The most common organisms that infect the udder are classified into two groups: 1) contagious pathogens and 2) environmental pathogens. Examples of contagious pathogens include, for instance, *Staphylococcus aureus* and *Streptococcus agalactiae*. Examples of environmental pathogens include the coliforms such as, *Escherichia coli, Klebsiella pneumoniae, Klebsiella oxytoca, Enterococcus faecium, Enterococcus faecalis, Enterobacter aerogenes*, and Streptococci such as *S. uberis, S. bovis* and *S. dysgalactiae*. Examples of other gram negative bacteria which may cause mastitis include, *Aerobacter* spp., *Bacteroides* spp., *Campylobacter* spp., *Citrobacter* spp., *Enterobacter* spp., *Erwinia* spp., *Escherichia* spp., *Fusobacaterium* spp., *Klebsiella* spp., *Leptospira* spp., *Mycoplasma* spp., *Pasteurella* spp., *Providencia* spp., *Pseudomonas* spp., *Proteus* spp., *Serratia* spp., *Salmonella* spp., and *Yersinia* spp. Preferably, administration of the composition of the present invention will treat mastitis caused by a gram negative microbe or a gram positive microbe. Preferably, mastitis-causing gram positive microbes that can be treated using the present invention are members of the family Micrococcaceae, members of the family Deinococcaceae, or other gram positive microbes as described in the section "Compositions." More preferably, gram positive microbes are *Staphylococcus aureus, Streptococcus agalactiae, Streptococcus uberis, Streptococcus bovis* and *Streptococcus dysgalatiae* and *Streptococcus equi*, most preferably, *Staphylococcus aureus*. Preferably, mastitis-causing gram negative microbes that can be treated using the present invention are enteropathogens, more preferably, members of the family Enterobacteriaceae, even more preferably, members of the Enterobacteriaceae tribes Escherichieae or Salmonelleae, as described in the section "Compositions." Most preferably, gram negative microbes are *Salmonella* spp. and *E. coli*.

In yet another aspect, the invention provides for treatment of metritis in an animal, preferably in cattle. The method includes administering an effective amount of the composition of the present invention to an animal having or at risk of having metritis, and determining whether at least one symptom of metritis is reduced. Metritis is an inflammation of the uterus after calving and is often caused by a retained placenta. Subclinical metritis in an animal is often indicative of decreased performance characteristics, including, for instance, lower milk production, decreased fertility and weight loss, of the animal.

In another aspect, the invention is directed to a method for treating high somatic cell counts in an animal's milk, preferably, a cow. The method includes administering an effective amount of the composition of the present invention to a milk producing animal having or at risk of having high somatic cell counts, and determining whether the somatic cell count in milk obtained from the animal contains reduced somatic cell counts compared to milk obtained from the animal before receiving the composition. In another aspect the invention is directed to a method for reducing somatic cell counts in an animal's milk. Surprisingly and unexpectedly, decreases in somatic cell counts in animals receiving SRPs and porins from *Salmonella* did not appear to be related to clinical disease caused by *Salmonella* (see results section of Example 7, and Example 8). Somatic cell count (SCC) is a commonly used measure of milk quality. Somatic cells include leucocytes of the animal, and are typically present at low levels in normal milk. High levels of somatic cells in milk, for instance, at least about 250,000 cells per milliliter of milk, preferably, at least about 400,000 cells per milliliter of milk, indicate reduced milk quality. High levels of somatic cells in milk may be indicative of infection (mastitis), but may also be unassociated with infection (see Example 8). SCC is monitored, typically by milk processing plants, using methods that are routine to the art. In one aspect, the invention is particularly advantageous for reducing somatic cell counts of milk produced by milk producing animals infected with a microbe from the families Acholeplasmataceae, Bacteroidaceae, Enterobacteriaceae, Leptospiraceae, Micrococcaceae, Mycoplasmataceae, Mycobacteriaceae, Neisseriaceae, Pasteurellaceae, Pseudomonadaceae, Spirochaetaceae, or Vibronaceae. Preferably, the SCC is reduced to, in increasing order of preference, less than about 750,000 cells/ml, less than about 600,000 cells/ml, less than about 400,000 cells/ml, most preferably, less than about 250,000 cells/ml. Gram positive microbes causing increased SCC that can be treated using the present method are members of the family Micrococcaceae, members of the family Deinococcaceae, or other gram positive microbes as described in the section entitled "Compositions." Preferably, gram positive microbes are *Staphylococcus aureus, Streptococcus agalactiae, Streptococcus uberis, Streptococcus bovis* and *Streptococcus dysgalatiae* and *Streptococcus equi*, most preferably, *Staphylococcus aureus*. Gram negative microbes causing increased SCC that can be treated using the present method are enteropathogens, more preferably, members of the family Enterobacteriaceae, even more preferably, members of the Enterobacteriaceae tribes Escherichieae or Salmonelleae, as described in the section entitled "Compositions." Most preferably, gram negative microbes to which the antibody specifically binds are *Salmonella* spp. and *E. coli*.

In another aspect, the invention is directed to treating low milk production by a milk producing animal, preferably, a cow. The method includes administering an effective amount of the composition of the present invention to a milk producing animal having or at risk of having a low milk production, and determining whether milk production by the animal is increased compared to milk production by the animal before receiving the composition. In another aspect the invention is directed to a method for increasing milk production in a milk producing animal, preferably, a cow. The method includes administering a composition of the present invention to a milk producing animal, and determining whether milk production by the animal is increased compared to milk production by the animal before receiving the composition. Preferably, the milk production by a milk producing animal after administration of composition of the present invention is increased by at least about 1%, more preferably, by at least about 3%, most preferably, by at least about 6%. Preferably, milk production by a cow is determined before administration and about 2 weeks, more preferably, about 8 weeks, most preferably, about 16 weeks after administration of the composition.

In yet another aspect, the invention is directed to treating intestinal colonization by a microbe, preferably, an enteropathogen. Intestinal colonization by an enteropathogen is typically determined by measuring fecal shedding of a microbe by the animal. The method for treating intestinal colonization by an enteropathogen includes administering an effective amount of the composition of the present invention to an animal having or at risk of having fecal shedding of an enteropathogen, and determining whether the fecal shedding of an enteropathogen is decreased compared to the fecal shedding of the microbe by the animal before receiving the composition. Fecal shedding may be measured by methods routine and known to the art. Many of the animals infected with an enteropathogen, for instance, *Salmonella* spp or *E. coli*, will shed the microbe in their feces or body excretions. When the microbe is *Salmonella*, this may serve as a source for chronic Salmonellosis in the herd. Preferably, the microbe is *E. coli* or a *Salmonella* spp., more preferably, a *Salmonella* spp. Preferably, the microbe includes a polypeptide (for instance, an SRP and/or a porin) that include an epitope that is structurally related to an epitope present on an SRP and/or a porin present in the composition administered to the animal. Preferably, the level of fecal shedding is reduced by about 10-fold, more preferably, by about 100-fold, even more preferably, by about 1.000-fold. Most preferably, the level of fecal shedding of an enteropathogen is reduced such that the enteropathogen is no longer detectable.

The present invention is also directed to methods of increasing milk quality. Indicators of low milk quality include, for instance, somatic cell counts of at least about 250,000 cells per milliliter of milk, preferably, at least about 400,000 cells per milliliter of milk, and microbial contamination of milk. The method includes administering an effective amount of the composition of the present invention to an animal, and determining whether the quality of milk from a milk producing animal is increased compared to the milk quality of the milk producing animal before receiving the composition. Without intending to be limited by theory, milk produced by these animal results in the presence of antibody directed to SRPs and porins in the milk, and these antibodies will decrease the ability of microbes having cross-reactive SRPs and/or cross-reactive porins to grow in the milk.

A composition of the invention can be used to provide for active or passive immunization against bacterial infection. Generally, the composition can be administered to an animal to provide active immunization. However, the composition can also be used to induce production of immune products, such as antibodies, which can be collected from the producing animal and administered to another animal to provide passive immunity. Immune components, such as antibodies, can be collected to prepare antibody compositions from serum, plasma, blood, colostrum, etc. for passive immunization therapies. Antibody compositions comprising monoclonal antibodies and/or anti-idiotypes can also be prepared using known methods. Passive antibody compositions and fragments thereof, e.g., scFv, Fab, F(ab')$_2$ or Fv or other modified forms thereof, may be administered to a recipient in the form of serum, plasma, blood, colostrum, and the like. However, the antibodies may also be isolated from serum, plasma, blood, colostrum, and the like, using known methods and spray dried or lyophilized for later use in a concentrated or reconstituted form. Passive immunizing preparations may be particularly advantageous for treatment of acute systemic illness, or passive immunization of young animals that failed to receive adequate levels of passive immunity through maternal colostrum.

Another aspect of the present invention provides methods for detecting antibody that specifically binds polypeptides of the compositions of the present invention. These methods are useful in, for instance, detecting whether an animal has antibody that specifically bind polypeptides of the compositions of the present invention, and diagnosing whether an animal may have a condition caused by a microbe expressing SRPs and/or porins of the compositions described herein. Preferably, such diagnostic systems are in kit form. The methods include contacting an antibody with a preparation that includes polypeptides present in a composition of the present invention to result in a mixture. Preferably, the antibody is present in a biological sample, more preferably blood, milk, or colostrum. The method further includes incubating the mixture under conditions to allow the antibody to specifically bind the polypeptide to form a polypeptide:antibody complex. As used herein, the term "polypeptide:antibody complex" refers to the complex that results when an antibody specifically binds to a polypeptide. The preparation that includes the polypeptides present in a composition of the present invention may also include reagents, for instance a buffer, that provide conditions appropriate for the formation of the polypeptide:antibody complex. The polypeptide:antibody complex is then detected. The detection of antibodies is known in the art and can include, for instance, immunofluorescence and peroxidase.

The methods for detecting the presence of antibodies that specifically bind to polypeptides of the compositions of the present invention can be used in various formats that have been used to detect antibody, including radioimmunoassay and enzyme-linked immunosorbent assay.

The present invention also provides a kit for detecting antibody that specifically binds polypeptides of the compositions of the present invention. The kit includes at least two SRPs and at least two porins in a suitable packaging material in an amount sufficient for at least one assay. Optionally, other reagents such as buffers and solutions needed to practice the invention are also included. Instructions for use of the packaged polypeptides are also typically included.

As used herein, the phrase "packaging material" refers to one or more physical structures used to house the contents of the kit. The packaging material is constructed by well known methods, preferably to provide a sterile, contaminant-free environment. The packaging material has a label which indicates that the polypeptides can be used for detecting SRPs and/or porins. In addition, the packaging material contains instructions indicating how the materials within the kit are employed to detect SRPs and porins. As used herein, the term "package" refers to a solid matrix or material such as glass, plastic, paper, foil, and the like, capable of holding within fixed limits the polypeptides. Thus, for example, a package can be a microtiter plate well to which microgram quantities of polypeptides have been affixed. "Instructions for use" typically include a tangible expression describing the reagent concentration or at least one assay method parameter, such as the relative amounts of reagent and sample to be admixed, maintenance time periods for reagent/sample admixtures, temperature, buffer conditions, and the like.

The present invention is illustrated by the following examples. It is to be understood that the particular examples, materials, amounts, and procedures are to be interpreted broadly in accordance with the scope and spirit of the invention as set forth herein.

EXAMPLES

Compositions including siderophore receptor proteins and porins from *Salmonella* was evaluated for efficacy against a virulent challenge in mice and for the control of Salmonellosis in commercial dairy and feed lot cattle The efficacy of the composition was evaluated by collecting data on the following parameters: first the potency of the immunizing composition was evaluated against a live virulent challenge in mice, and secondly the efficacy was evaluated in commercial dairy and feed lot cattle by examining the serological response to vaccination, elimination of *Salmonella* as examined by fecal shedding, reduction in morbidity and mortality, reduction of somatic cells in milk, total milk production, and examination of injections sites after each vaccination.

Example 1

Production and Isolation of Siderophore Receptor Proteins and Porins

Gram negative bacteria belonging to the families Enterobacteriaceae and Pseudomonadaceae, as well as other gram negative bacteria can be grown under controlled fermentation conditions so as to express siderophore receptor proteins and porins, and optionally, iron regulated proteins, on the outer membrane. The bacteria can be harvested by conventional methods and the outer membrane proteins can then be isolated and used as immunogens in a vaccine composition described in detail in the following example.

*Salmonella dublin* was isolated from Holstein steers in a commercial feed lot showing clinical signs of Salmonellosis, and designated MS010207. The isolate was serotyped by the Minnesota Poultry Testing Laboratory, (Willmar, Minn.). A master seed stock of the organism was prepared by inoculating 100 ml of Tryptic Soy Broth (DIFCO Laboratories, Detroit, Mich.) containing 50 micrograms per milliliter (µg/ml) of 2,2-dipyridyl (Sigma-Aldrich St. Louis, Mo.). The culture was grown while stirring at 200 rpm for 6 hours at 37° C. The bacteria were collected by centrifugation at 10,000×g. The bacterial pellet was resuspended in 20 ml physiological saline (0.85%) containing 20% glycerol. The bacterial suspension was sterilely dispensed into 20-2 ml cryogenic vials and stored at −90° C. The master seed was expanded into a working seed that was then used for the production of siderophore receptor proteins and porins. A large-scale production process was developed involving fermentation, bacterial harvest, disruption, solubilization, concentration, diafiltration, and isolation of final product.

Fermentation

A cryogenic vial of the working seed (1 ml at $10^9$ CFU/ml) was used to inoculate 500 ml of Tryptic Soy Broth (TSB) without dextrose (DIFCO) pre-warmed to 37° C. containing 50 micrograms 2,2-dipyridyl (Sigma), 2.7 grams BI TEK yeast extract (DIFCO) and glycerol (3% vol/vol). The culture was incubated at 37° C. for 12 hours while stirring at 200 rpm at which time was inoculated into 2 liters of the above media and allowed to grow for an additional 4 hours at 37° C. This culture was used to inoculate a 20-liter VIRTIS bench-top fermentor, (VIRTIS, Gardiner, N.Y.) charged with 13 liters of the above-described media. The pH was held constant between 6.9 and 7.1 by automatic titration with 30% NaOH and 10% HCL. The stirring speed was adjusted at 400 rev/ minute, and the culture aerated with 11 liters air/minute at 37° C. Foaming was controlled automatically by the addition of 11 ml defoamer (MAZU DF 204 Chem/Serv, Minneapolis, Minn.). The culture was allowed to grow continuously at these conditions for 4 hours at which time was sterilely pumped into a 150-liter fermentor (W. B. Moore, Easton, Pa.). The fermentor was charged with 115 liters tryptic soy broth without dextrose (3,750.0 grams), BI TEK yeast extract (625 grams), glycerol (3750 ml), 2,2-dypyrdyl (3.13 grams) and MAZU DF 204 defoamer (100 ml). The parameters of the fermentation were as follows: dissolved oxygen (DO) was maintained at 30%+/−10% by increasing agitation to 220 rev/minute sparged with 60 liters of air/minute and 10 pounds per square inch (psi) back pressure. The pH was held constant between 6.9 and 7.1 by automatic titration with 30% NaOH and 10% HCL. The temperature was maintained at 37° C. At hour 4.5 ($OD_{540}$ 8-9) of the fermentation the culture was supplemented with additional nutrients by feeding 7 liters of media containing 1,875 grams TSB without dextrose, 313 grams yeast extract 3.13 grams 2,2-dipyridyl and 1,875 ml of glycerol. The rate of feed was adjusted to 29 ml/minute while increasing agitation to 675 rpm. At the end of the feed (hour 8.5) the fermentation was allowed to continue for an additional three hours at which point the fermentation was terminated by lowing the temperature of the fermentor to 10° C. ($OD_{540}$ 35-40 at a 1:100 dilution). The culture was sterilely transferred to a 200-liter tank (LEE Process Systems and Equipment model 2000LDBT) in preparation for harvest.

Harvest

The bacterial fermentation was concentrated and washed using a PALL FILTRON Tangential Flow Maxiset-25 (PALL FILTRON Corporation, Northboro, Mass.) equipped with two 30 $ft^2$ Alpha 300-K open channel filters, catalog No. AS30005, PALL FILTRON) connected to a Waukesha Model U-60 feed pump (Waukesha Chemy-Burrell, Delevan, Wis.) The original culture volume of 125 liters was reduced to 25 liters (2.5 liters/minute) using a filter inlet pressure of 15 psi and a retentate pressure of 0 psi. The bacterial retentate was adjusted back up to 50 liters using physiological saline (0.85%) and then concentrated again to 15 liters to help remove any contaminating exogenous proteins, etc. The retentate (15 liters) was adjusted to 35 liters using sterile Osmotic Shock Buffer (OMS) containing 7.26 grams/liter Tris-base and 0.93 grams/liter EDTA adjusted to a pH of 8.5. The EDTA in the OMS serves to remove much of LPS from the cell wall, while the elevated pH prevents much of the proteolytic degradation after freezing and disruption. Protease inhibitors may be used instead of, or in addition to, an elevated pH. The retentate was mixed thoroughly while in the 200-liter tank using a bottom mount magnetically driven mixer. The retentate was sterilely dispensed (3.5 liters) into sterile 4 liter NALGENE containers No. 2122 and placed into a −20° C. freezer for storage. Freezing the bacterial pellet serves to weaken the cell wall structure making downstream disruption more efficient. The pellet mass was calculated by centrifuging 30 ml samples of the fermented culture and final harvest. Briefly, pre-weighted 50 ml NALGENE conical tubes were centrifuged at 39,000×g for 90 minutes in a Beckman J2-21 centrifuge using a JA-21 rotor (Beckman Instruments, Palo Alto Calif.). At the end of the run, the supernate was poured off and the tubes were weighed again. The pellet mass was calculated for each stage. The fermentation process yielded a wet pellet mass of 9.0 kilograms.

Disruption (Homogenization)

Twenty kilograms of frozen bacterial cell slurry in OMS were thawed at 4° C. (20 kg of pellet mass). The liquid culture suspension from each container was aseptically aspirated into a steam in place 250 liter jacketed process tank (LEE, Model 259LU) with a top mounted mixer (Eastern, Model TME-1/2, EMI Incorporated, Clinton, Conn.) containing 222 liters OMS pH 8.5 containing 0.1 grams thimerosal/liter as preservative. The volume of OMS was determined by dividing the pellet mass (in grams) by 900 and then multiplying the result by 10 to get the homogenizing volume in liters (gram pellet mass/900×10=liters homogenizing volume). The bulk bacterial suspension was chilled to 4° C. with continuous mixing for 18 hours at 200 rpm at which time was disrupted by homogenization. Briefly, the 250 liter tank containing the bacterial suspension was connected to a model 12.51 H RANNIE Homogenizer, (APV Systems, Rosemont, Ill.). A second 250 liter jacketed process tank (empty) was connected to the homogenizer such that the fluid in the process tank could be passed through the homogenizer, into the empty tank and back again, allowing for multiple homogenizing passes while still maintaining a closed system. The temperature during homogenization was kept at 4° C. At the start of each pass, fluid was circulated at 70 psi via a Waukesha model 10DO pump (Waukesha) through the homogenizer (160 gallons/hour) and back to the tank of origin, while the homogenizer pressure was adjusted to 13,500 psi. Prior to the first pass, two pre-homogenizing samples were withdrawn from the homogenizer to establish a baseline for determining the degree of disruption and monitoring of pH. The degree of disruption was monitored by transmittance (% T at 540 nm at 1:100 dilution) compared to the non-homogenized sample. The number of passes through the homogenizer was standardized for different organisms based on the integrity of the cell wall and variation in the degree of disruption, which had a direct correlation in the efficiency of solubilization and quality of end product. For example, the disruption of *Salmonella* passed three times through the homogenizer gave a final percent transmittance between 78-83% T at a 1:100 dilution. *E. coli* having the same pellet mass and starting OD gave a % T of 86-91% (at a 1:100 dilution) after the third pass. It has been observed that bacteria differ in their cell wall integrity and vary in their capacity of disruption under identical condition. This variation can effect the degree and efficiency of solubilization and recovery of SRPs and porins from the outer membrane. In general, cells were passed through the homoginizer until the transmittance did not increase after an additional pass.

After homogenization, Sodium Lauroyl Sarcosinate (HAMPOSYL L-30, Chem/Serv) was aseptically added to the homogenized bacterial suspension for solubilization. The amount of Sarcosine (30%) added equaled 0.0664 times the solubilizing volume, in liters, (1.0 gram sarcosine/4.5 grams pellet mass). The tank was removed from the homogenizer and put onto a chiller loop at 4° C. and mixed at 240 rpm for 60-70 hours. This time period was important for complete solubilization. It was discovered that increasing the solubilization time in OMS at an elevated pH (8.0-8.5) that the SRN and porins aggregated together forming large insoluble aggregates that were easily removed by centrifugation. The optimal OD after solubilization was usually between 25-30% T at 540 nm.

Protein Harvest

The aggregated siderophore receptor proteins and porins within the solubilized process fluid were collected by centrifugation using T-1 Sharples SHARPLES, (ALFA LAVAL Separations, Warminster, Pa.). Briefly, the tank of solubilized homogenate was fed into six SHARPLES with a feed rate of 250 ml/minute at 17 psi at a centrifugal force of 46,000×g. The effluent was collected into a second 250 liter jacketed process tank through a closed sterile loop allowing for multiple passes through the centrifuges while maintaining a closed system. The temperature during centrifugation was kept at 4° C. The solubilized homogenate was passed 8 times across the centrifuges. Fifty percent of the protein was collected after the second pass, at which point, the solubilized fluid was concentrated to ⅓ of its original volume, which shortened the process time for the next 6 passes. Briefly, the solubilized homogenate tank was aseptically disconnected from the centrifuges and connected to a MILLIPORE PELLICON Tangential Flow Filter assembly (Millipore Corporation, Bedford, Mass.), equipped with a 25ft$^2$ screen-channel series Alpha 10K CENTRASETTE filter (Pall Filtron) connected to a Waukesha Model U30 feed pump for concentration. After concentration, centrifugation was continued until the process was completed. Protein was collected after each pass. The protein was collected, resuspended and dispensed in 50 liters Tris-buffer pH 8.5 containing 0.3% formulin (SIGMA) as preservative.

Diafiltration

The protein suspension was washed by diafiltration at 4° C. to remove any contaminating sarcosine that may be bound to the protein. Briefly, the 50 liters of protein was sterilely aspirated into a 200 liter process tank containing 50 liters sterile Tris-buffer, pH 8.5 equipped with a bottom mount Dayton mixer, Model 2Z846 (DAYTON ELECTRIC, Chicago, Ill.) rotating at 125 rev/minute. The process tank was sterilely connected to a MILLIPORE PELLICON Tangential Flow Filter assembly (Millipore Corporation), equipped with a 25 ft$^2$ screen-channel series Alpha 10K CENTRASETTE filter (PALL FILTRON) connected to a Waukesha Model U30 feed pump. The 100 liter protein solution was concentrated by filtration to a target volume of 5.45 times the protein pellet mass at which point Tris-buffer pH 7.4 containing 5% isopropyl alcohol was slowly added to the concentrate from a second process tank. Isopropyl alcohol causes a slight unfolding of the protein structure allowing for the removal of bound sarcosine without compromising the immunogenicity of the protein. Diafiltration continued until the pH stabilized to 7.4 at which point 50 liters Tris-buffer pH 7.4 was slowly added by diafiltration to remove residual alcohol. The protein suspension was then concentrated to approximately 25 liters. The protein concentrate was aseptically dispensed (3.5 liters) into sterile 4 liter NALGENE containers and placed into a −20° C. freezer for storage.

This process produces an extremely pure composition of SRPs and porins with almost the complete removal of LPS with very little to no sarcosine residue. The protein was examined by SDS-PAGE for purity and banding profile, bacterial contamination, residual sarcosine and LPS. The banding profile of the finished product showed consistent patterns as examined by electrophoresis. The composition was tested for sarcosine by the use of a modified agar gel diffusion test in which sheep red blood cells (5%) were incorporated into an agar base (1.5%). Wells were cut into the agar and samples of the finished product along with control samples of known concentrations of sarcosine at 0.05, 0.1, 0.2, 0.3, 0.4, 0.5. 1.0 and 2.0% were placed into the wells. The gel was incubated at 25° C. for 24 hours and the degree of hemolysis was determined compared to the controls. The process removes the level of detectable sarcosine below 0.05%, which at this concentration showed minimal hemolysis in control samples.

LPS was removed below the detection level as examined by a *Limulus* amebocyte lysate (LAL) test available under the tradename E-TOXATE (Sigma Chemical Co., St. Louis, Mo.).

Example 2

Mouse Vaccination and Challenge Study

The efficacy of a *Salmonella dublin* vaccine consisting of Siderophore receptor proteins (SRPs) and porins was carried out against a live virulent challenge in mice as described under 9 CFR 13.123. Sixty female CF-1 mice obtained from Harlan Breeding Laboratories (Indianapolis, Ind.) weighing 16-22 grams were equally distributed into 6 polycarbonate mouse cages (Ancore Corporation, Bellmore, N.Y.) designated as groups 1-6.

The composition including siderophore receptor proteins and porins was prepared as described in Example 1 from a bovine field isolate of *Salmonella dublin* originating from a herd of Holstein Dairy cows showing clinical symptoms of Salmonellosis.

The SRPs had molecular weights of 89 kDa, 84 kDa, 72 kDa and porins had molecular weights of 38-39 kDa as examined on a 12% SDS-Page gel. The SRPs and porins in 8.3 ml (6,035 g/ml) were resuspended into 69.2 ml physiological saline (0.85%). The aqueous protein suspension (77.5 ml) was emulsified into 22.5 ml EMULSIGEN, (MVP Laboratories, Ralston, Nebr.) using a IKA ULTRA TURRAX T-50 homogenizing vessel (IKA, Cincinnati, Ohio) to give a final dose of 125 μg total protein in a 0.25 ml injectable volume at a 22.5% vol/vol adjuvant concentration. The mouse dose was adjusted to be equivalent to a field dose of 1,000 μg at a 2 ml volume.

The potency of the vaccine was tested at four different concentrations, non-diluted (Group-1), 1:10 (volume diluent: volume protein solution) (Group-2), 1:100 (Group-3), and 1:1000 (Group-4) compared to two control groups; a non-vaccinated challenged group (Group-5) and a non-vaccinated non-challenged group (Group-6). EMULISIGEN was used as the diluent for diluting the stock vaccine at a 22.5% concentration prepared in physiological saline: Mice were vaccinated intraperitoneally and revaccinated 14 days after the first vaccination. The volume administered was 0.25 cc.

Fourteen days after the second vaccination, mice in groups 1-5 were intraperitoneally challenged with $1.7 \times 10^8$ colony forming units (CFU) of a virulent *Salmonella dublin* isolate. The isolate (IRP SCC Serial) was obtained from The Center of Veterinary Biologics-Laboratory, United States Department of Agriculture, Ames, Iowa. Mortality was recorded daily for 2 weeks post-challenge. Table 1 below shows the mortality between the vaccinated and non-vaccinated mice following challenge.

TABLE 1

Mortality of Vaccinated and Non-Vaccinated Mice Following Challenge with *Salmonella dublin*

| Groups | # Mice | # Dead | Percent mortality (%) |
|---|---|---|---|
| Group-1 (non-diluted) | 10 | 0/10 | 0 |
| Group-2 (1:10) | 10 | 1/10 | 10 |
| Group-3 (1:100) | 10 | 3/10 | 50 |
| Group-4 (1:1000) | 10 | 5/10 | 60 |
| Group-5 (non-vaccinated/challenged | 10 | 10/10 | 100 |
| Group-6 (non-vaccinated/non-challenged | 10 | 0/10 | 0 |

Ten (100%) of the non-vaccinated mice (Group-5) died within 14 days after challenge (Table 1). In contrast, none of the mice died given the non-diluted vaccine of group 1. All dilutions of the test vaccine showed a high degree of protection as compared to the non-vaccinated/challenged mice of group-5. None of the mice died in group-6 showing no horizontal transmission of the organism between groups.

Example 3

Preparation of an Immunizing Composition Derived from *Salmonella bredeney*

*Salmonella bredeney* was isolated and serotyped from a Minnesota dairy herd having a history of high adult and calf mortality, morbidity and loss of production due to this bacterial strain, and designated MS010914. SRPs and porins were isolated as described in Example 1. Three high molecular weight SRPs, 89 kDa, 84 kDa, and 72 kDa, were observed on a 12% sodium dodecyl sulfate polyacrylamide gel electrophoresis (SDS-Page) gel. Three additional lower molecular weight iron-regulated proteins (IRPs) were also isolated at approximately the 37 kDa, 32 kDa and 29 kDa regions. Porins having a molecular weight in the range of 38-39 kDa were also purified from the propagated isolates.

Two compositions were prepared from the SRPs having molecular weights of 89 kDa, 84 kDa, and 72 kDa, the IRPs having molecular weights of 37 kDa, 32 kDa, and 29 kDa, and porins having molecular weights of 38-39 kDa. The target proteins were emulsified in the following vaccine formulations to provide a total dose of about 1,000 µg. In the first composition, referred to as Vac-1, 50 ml of antigen (4.35 milligram/milliliter (mg/ml)) was slowly added while stirring to 40 ml of 25% aluminum hydroxide (REHYDRAGEL-HPA, Reheis, N.J.) prepared in 270 ml physiological saline. The antigen/aluminum hydroxide suspension was stirred for 24 hours at 4° C. The antigen/aluminum hydroxide suspension was then emulsified into 40 ml of EMULSIGEN, to give a final dose of 1,000 µg total protein in a 2 ml injectable volume.

In the second composition, referred to as Vac-2, 217.25 mg of the SRP antigen was mixed into 270 ml of physiological saline. The antigen solution was emulsified into 80 ml of EMULSIGEN to give a final dose of 1,000 µg total protein in a 2 ml injectable volume.

Example 4

Pre-Testing of the Immunizing Compositions

To determine any possible side effects (e.g. reduced milk production, adverse tissue reaction, etc.), the vaccines of Example 3 were first administered to cattle from various stages of production: 2 lactating cows, 2 non-lactating adult cows, and 2 calves. Two days prior to pre-testing, two lactating cows were selected to determine their daily milk production. Milk production from each cow was also monitored at each of the two daily milkings for two consecutive days (48 hours) after vaccination to determine any loss in production due to vaccination. Monitoring was repeated on a single milking from each cow on day 7. The two lactating cows received 2 mls of Vac-1 subcutaneously in the neck region. In addition, another 2 non-lactating cows were administered 2.0 ml of Vac-2 subcutaneously in the neck region and two calves were administered 1.0 ml of Vac-1 subcutaneously in the neck region and the animals monitored for 7 days for any adverse reaction.

No adverse tissue reactions were observed at any of the injection sites of the 6 animals given the pre-test vaccines. In addition, there was no measurable loss in milk production from the lactating cows at 2 and 7 days after vaccination.

Example 5

Herd Immunization

After completion of the study of Example 4, immunizing compositions of Vac-1 and Vac-2 were administered to the entire herd. The herd consisted of 55 lactating cows, 52 non-lactating cows and 18 calves ranging in age from 6 months to 12 months. Lactating cattle received 2.0 ml of Vac-1; non-lactating cattle received 2.0 ml of Vac-2; calves less than 12 months of age but older then 6 months received 1.0 ml of Vac-1; and calves greater then 12 months of age received 1.0 ml of Vac-2 (see Table 2). All injections were delivered subcutaneously in the neck region.

TABLE 2

Schedule of events.

| STUDY DAY | DESCRIPTION OF EVENTS |
|---|---|
| Pre-testing | Vaccinated 2 lactating cows, 2 non-lactating cows and 2 calves. Monitored milk production and adverse reactions. |
| First vaccination Day 0 | Vaccinated all lactating and non-lactating cows (2 ml) except for calves, under 12 months, gave 1 ml and 2 ml if older then 12 months. Collected blood and fecal samples from lactating cows. |
| Week 3 | Collected blood and fecal samples from lactating cows, examined injection sites. |
| Second vaccination Week 5 | Vaccinated all lactating and non-lactating cows (2 ml) except for the calves, under 12 months, gave 1 ml and 2 ml if older then 12 months. |
| Week 7 | Collected blood, fecal samples and examine injection sites. |
| Week 11 | Collected blood, fecal samples and examine injection sites. |
| Third vaccination Week 19 | Vaccinated all lactating and non-lactating cows (2 ml) except for the calves, under 12 months, gave 1 ml and 2 ml if older then 12 months. |
| Week 21 | Collected blood, fecal samples and examine injection sites. |
| Week 35 | Collected blood and fecal samples |
| Week 44 | Collected blood and fecal samples |

Thirty five days after the first vaccination all animals were administered a second dose (booster) subcutaneously in the neck. For the booster dose, all lactating cows received 2.0 ml of Vac-1, non-lactating cows received 2 ml Vac-2, calves between 6-12 months of age received 1.0 ml of Vac-1, and animals 12 months of age or older received 1.0 ml of Vac-2. The schedule of events is shown in Table 2.

Based on the lack of reaction and observed safety of the immunizing compositions, the herd was vaccinated a third time, 19 weeks after the first vaccination (Table 1). The target proteins were emulsified into a single formulation used in all cows, referred to here as Vac-3. Briefly, 300 mg antigen (SRP and porins) was mixed into 250.96 ml of physiological saline. The antigen solution was emulsified into 80 ml of EMULSIGEN to give a final dose of 1,000 µg total protein at a 22.5% EMULSIGEN concentration in a 2 ml injectable volume. All lactating and non-lactating cows received a 2 ml intramuscular injection while calves 6 months of age and older received a 1 ml intramuscular injection.

Example 6

Blood and Fecal Sample Collection and Somatic Cell Counts

Blood samples were collected from twenty lactating cows on the initial day of immunization (day 0) and again at 3, 7, 11, 21, 35 and 44 weeks after the initial immunization. In addition, fecal samples were taken from all lactating cows on the day of immunization (day 0) and again at 3, 7, 11, 21, 35 and 44-weeks after immunization (Table 2).

All blood was collected in sterile 13×75 millimeter (mm) vacutainer collection tubes, brand SST No. 369783, (Becton Dickinson, Franklin Lakes, N.J.). After clotting, the blood tubes were centrifuged at 800×g for 30 minutes and frozen at −20° C. until analysis.

Individual fecal samples were taken aseptically by rectal extraction using sterile shoulder length gloves and placed in sterile whirl pack bags. Ten grams of feces from each sample was placed into 90 ml of Tetrathionate broth (DIFCO) and incubated at 37° C. for 24 hours. Each sample was plated onto Bismuth sulfite, Brilliant green and XLD agar (DIFCO) as a differential selective media to identify the presence of *Salmonella*. All suspect isolates were confirmed to be *Salmonella* using *Salmonella* O antiserum (poly A-I and Vi) with a slide agglutination test. Briefly, a colony is removed from a plate and mixed in a drop of poly O antiserum. This is mixed for about 30 seconds if it agglutinates it's a confirmed suspect. Confirmed *Salmonella* isolates were sent to the Minnesota Poultry Testing Laboratory (MPTL), Willmar, Minn., for serotyping.

Somatic cell counts were per milliliter of milk were conducted by the Dairy Herd Improvement Association (DHIA, Buffalo, Minn.) using standard methods. The somatic cells counted were the white blood cells present in the milk.

Example 7

Enzyme-Linked Immunosorbent Assay (ELISA)

An Enzyme-Linked Immunosorbent Assay (ELISA) monitored the serological response to the vaccine. The highly conserved SRPs from *Salmonella bredeney* having molecular weights of 89 kDa, 84 kDa, and 72 kDa were purified from polyacrylamide gels. Briefly, the corresponding SRP bands (89 kDa, 84 kDa, and 72 kDa) were cut from unstained gels using a stained indicator lane for determining band location which was cut away from the original gel and stained. Elution of the protein from the macerated gel was carried out according to the manufactures recommendation using a model 422 electro-eluter (BIO-RAD, Laboratories, Hercules, Calif.). These proteins were then used as the capture molecule in an indirect ELISA test.

Polyclonal antiserum was raised against the vaccine composition of example 4. Briefly, the vaccine composition consisting of SRPs and porins of *Salmonella bredeney* was inoculated subcutaneously into 2 adult Holstein heifers (2 ml dose at 1000 ug total protein). Each Heifer received a total of three vaccinations 21 days apart. Fourteen days after the third vaccination 20 ml of blood was collected from the tail vein of vaccinated cows. In addition negative control serum (20 ml) was obtained from two non-vaccinated cows. The hyperimmune and negative serum was obtained by centrifugation (800×g) of the clotted blood. The hyperimmune and control sera was absorbed with killed whole cell bacteria of *Salmonella bredeney* grown in iron-replete media (BHI containing 200 um ferric chloride) for 1 hour at 4° C.

Twenty milliliters of the positive and negative control sera was precipitated for 6 hours using ammonium sulfate (60% saturation), dissolved in 0.02 M phosphate buffer pH 7.0 at 4° C. The precipitate was collected by centrifugation at 8000×g for twenty minutes. The pellet was resuspended in 20 ml of 50 mM phosphate buffer pH 7.2 and dialyzed using a 100,000 MWCO dialysis tubing (Pierce, Rockford, Ill.) against 0.02 M pH 7.2. The dialyzed material was concentrated 10 times using a DIAFLO ultrafiltration apparatus model 8200 with a 50,000 MWCO membrane (AMICON). The positive and negative control dialysate was alquoted into 100 ul samples and frozen at −90° C.

The optimum working concentrations of SRP and conjugate was determined by several checkerboard titrations using the positive and negative control dialysates. A prediction curve was then established to calculate SRP ELISA titers at a 1:500 dilution. All subsequent tests were performed at a single serum dilution (1:500) and SRP titers were calculated from the average of duplicate test absorbance values.

The ELISA was performed by adding 100 ul of diluted SRP of *Salmonella* in 0.05 M carbonate buffer (pH 9.6) to each well of a 96-well flat bottom, easy wash microtiter plate (CORNING, Corning N.Y.). After overnight incubation at 4° C., excess SRP was removed and the plate was washed. All subsequent washing steps were done three times in phosphate buffered saline (pH 7.4) with 0.05% TWEEN-20. The plates were blocked for one hour at 37° C. with 4% fish gelatin (Sigma) in PBS and then washed.

Duplicate serum samples from Example 4 were tested in parallel at single-point dilutions using 100 ul/well and incubated for 45 minutes at 37° C. The first two rows of each plate contained the negative and positive control samples while the rest of the plate was used for the test samples. The plate was incubated for 45 minutes at 37° C. while stirring at 200 rpm. After washing, 100 ul alkaline phosphatase conjugate (Monoclonal anti-bovine IgG clone BG-18, SIGMA) at a 1:15,000 dilution was added to each well. After incubation for 45 minutes at 37° C., the plates were washed and 100 ul p-NitroPhenyl Phosphate (pNPP) substrate (SIGMA) was added to each well. The substrate was allowed to react for 2 hours at 37° C. while stirring at 100 rpm. The reaction was terminated by the addition of 25 ul of 3N NaOH. The absorbance was read at 405 nm.

Results of Examples 3-7

FIG. 1 shows the cumulative history of the shedding prevalence of *Salmonella* compared to the serological response to vaccination in lactating cows. As described in Example 5, the herd was vaccinated on the day of the initial immunization (Day 0) and again at 5 and 19 weeks after the first vaccination. Fecal and blood samples were taken from all lactating cows at 0, 3, 7, 11, 21, 35, and 44 weeks. Briefly, the immunizing compositions consisting of Vac-1 and Vac-2 were given to all cows (N=125) in the herd on the day of the initial immunization, day 0 (Table 1). Only the lactating cows were monitored through the experimental trial. All lactating cows were subcutaneously given 2 ml of Vac-1. The shedding prevalence of *Salmonella* in the fecal samples taken from the lactating cows (N=55) on day 0 revealed an isolation rate of 85.4% (FIG. 1). All of the *Salmonella* isolates were serotyped and found to be *S. bredeney*.

Within this same time period the somatic cell count as determined by DHIA was 1,492,000 cells per milliliter of milk (Table 3), the highest it had ever been in the history of the farm.

TABLE 3

The Somatic Cell Count (SCC)[1] of Individual Cows Before and After Vaccination

| SCC before/after vaccination[2] | | | | SCC before/after vaccination | | | |
|---|---|---|---|---|---|---|---|
| Cow ID | SCC × 1000 | Cow ID | SCC × 1000 | Cow ID | SCC × 1000 | Cow ID | SCC × 1000 |
| 1 | 1980/3930 | 14 | 570/680 | 27 | 970/160 | 40 | 40/50 |
| 2 | 9990/3870 | 15 | 63/520 | 28 | 1150/130 | 41 | 140/50 |
| 3 | 1230/3370 | 16 | 460/460 | 29 | 140/120 | 42 | 210/40 |
| 4 | 1240/2090 | 17 | 9990/450 | 30 | 50/120 | 43 | 70/40 |
| 5 | 4390/1980 | 18 | 3890/360 | 31 | 660/120 | 44 | 80/30 |
| 6 | 5510/1660 | 19 | 160/350 | 32 | 450/120 | 45 | 90/30 |
| 7 | 2090/1550 | 20 | 570/290 | 33 | 380/110 | 46 | 110/30 |
| 8 | 870/1170 | 21 | 7070/250 | 34 | 220/100 | 47 | 230/30 |
| 9 | 3020/960 | 22 | 210/240 | 35 | 350/100 | 48 | 3200/20 |
| 10 | 2620/950 | 23 | 230/220 | 36 | 70/90 | 49 | 20/20 |
| 11 | 1040/780 | 24 | 50/210 | 37 | 890/60 | 50 | 50/20 |
| 12 | 1330/720 | 25 | 190/190 | 38 | 700/60 | 51 | 40/10 |
| 13 | 120/720 | 26 | 540/180 | 39 | 100/50 | Average SCC | 1492/585 |

[1]Number of somatic cells per milliliter of milk.
[2]Samples taken before vaccination were taken in July (year 2, immediately before vaccination), and samples taken after vaccination (year 2) were taken in August (P = 0.0068).

Figure 2:
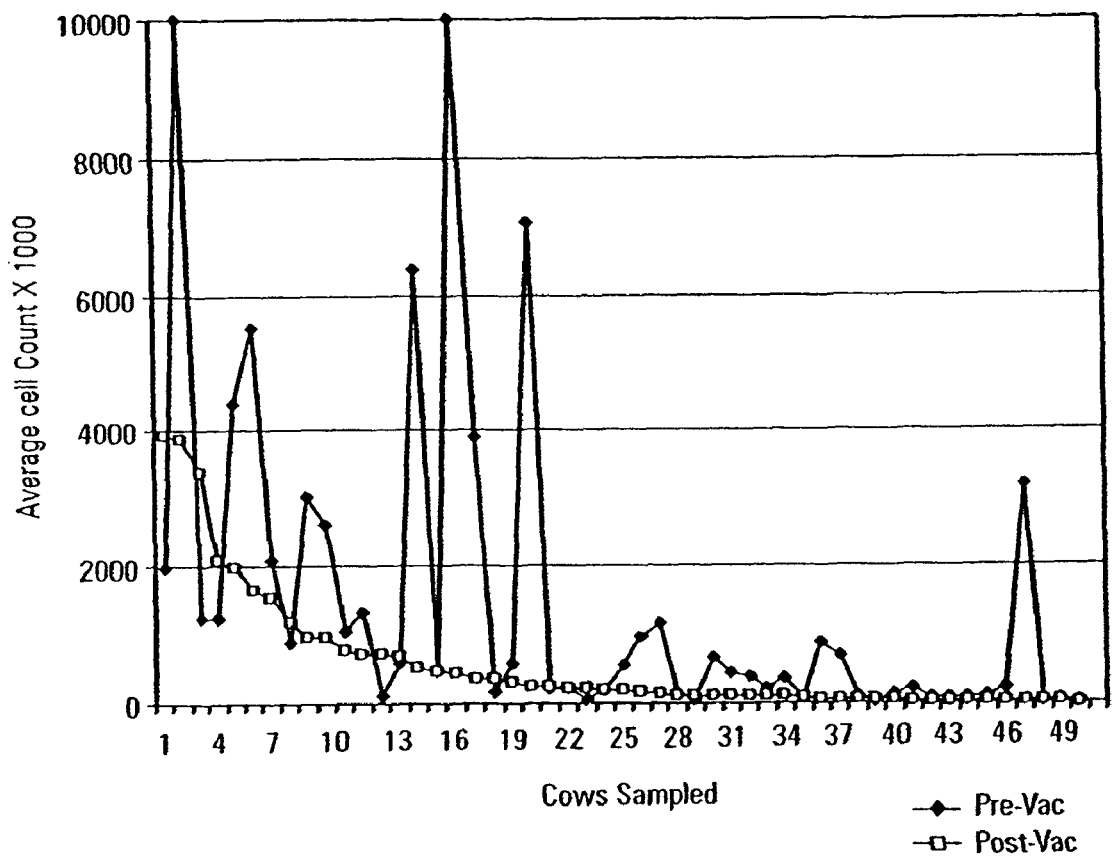
FIG. 2. The Dairy Herd Improvement Association (DHIA) somatic cell count on individual cows before and after the first vaccination. Average cell count×1,000, average somatic cell count times 1,000; Cows sampled, identification of each of the 51 cows; Pre-Vac, average cell count×1,000 of each cow before vaccination; Post-Vac, average cell count×1,000 of each cow before vaccination.

Three weeks after the first vaccination, fecal samples taken from all lactating cows (N=54) revealed no significant change in the shedding prevalence of Salmonella, which remained at 87%, (FIG. 1). Nevertheless, the somatic cell count dropped to 585,000 cells per milliliter. This is graphically and numerically depicted in FIG. 2 and table 3 which shows the DHIA somatic cell count on individual cows before and after the first vaccination. There was a 61.0% drop in somatic cell count having a degree of significance of P=0.0068 This highly significant affect was observed without improvements in management and/or environmental changes. One year after the first vaccination the cumulative 12 month average in somatic cell count was 417,000 cells per milliliter of milk. In contrast, the 12 month average before vaccination was 660,000 somatic cells per milliliter of milk. This was a 37% decrease in the somatic cells after vaccination. It is interesting to speculate that because of the conserved nature of these proteins it induced a degree of cross-protection against other gram negative or gram positive bacteria responsible for contagious and/or environmental mastitis.

The injection sites of all calves and lactating cows were examined 14 days after the first vaccination. None of the cows examined showed any adverse tissue reaction at the site of injection by physical examination. In addition, there was no measurable loss in milk production due to vaccination.

Five weeks after the first vaccination the herd was given a booster (Table 2). Fourteen-days after the second vaccination (Week 7) there was a 21.2% drop in the shedding prevalence of Salmonella with the total number of isolations being 35 out of 54 samples taken or, 64.8% of the herd positive for Salmonella in contrast to a previous prevalence of 86% (FIG. 1). The isolation rate continued to decline and by the eleventh week the shedding prevalence was 47.1% or 24 positive isolates out of 51 cows sampled. This was a 52.9% reduction in the number of positive Salmonella isolations. Physical examination of the injection sites showed no adverse tissue reaction in any of the calves and/or lactating cows examined. However, the second vaccination resulted in approximately a 2% drop in milk production that began 24 hours after vaccination but lasted less than two days. At this point the data showed the vaccine compositions to be highly tissue compatible with minimal loss in milk production. In addition, the data indicated a direct correlation between the declining shedding prevalence of Salmonella to the increasing SRP antibody response.

To stimulate a higher SRP antibody response the herd was vaccinated a third time, fourteen weeks after the second vaccination (Week 19, Table 2). The protein concentration of the vaccine remained the same (1000 µg/2 cc dose) but the adjuvant (EMULSIGEN) was increased to 22.5% vol/vol. Blood and fecal samples were taken 14-days after vaccination (Week 21, Table 2). The shedding prevalence of Salmonella declined to 45%, i.e., only 28 cows out of 61 sampled were positive for Salmonella (FIG. 1). All of these samples were serotyped and found to be Salmonella bredeney. At this same time period the injection sites of each lactating cow was examined, and less than 5% developed a granuloma that measured approximately 1 centimeter×1 centimeter. These granulomas resolved within 21 days after injection.

Figure 3:
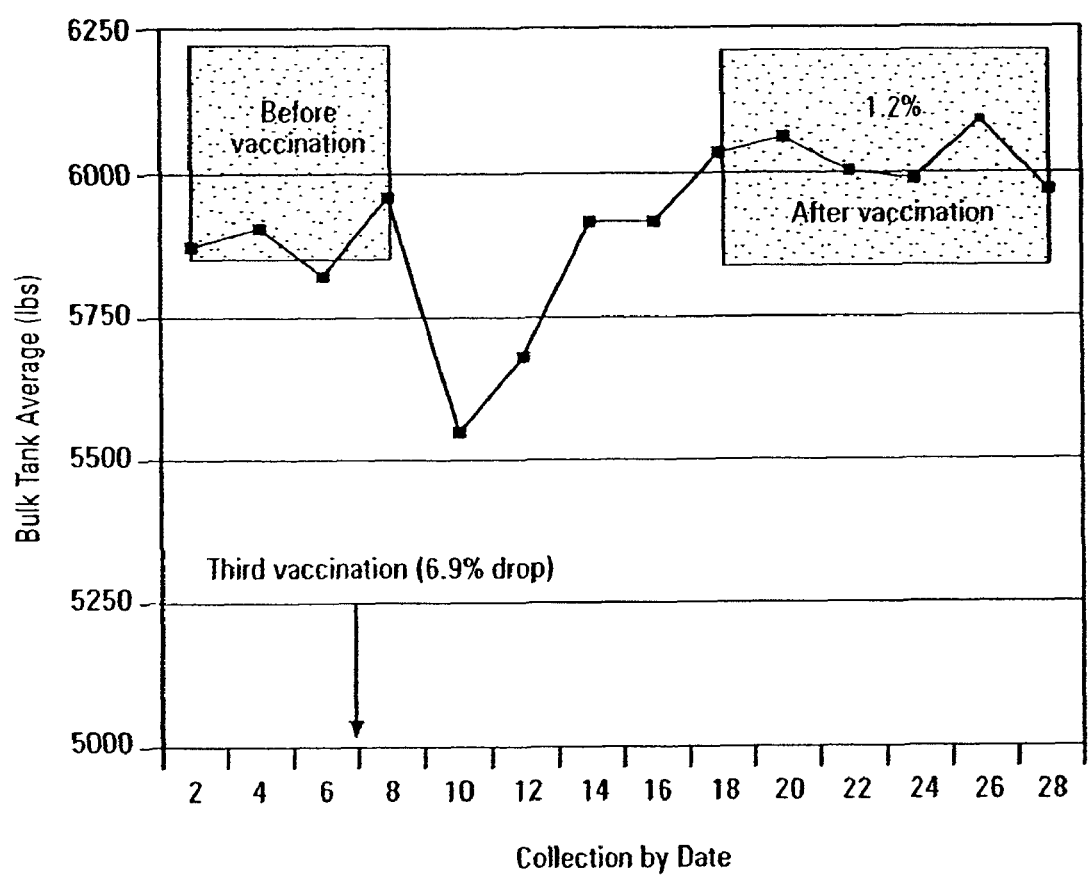
FIG. 3. Cumulative pounds of milk produced before and after the third vaccination. Bulk Tank Average (lbs), pounds of milk produced by all cows in lactation. The shaded areas "Before vaccination" and "1.2% After vaccination" represent the difference in percent in milk production before and after the third vaccination.
Figure 4:
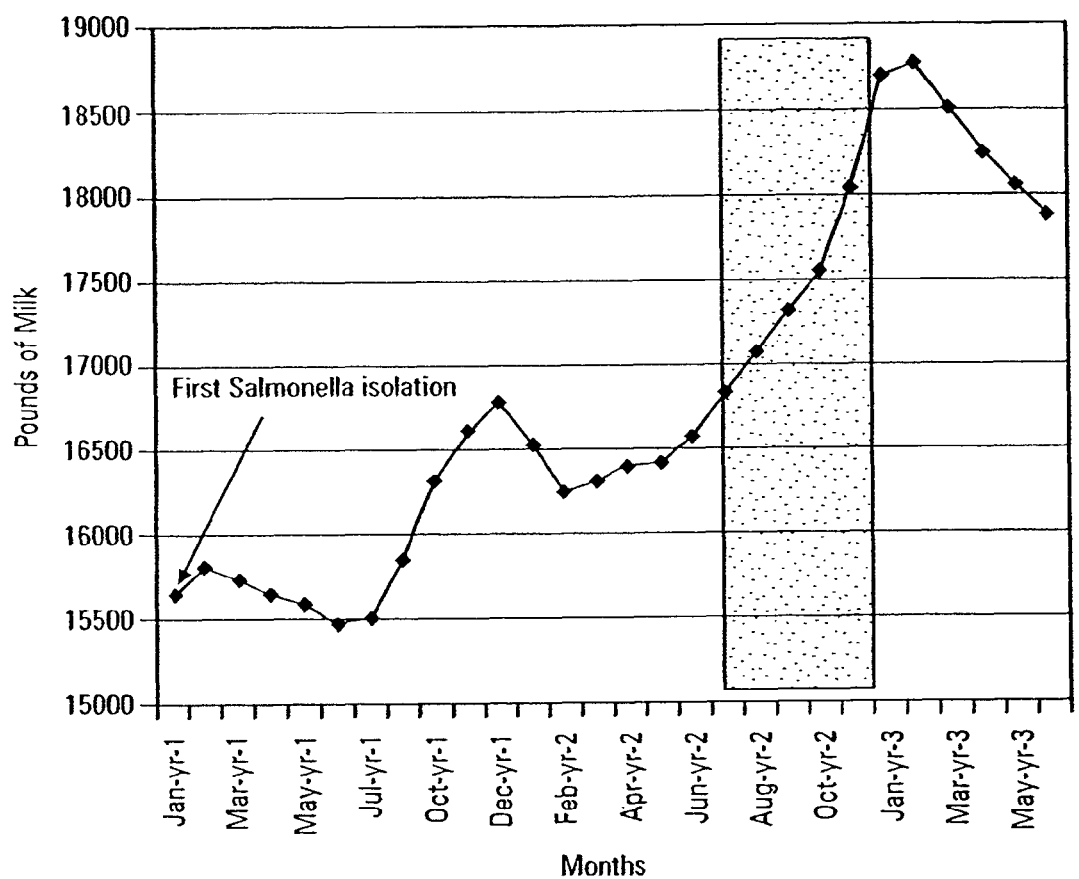
FIG. 4. The cumulative rolling herd average showing pounds of milk produced before and after vaccination in lactating cows. Pounds of milk, pounds of milk produced by all cows in lactation and averaged over the period of a month. Shaded area represents the rise in milk production during vaccination.

The cumulative pounds of milk produced before and after the third vaccination is shown in FIG. 3. After the third vaccination the drop in milk production peaked at 6.9%. This loss in production appeared transient within the herd, lasting less then four days, at which point the herd regained normal production. In fact, after the third vaccination the average milk production for the remainder of the month increased by 1.2% as compared to production before vaccination (FIG. 3). This increase in milk production was consistent and started at the beginning of the first vaccination. For example, the DHIA rolling herd average for 45 cows for the month of December (year 1, before vaccination) was 16,787 pounds of milk (FIG. 4 and Table 4). The general health and overall performance of the herd increased after each vaccination. Fourteen days after the third vaccination (December) the rolling herd average for 53 cows was 18,047 pounds of milk produced (FIG. 4 and Table 3). This was a 7.0% increase in milk per cow or and average of 1,260 pounds per year. In addition, the annual pounds of milk produced 1 year after vaccination was 965,472 pounds compared to 740,855 pounds produced before vaccination. This was a 6% increase in the total pounds of milk produced.

TABLE 4

The Annual Herd Summary From the Onset of the First *Salmonella* isolation
DHI Rolling Herd Average-Entire Herd

| Year Sampled (year 1) | | | | Year Sampled (year 2) | | | | Year Sampled (year 3) | | | |
|---|---|---|---|---|---|---|---|---|---|---|---|
| Date[1] | DIM[2] | Milked[3] | Lbs.[4] | Date | DIM | Milked | Lbs. | Date | DIM | Milked | Lbs. |
| January | 183 | 49 | 15563 | January | 201 | 50 | 16535 | January | 241 | 55 | 18703 |
| February | 170 | 58 | 15795 | February | 171 | 57 | 16258 | February | 260 | 54 | 18776 |
| March | 173 | 56 | 15725 | March | 155 | 62 | 16310 | March | 251 | 54 | 18516 |
| April | 192 | 53 | 15643 | April | 163 | 60 | 16409 | April | 227 | 55 | 18261 |
| May | 217 | 51 | 15584 | May | 157 | 63 | 16421 | May | 220 | 52 | 18068 |
| June | 229 | 49 | 15467 | June | 165 | 64 | 16574 | | | | |
| July | 244 | 51 | 15503 | July | 161 | 56 | 16849 | | | | |
| August | 280 | 51 | 15841 | August | 182 | 56 | 17080 | | | | |
| N/A | N/A | N/A | N/A | September | 207 | 56 | 17329 | | | | |
| October | 300 | 48 | 16315 | October | 231 | 54 | 17570 | | | | |
| November | 291 | 48 | 16606 | N/A | N/A | N/A | N/A | | | | |
| December | 264 | 45 | 16787 | December | 229 | 53 | 18047 | | | | |

[1]Date: year 1, year before vaccination; year 2, year during which cows were vaccinated; year 3, year after cows were vaccinated.
[2]DIM, days in milk.
[3]Milked, number of cows milked during the time period.
[4]Lbs., total pounds of milk produced during the time period.

Figure 5:
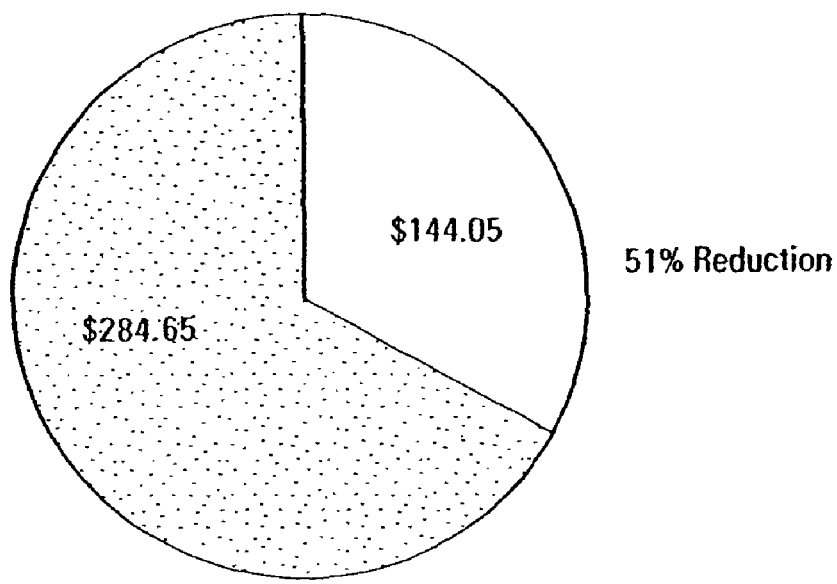
FIG. 5. The average monthly cost in antibiotic usage before and after vaccination. 51% reduction refers to the reduction of the costs of antibiotics after vaccination.

FIG. 5 shows the average monthly cost in antibiotic usage calculated 12 months after the first vaccination compared to 12 months before vaccination. The average monthly cost in antibiotic usage before vaccination or during the course of Salmonellosis was $284.65 compared to $144.05 after vaccination. This was a 51% reduction in the cost of antibiotics.

At the onset of the first isolation of *Salmonella bredeney* (January, year 1) and clinical diagnosis from this herd, approximately 21 adult cows and 36 calves died of clinical Salmonellosis. This mortality occurred despite vaccinating the herd three separate times over a one year period, using a commercial whole cell bacterin of *Salmonella dublin* and *Salmonella typhimurium*. The herd was up to date in all, routine viral and bacterial vaccines. After the first vaccination with the composition described in Example 3, mortality and morbidity virtually ceased. Six months after the first vaccination only three calves died within this time period. None of the calves that died within this time period were diagnosed with *Salmonella*. There has been no mortality in any of the non-lactating (dry), lactating cattle and/or calves in this herd, since the first *Salmonella* vaccination. From this data it would appear the vaccine induced a high degree of humoral immunity against field challenge as well as providing passive immunity to newborn calves. It was also apparent in this field study that as the serological response to vaccination increased, the shedding prevalence of *Salmonella* decreased. It is interesting to note that the antibody titer continued to rise 25 weeks after the third vaccination. This continued rise in titer could be due to clinical field challenge by *Salmonella* or other gram negative bacteria expressing these highly conserved proteins during subclinical infections.

Vaccination improved the overall health and performance status of the herd as observed by the decrease in mortality, decreased somatic cell counts and the increase in milk production. Calf health also improved, as calves were more active at birth, consumed colostrum aggressively and did not develop any significant diarrhea symptoms. In addition, there was an observed decrease in clinical metritis in the fresh cows that were brought back into production after calving. These cows were vaccinated at dry off and boosted prior to calving. Vaccination appeared to alleviate the incidence of clinical metritis during the post-calving period. This was initially observed while taking fecal samples for the isolation of *Salmonella* in that rectal palpation of the uterus could be done at the same time. The incidence of metritis dramatically decreased after vaccination as compared to previous years.

The vaccine composition proved to be highly tissue compatible. None of the vaccinated cows showed any adverse tissue reaction at the site of injection or any physical signs of stress such as, depression, lethargy, loss of milk production, etc. The compatibility of the vaccine composition is likely due to its purity and lack of contaminating lipopolysaccharides (LPS). LPS has been shown to be responsible for much of the tissue reactions in conventional vaccines, such as whole cell bacterins. The concentration of LPS in the stock antigen of Example 3 was found to be negative as examined by the *Limulus Amebocyte* Lysate Assay (SIGMA, Chemical Company, St Louis Mo.).

Example 8

The Effect of Vaccinating Fresh Cows and Cows in First Lactation

A subunit vaccine consisting SRPs and porins derived from *Salmonella* dublin (strain designation MS010207) and *Salmonella typhimurium* (strain designation MS010427) were administered to two groups of lactating cows in a controlled field study within a large expansion dairy. The dairy consisted of 500 cows separated into five large freestall corrals (100 cows/corral) based on days in milk or period of lactation. Two groups of cows were chosen for the study; fresh cows (30-90 days postpartum) and high-producing heifers (cows in first lactation). Cows received two subcutaneous vaccinations 28 days apart. The experimental trial examined the safety of the immunizing composition based on the tissue reactivity of the injected material at the site of injection, the effect vaccination had on milk production, the prevalence of *Salmonella* and somatic cell counts between vaccinated and non-vaccinated cows. Data was collected on performance and physiological status from individual cows using an integrated electronic cow identification system.

Preparation of an Immunizing Composition Derived from *Salmonella dublin* and *Salmonella typhimurium*

The immunizing composition was prepared as described in Example 3 with the following modifications. Three high molecular weight SRPs at approximately the 89 kDa, 84 kDa and 72 kDa and porins in the range of 38-39 kDa were harvested from each of the two isolates. The lower molecular weight IRPs (37 kDa, 32 kDa and 29 kDa) that *S. bredeney* expressed under iron restriction of Example 3 were poorly expressed in *S. dublin* and/or *S. typhimurium* and were not present in the final stock antigen as examined on a 10% SDS-Page gel. Nevertheless, the upper banding profile (89 kDa, 84 kDa and 72 kDa) of these two isolates were identical to *S. bredeney* of Example 3. The immunizing composition consisted of equal concentration of SRPs from *S. dublin* and *S. typhimurium* so as to provide a total dose of 1000 µg, 500 µg from each isolate. The antigen solution was emulsified into EMUSIGEN (22.5% vol/vol) as previously described in Example 3.

Pre-Vaccination

Thirty days before the first vaccination the herd-exposure status to *Salmonella* was determined. Fecal samples were collected from each individual cow as described in Example 6. The total number of samples collected was 144 (60 Fresh cows and 84 Heifers). *Salmonella* was recovered from 50% of the Fresh cows and 27% from the cows in first lactation. Three serotypes were found; *S. anatum, S. uganda* and *S. meleagridis; S. dublin* and *S. typhimurium* were not detected. The SRP and porin profiles of these isolates were found to be identical to the banding profiles of *S. dublin, S. typhimurium* and *S. bredeney*. Because of the wide spread incidence of *S. dublin* and *S. typhimurium* in the bovine species and the conserved nature of these proteins it was decided to use these antigens in the vaccine composition to give further clarification of the cross-protective nature of these proteins.

Immunization of Fresh Cows and Cows in First Lactation

Fifty percent of the cows in first lactation (42 out of 84) and 50% of the fresh cows (30 out of 60) were vaccinated. The remaining cows in each group remained as non-vaccinated controls. Briefly, cows from each group were randomly placed in a large holding stanchion. Every other cow was given a 2 ml intramuscular injection of the vaccine. In addition, fecal samples were taken from all cows in each group by rectal extraction at the time of the first vaccination. All suspect isolations were serotyped as described in Example 6. The somatic cell count and milk production for each cow was acquired prior to the first vaccination to establish a historical performance trend. The production of milk from individual cows was monitored daily as well as general health and adverse reaction to vaccination. The somatic cell counts were monitored monthly by the DHIA. The vaccinated cows were given a second vaccination (Booster) four weeks after the first vaccination. The vaccinated and non-vaccinated test cows within the herd were identified by ear tags and milk production was monitored by an electronic cow identification system using a transponder, hung on a strap around the cows neck. The overall performance of the vaccinated and non-vaccinated cows was monitored throughout the experimental study.

Results

The injection sites of vaccinated cows were examined 14 days after the first and second vaccination. None of the vaccinated cows showed any adverse tissue reaction to the vaccine at the site of injection. There was no visible swelling or defined nodule in any of the cows examined. In addition, daily observations of these cows showed no visible changes in behavior and/or activity.

Fecal samples taken from both groups the day of the first vaccination revealed a significant decline in the shedding prevalence of *Salmonella* as compared to samples taken 30 days before vaccination. The isolation rate in the fresh cow group declined to 27% while the cows in first lactation had dropped to 8%. In fact, the isolation rate of *Salmonella* at the second vaccination showed no difference between groups. Only five isolates of *Salmonella* were cultured between groups, three from the fresh cow group and 2 from the first lactation cow group. There was no difference in the shedding prevalence of *Salmonella* between the vaccinated and non-vaccinated cows from either group.

Figure 6:
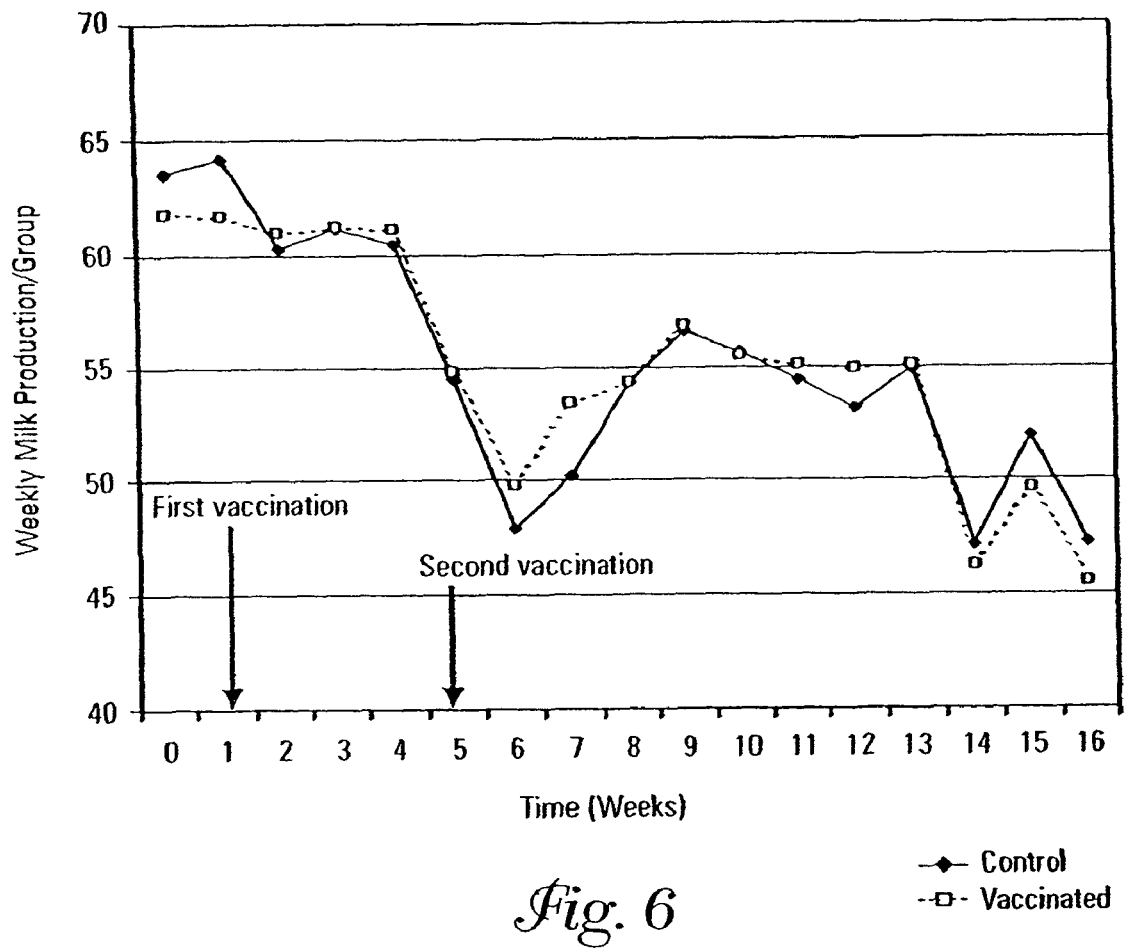
FIG. 6. The average weekly milk production between vaccinated and non-vaccinated cows in first lactation. Weekly Milk Production/Group, weekly production of milk (in pounds) for the control group and the vaccinated cows.
Figure 7:
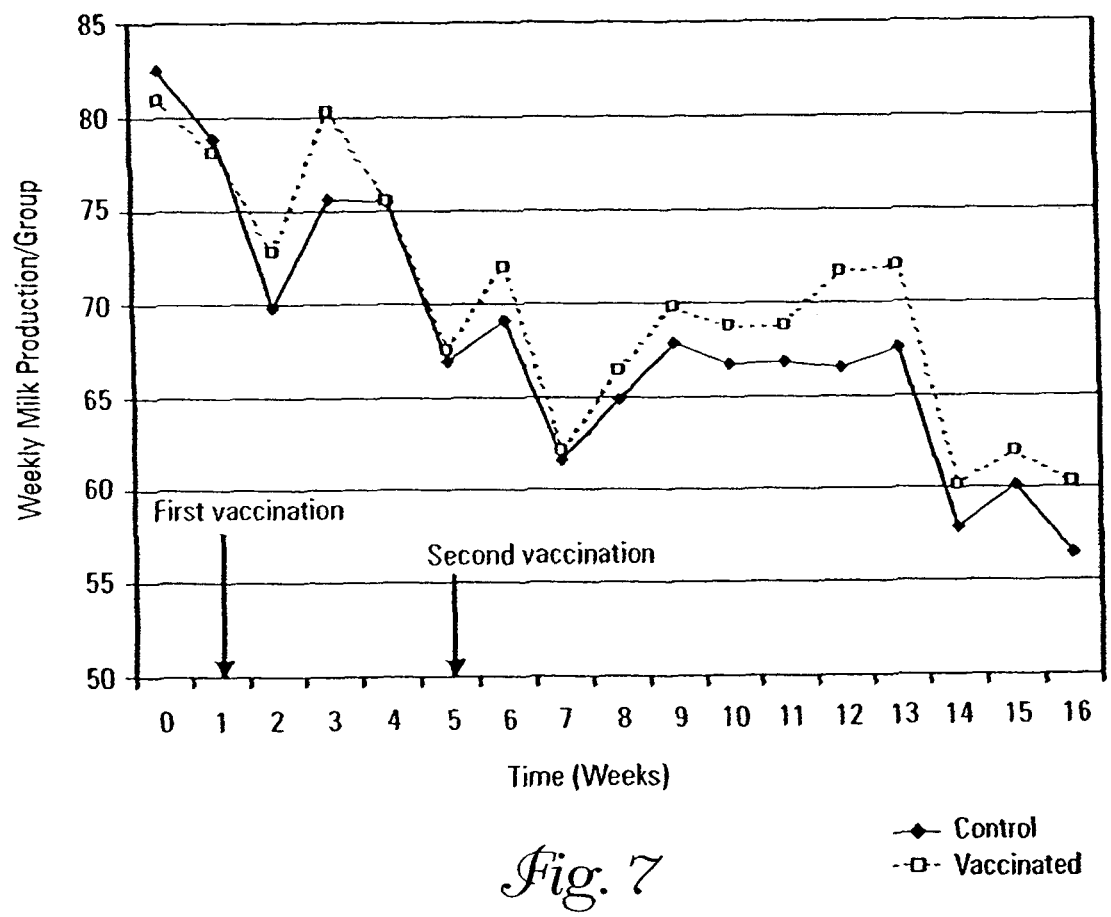
FIG. 7. The average weekly milk production between vaccinated and non-vaccinated fresh cows. Weekly Milk Production/Group, weekly production of milk (in pounds) for the control group and the vaccinated cows.

The yield of milk per cow was monitored daily in both groups. FIG. 6 shows the weekly average milk production between the vaccinated and non-vaccinated cows in first lactation. There was no statistical difference in the yield of milk from the first vaccination (week 1) to the second vaccination (week 2) when compared to the non-vaccinated cows (P=0.435) and from the second vaccination (week 5) through the $16^{th}$ week of production (P=0.07) as graphically depicted in FIG. 6. However, in the fresh cow group, the production of milk statistically increased in the vaccinated cows after each vaccination as compared to the non-vaccinated group (FIG. 7). The degree of significance from the first vaccination to the second vaccination was P=0.006 and dramatically increased from the second vaccination to the $16^{th}$ week of production (P=0.000000067). Sixteen weeks after the first vaccination the average pounds of milk produced per cow in the vaccinated group was 60.3 pounds compared to 56.4 pounds in the non-vaccinated controls. This was a 6.5% increase in milk production over the control group OT 3.9 pounds/cow advantage.

Figure 8:
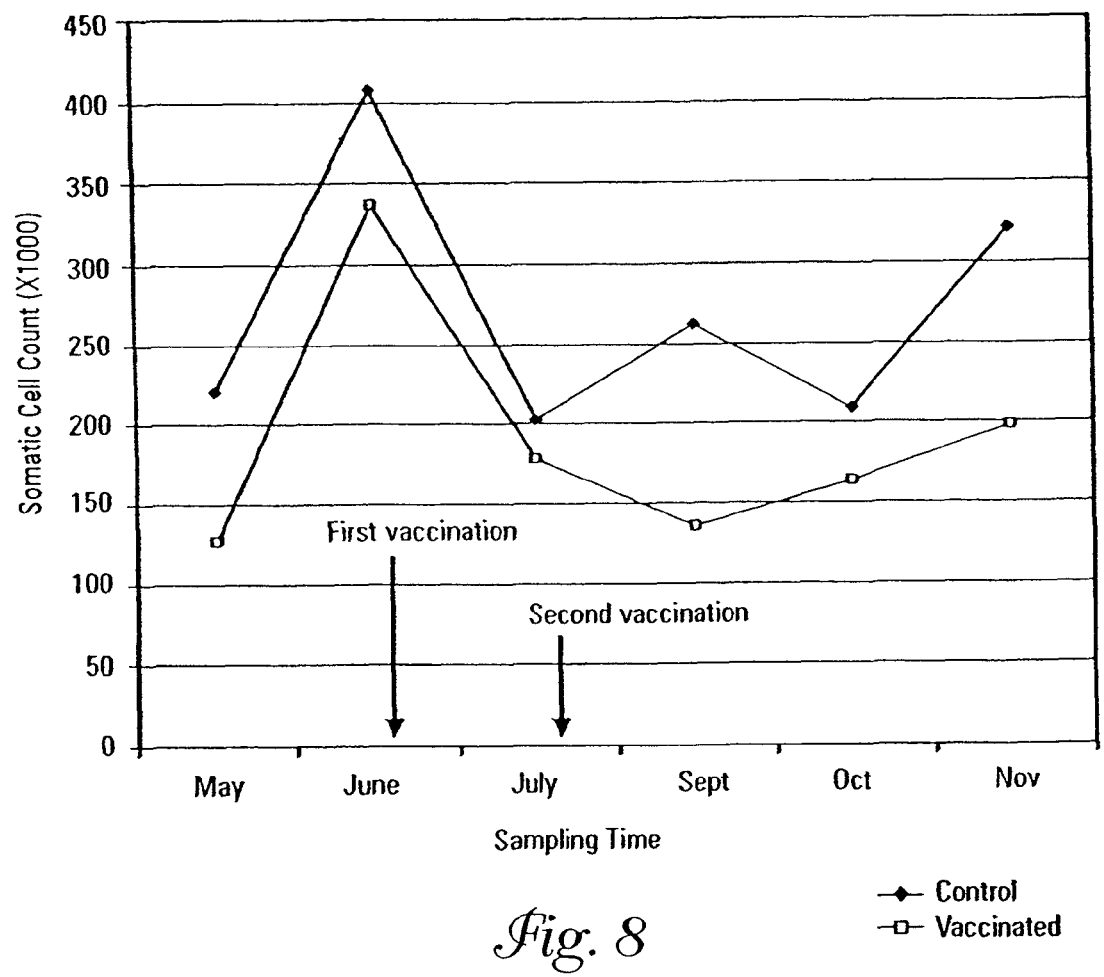
FIG. 8. The monthly average somatic cell count (DHIA) between vaccinated and non-vaccinated cows in first lactation.
Figure 9:
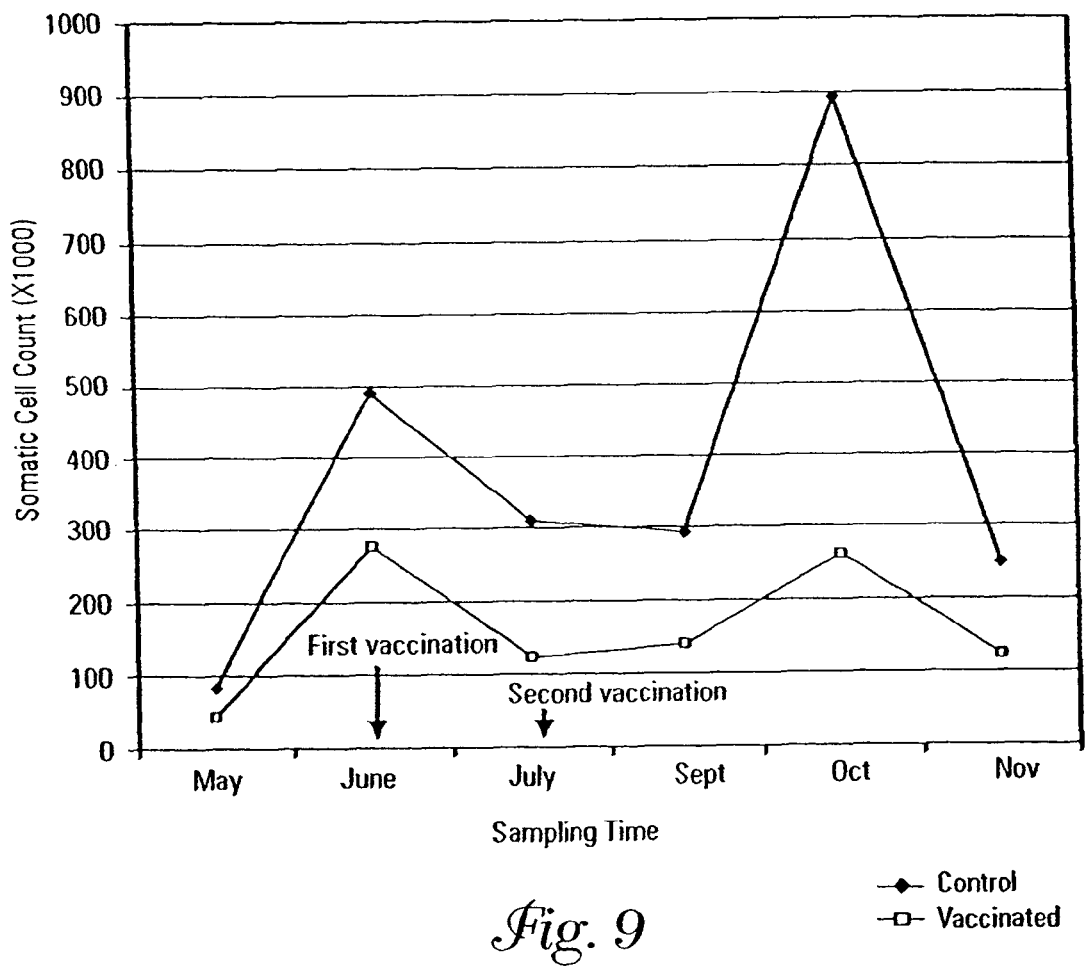
FIG. 9. The monthly average somatic cell count (DHIA) between vaccinated and non-vaccinated fresh cows.

The somatic cells counts were also positively effected through vaccination in both the fresh cows and cows in first lactation. FIG. 8 shows the monthly average (DHIA) somatic cell counts between the vaccinated and non-vaccinated cows in first lactation, beginning from the first vaccination through 16 weeks of production. The data shows that the vaccinated group had a 30.0% difference in the average somatic cell count with a degree of significance of P=0.036 as compared to the non-vaccinated control group. This reduction in somatic cell count was more dramatically pronounced in the vaccinated fresh cows as illustrated in FIG. 9. The data shows that the level of somatic cells decreased by 58.8% (P=0.02) in the vaccinated cows as compared to the non-vaccinated group.

The difference in performance between the fresh cows and in first lactation could be due to the difference in the health status of the cow. Typically fresh cows are under a higher degree of stress due to their physiological status then other cows in production, predisposing them to a greater disease challenge. Stress can often exasperate the likelihood of a diseased condition that may effect the overall health and performance of the animal. It is interesting to note there was no statistical difference in milk production between the vaccinated and non-vaccinated cows in first lactation, in contrast to the vaccinated fresh cows. It would appear that the vaccine had a positive effect on the health status of the vaccinated fresh cows, as seen by the enhanced milk production. This enhanced performance did not appear to be related to a clinical disease caused by *Salmonella* since the isolation rate naturally declined and there was no difference in the prevalence between vaccinated and non-vaccinated cows. In addition, the vaccine composition contained the immunogens derived from *Salmonella dublin* and *Salmonella typhimurium* and not from the isolates found within the herd. Because of the conserved nature of these proteins among gram negative and gram positive bacteria it is highly likely that the vaccine induced a degree of cross-protection against other bacteria expressing these proteins, allowing the animal to perform better.

Example 9

Immunization of feed lot steers for the control of Salmonella, Trial-1

A commercial feed lot having a history of Salmonellosis was used in a controlled field study to evaluate the efficacy of an immunizing composition consisting of SRPs and porins derived from *Salmonella dublin*. The experimental trial examined the safety of the immunizing composition based on the tissue reactivity of the injected material at the site of injection, the serological response to vaccination, and the shedding prevalence of *Salmonella*.

The feed lot consisted of 500 Holstein steers separated into separate grow out facilities based on the age and weight of the steers. The experimental trial was initiated in starter calves (N=150) with an average weight of approximately 150 pounds. The steers were randomly distributed into 10 separate pens (1-10) so that each pen contained 15 steers. Ear tags individually identified steers in each pen. The exposure status to *Salmonella* was determined prior to the first vaccination. Individual fecal samples were taken from all steers to establish a shedding prevalence of *Salmonella*. Samples were processed as previously described in Example 6. *Salmonella* was recovered from 56% of the 150 samples taken. Three different serotypes were identified; *S. dublin, S. uganda* and *S. muenster. Salmonella dublin* was the predominant serotype, and was found within the herd at 67%.

The *Salmonella* positive steers were identified from each pen and distributed among four pens (P3, P4, P5, and P6) so that each pen contained the same number of positive and negative steers. Thus, each pen contained 8 *Salmonella* positive steers and 7 *Salmonella* negative steers so that 53.3% of each pen was *Salmonella* positive.

The immunizing compositions was prepared from the SRPs of S. dublin having molecular weights of 89 kDa, 84 kDa, 72 kDa and porins having molecular weights of 38-39 kDa. The target proteins were emulsified into EMULSIGEN (22.5% vol/vol) to provide a total protein dose of a 1000 µg in a 2 ml injectable volume as previously described.

Steers in pens 3 and 5 received two intramuscular vaccinations 28 days apart. Steers in pens 4 and 6 remained as non-vaccinated controls. Blood was taken from 12 steers per pen at day 0 (First vaccination) and again at 2, 4, and 6 weeks post to monitor the serological response to vaccination. Individual fecal samples were collected from each steer as described in Example 6 on the day of the first vaccination and again at 2 and 6 weeks.

Figure 10:
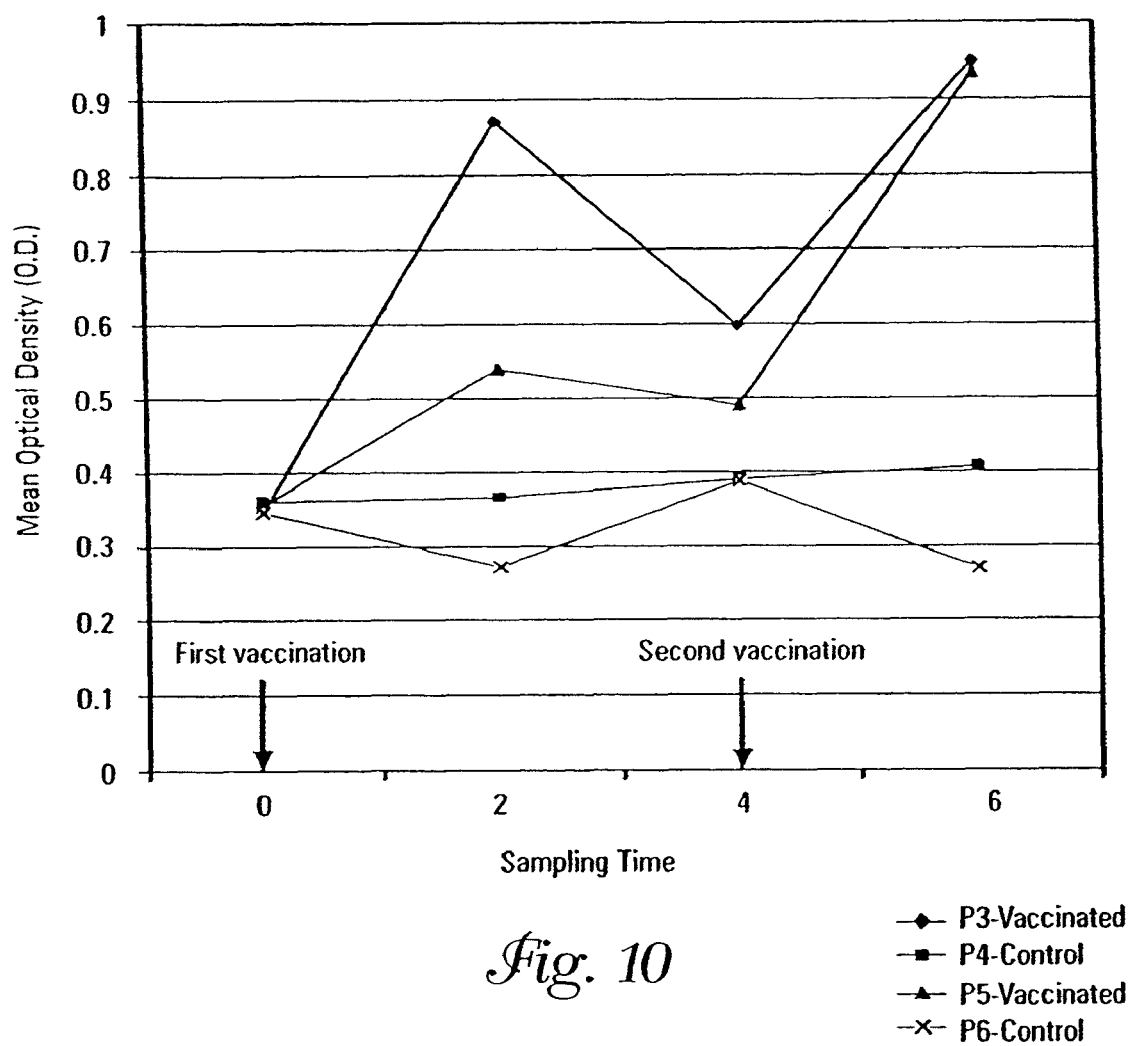
FIG. 10. The serological response of vaccinated steers compared to non-vaccinated controls. Mean optical density (O.D.), 405 nm; P3-Vaccinated and P5-Vaccinated, vaccinated steers in pens 3 and 5, respectively; P4-Control and P6-Control, non-vaccinated steers in pens 4 and 6, respectively; Sampling time, weeks after first vaccination.

The injection sites of each vaccinated steer were examined 14 days after the first and second vaccination. None of the vaccinated steers showed any adverse tissue reaction at the site of injection. In addition, daily observations of these steers showed no visible changes in behavior and/or activity as compared to the non-vaccinated groups. FIG. 10 shows the serological response of vaccinated steers compared to non-vaccinated controls as evaluated by ELISA of Example 7. The vaccine induced elevated antibody titers to SRPs after each vaccination. There was a rise in titer after the first vaccination that declined two weeks after but continued to rise after the second vaccination, clearly demonstrating that a secondary response was induced.

Table 5 shows the shedding prevalence of *Salmonella* between vaccinated and non-vaccinated pens. Fecal samples taken from individual steers on the day of the first vaccination (week 0) revealed a significant decline in the shedding prevalence of *Salmonella* in all test groups as compared to samples taken before vaccination (Table 5). The decline in the shedding prevalence continued through the duration of the sampling period in all test groups. However, the shedding prevalence 14 days after the last vaccination indicated a difference between the vaccinated group as compared to the non-vaccinated controls. There was a higher percentage of *Salmonella* positive steers (29%) in Pen 6 as compared to the vaccinated pens showing only 6.7%.

TABLE 5

The Shedding Prevalence of *Salmonella* Between Vaccinated and Non-vaccinated Pens

| Sampling time | Pen 3- Vaccinated | Pen 4 Control | Pen 5 Vaccinated | Pen 6 Control |
|---|---|---|---|---|
| Pre-vaccination | 53.3% | 53.3% | 53.3% | 53.3% |
| 0 | 33% | 40% | 47% | 43% |
| 2 weeks | 27% | 13% | 13% | 36% |
| 6 weeks | 6.7% | 13% | 6.7% | 29% |

Example 10

Immunization of Feed Lot Steers for the Control of Salmonella Trial-2

The commercial feed lot of Example 9 was used in a controlled field study to provide further data on the efficacy of an immunizing composition consisting of SRPs and porins derived from *Salmonella dublin* and *Salmonella typhimurium*. The experimental trial examined the safety of the immunizing composition based on the tissue reactivity of the injected material at the site of injection, the serological response to vaccination, and the shedding prevalence of *Salmonella*.

At the end of the experiment of Example 9 the facility was cleaned, sanitized and disinfected and allowed to sit empty for 2 weeks prior to the arrival of a new group of steers. Environmental samples (N=2) were taken from each pen to ascertain the incidence of *Salmonella*. Samples were cultured as previously described in Example 6. All environmental samples were found negative for *Salmonella*. One hundred fifty (N=150) 4 month old Holstein steers with and average weight of 300 pounds were transported by truck from Idaho. Upon arrival, steers were unloaded, ear tagged for identification and randomly distributed among 10 separate pens (1-10) so that each pen contained 15 steers. One week after arrival the exposure status to *Salmonella* was determined prior to the first vaccination. Individual fecal samples were taken from all steers to establish a shedding prevalence of *Salmonella*. Samples were processed as previously described in Example 6. All of the 150 samples taken were found negative for *Salmonella*. Based on this information a vaccine composition was prepared from two *Salmonella* isolates (*S. dublin* (strain designation MS010207) and *S. typhimurium* (strain designation MS010427)).

The immunizing compositions was prepared from the SRPs of *S. dublin* and *S. typhimurium* having molecular weights within a range of 89 kDa, 84 kDa, 72 kDa and porins having molecular weights within a range of 38-39 kDa. The proteins (500 µg from each isolate) were absorbed onto aluminum hydroxide (25% vol/vol) to provide a total protein dose of a 1000 µg in a 2 ml injectable volume.

As before, steers in pens 3 and 5 received two intramuscular vaccinations 28 days apart. Steers in pens 4 and 6 remained as non-vaccinated controls. Blood was taken from 12 steers per pen at day 0 (First vaccination) and again at 2, 4, and 6 weeks post to monitor the serological response to vaccination. Individual fecal samples were collected from each steer as described in Example 6 on the day of the first vaccination and again at 2 and 6 weeks.

The injection sites of each vaccinated steer, as before, were examined 14 days after the first and second vaccination None of the vaccinated steers showed any adverse tissue reaction at the site of injection using aluminum hydroxide as the adjuvant. In addition, daily observations of these steers showed no visible changes in behavior and/or activity as compared to the non-vaccinated groups. The serological response to the vaccine was determined as described herein and compared to the non-vaccinated controls. The vaccine induced elevated antibody titers to SRPs after each vaccination that was comparable to the composition of Example 9. There was a rise in titer after the first vaccination that declined for two weeks after but continued to rise after the second vaccination.

Fecal samples were taken from all steers at the time of first vaccination and again at 2 and 6 weeks after vaccination. *Salmonella* was not isolated from any of the samples taken during the sampling period. In addition, environmental samples (N=2) taken from each pen at the 6 week period were negative for *Salmonella*.

Nine weeks after the first vaccination steers in both the control and vaccinated pens were individually weighed. The average weight of steers in the control pens were 730.5 lbs (Pen-4) and 745.6 lbs (Pen-6) (Table 6) with an average weight of both pens at 738.0 lbs. In contrast, the average weight of vaccinated steers were 767.7 pounds (Pen-3) and 761.8 lbs (Pen-5) (Table 6) with a combined average weight of 764.8 lbs. There was a 26.7 pound advantage in the vaccinated steers as compared to the steers in the non-vaccinated groups with a degree of significance of P=0.018. This enhanced weight performance did not appear to be related to a clinical disease caused by *Salmonella* since the organism was not detected in any of the steers examined. It is believed that the conserved nature of these proteins in the vaccine composition induced a degree of cross-protection against other bacteria expressing these proteins, thus lessening subclinical diseases, allowing the animal to perform better as seen in the difference in weight between the two groups.

TABLE 6

The Comparison of Individual Weights Between Vaccinated and Non-Vaccinated steers 9 weeks after the first vaccination

| Pen-3 Vaccinated Weight in pounds | Pen-4 Control Weight in Pounds | Pen-5 Vaccinated Weight in Pounds | Pen-6 Control Weight in Pounds |
|---|---|---|---|
| 742 | 682 | 816 | 724 |
| 889 | 723 | 717 | 812 |
| 750 | 595 | 716 | 756 |
| 712 | 705 | 811 | 735 |
| 844 | 737 | 801 | 779 |
| 794 | 726 | 740 | 717 |
| 769 | 780 | 796 | 744 |
| 755 | 752 | 758 | 670 |
| 698 | 811 | 785 | 749 |
| 772 | 706 | 785 | 775 |
| 746 | 778 | 743 | 729 |
| 744 | 725 | 764 | 819 |
| 697 | 741 | 719 | 712 |
| 809 | 744 | 775 | 688 |
| 795 | 752 | 701 | 775 |
| Mean = 767 | Mean = 730.5 | Mean = 761.8 | Mean = 745.6 |
| SD[1] = 52.7 | SD = 49.7 | SD = 37.6 | SD = 41.9 |
| CV = 6.9 | CV = 6.8 | CV = 4.9 | CV = 5.7 |

[1]SD, standard variation.
[2]CV, coefficient of variation.

Example 11

Purification of Siderophore Receptor Proteins of *Staphylococcus aureus* of Human and Avian Origin Two field isolates of *Staphylococcus aureus* and three additional isolates obtained from the American Type Culture Collection ATCC (isolates 8432, 11371, and 19636) were evaluated for the expression of siderophore receptor proteins. Field isolates originating from turkeys were isolated from the hock joints of diseased birds. ATCC isolate 8432 was also of avian origin, while isolates 11371 and 19636 were of human origin. All bacteria were grown in Brain heart infusion broth (BHI, DIFCO) as iron-deplete and/or iron-replete media. The iron-deplete media was iron-restricted chemically using 2'2'-dipyridyl at 175 mM, whereas the iron-replete media contained 200 µM ferric chloride. The bacteria were grown in 10 ml of BHI for 8 hours at 37° C. while stirring at 400 rpm. At 8 hours of incubation, 1.0 ml of culture was removed and washed in 10 volumes sterile physiological saline by centrifugation (10,000×g) for 10 minutes. The pellet was resuspended in 100 microliters (up of saline containing 1 mg lysostaphin (SIGMA, St. Louis, Mo.) was added, and the suspension was then incubated at 37° C. for 2 hours. The bacterial suspension was centrifuged at 12,000×g for 1 minute. The supernatant was collected and centrifuged again at 20,000×g for 40 minutes. The bacterial pellet was resuspended in 100 µl tris-buffered saline (TBS) at pH 7.4. The resuspended bacterial pellets from the different isolates were resolved by 12% SDS-PAGE and transferred onto nitrocellulose membranes and tested for cross-reactivity with sera to SRPs of gram negative bacteria. Absorbed rabbit polyclonal hyper-immune sera prepared against purified SRPs from *E. coli* and/or *S. typhimurium* were used as probes in the immunoblot of the *S. aureus* SRPs.

The SDS-PAGE patterns of the outer membrane protein extracts of the *Staphylococcus aureus* isolates showed different patterns of SRP expression between the field isolates and the ATCC isolates. The field isolates of turkey origin grown under conditions of iron restriction showed four proteins with molecular weights between 66-90 kDa (specifically, 90 kDa, 84 kDa, 72 kDa and 66 kDa) and also at about 36 kDa, 32 kDa and 22 kDa regions. The ATCC isolates showed only a single SRP at the 40-55 kDa range (42 kDa) and at the 36 kDa range. None of the ATCC isolates showed an SRP at 66-90 kDa region, including isolate 8432 of avian origin.

Western blot analysis of the isolated SRPs of the *S. aureus* field isolates was conducted by probing with sera raised to the SRPs of *Salmonella* (89 kDa, 84 kDa and 72 kDa) and/or *E. coli* (89 kDa, 84 kDa, 78 kDa, and 72 kDa). The sera reacted strongly with the proteins in the 66-90 kDa range but not with the lower molecular weight proteins (i.e., 36 kDa, 32 kDa and 22 kDa). The *Salmonella* sera also reacted with a protein in the 31 kDa range that appeared to be similar to the 31 kDa protein of the transmembrane proteins of gram negative bacteria.

This data indicates that *S. aureus* expressed SRPs that are within a similar molecular weight range as gram negative bacteria, and that antibodies raised against SRPs from gram negative bacteria cross-react between at least two different families of bacteria. This composition is used to vaccinate animals as described herein, and the ability of the composition to protect animals from homologous and heterologous challenge is determined, as well as the ability of the composition to enhance performance characteristics of the animal.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

What is claimed is:

1. A method for inducing the production of an antibody that specifically binds at least one SRP or at least one porin in an animal, the method comprising administering to an animal an effective amount of a composition comprising:
   at least two siderophore receptor polypeptides (SRPs) isolated from a gram negative microbe;
   at least two porins isolated from the gram negative microbe; lipopolysaccharide (LPS) at a concentration of no greater than about 10.0 EU/ml; and
   a pharmaceutically acceptable carrier, wherein the composition induces in the animal antibody that specifically binds at least one SRP or at least one porin.

2. The method of claim 1 wherein the gram negative microbe is an enteropathogen.

3. The method of claim 1 wherein the gram negative microbe is a member of the family Enterobacteriaceae, family Vibrionaceae, family Pasteurellaceae, or family Pseudomonadaceae.

4. The method of claim 1 wherein the gram negative microbe is a member of the tribe Escherichieae or Salmonelleae.

5. The method of claim 1 wherein the gram negative microbe is *Salmonella* spp. *Escherichia coli, Actinobacillus* spp., *Haemophilus* spp., or *Campylobacter* spp.

6. The method of claim 1 wherein the at least two SRPs have molecular weights of between about 60 kDa and about 100 kDa as determined by separation by sodium dodecyl sulfate-polyacrylamide gel electrophoresis.

7. The method of claim 1 wherein the animal is an avian, a bovine, a caprine, a porcine, an ovine, a Bison, a companion animal, or a member of the family Ceridae[, or a human].

8. The method of claim 1 wherein the animal is a bovine, and wherein the method further includes reducing somatic cell count, increasing milk production, decreasing fecal shedding, treating intestinal colonization, or increasing weight in the bovine.

9. The method of claim 1 wherein the gram negative microbe is a first gram negative microbe, wherein the antibody specifically binds an SRP present on the surface of a second gram negative microbe.

10. The method of claim 9 wherein the second gram negative microbe is an enteropathogen.

11. The method of claim 9 wherein the second gram negative microbe is a member of the family Enterobacteriaceae, family Vibrionaceae, family Pasteurellaceae, or family Pseudomonadaceae.

12. The method of claim 9 wherein the first and second gram negative microbes are different species.

13. The method of claim 9 wherein the first and second gram negative microbes are different genera.

14. The method of claim 9 wherein the second gram negative microbe is a member of the tribe Escherichieae or Salmonelleae.

15. The method of claim 1 wherein the animal has or is at risk of having a gram negative infection.

16. The method of claim 1 wherein the method further comprises collecting the antibody.

17. The method of claim 1 wherein the method further comprises isolating the antibody.

18. The method of claim 17 wherein the collecting comprises collecting serum, plasma, blood, or colostrum.

19. The method of claim 16 wherein the method further comprises administering the collected antibody to a second animal.

20. The method of claim 19 wherein the administering the collected antibody comprises administration of colostrum to the second animal.

21. The method of claim 1 wherein the at least two porins have molecular weights of between about 30 kDa and about 43 kDa as determined by separation by sodium dodecyl sulfate-polyacrylamide gel electrophoresis.

22. The method of claim 7 wherein the companion animal is a horse.

23. A method for inducing the production of an antibody that specifically binds at least one SRP or at least one porin in an animal, the method comprising administering to an animal an effective amount of a composition comprising:
   at least two siderophore receptor polypeptides (SRPs) isolated from a gram negative microbe;
   at least two porins isolated from the gram negative microbe;
   lipopolysaccharide (LPS) at a concentration of no greater than the concentration of LPS in a reference composition comprising: the at least two siderophore receptor polypeptides isolated from the gram negative microbe and lipopolysaccharide; wherein the reference composition is produced by a process comprising:
      providing the gram negative microbe;
      disrupting the gram negative microbe in a buffer;
      solubilizing the disrupted gram negative microbe for greater than about 24 hours in a solution comprising sarcosine to result in solubilized and insoluble cellular material, wherein a ratio of the sarcosine to gram weight of disrupted gram negative microbe is between about 0.8 gram sarcosine per about 4.5 grams of disrupted gram negative microbe and about 1.2 grams sarcosine per about 4.5 grams of disrupted gram negative microbe; and
   isolating molecules of the gram negative microbe, wherein the isolated molecules comprise the at least two SRPs and LPS; and
   a pharmaceutically acceptable carrier, wherein the composition induces in the animal antibody that specifically binds at least one SRP or at least one porin.

24. The method of claim 23 wherein the gram negative microbe is an enteropathogen.

25. The method of claim 23 wherein the gram negative microbe is a member of the family Enterobacteriaceae, family Vibrionaceae, family Pasteurellaceae, or family Pseudomonadaceae.

26. The method of claim 23 wherein the gram negative microbe is a member of the tribe Escherichieae or Salmonelleae.

27. The method of claim 23 wherein the gram negative microbe is *Salmonella* spp. *Escherichia coli, Actinobacillus* spp., *Haemophilus* spp., or *Campylobacter* spp.

28. The method of claim 23 wherein the at least two SRPs have molecular weights of between about 60 kDa and about 100 kDa as determined by separation by sodium dodecyl sulfate-polyacrylamide gel electrophoresis.

29. The method of claim 23 wherein the animal is an avian, a bovine, a caprine, a porcine, an ovine, a Bison, a companion animal, or a member of the family Ceridae[, or a human].

30. The method of claim 29 wherein the companion animal is a horse.

31. The method of claim 23 wherein the animal is a bovine, and wherein the method further includes reducing somatic cell count, increasing milk production, decreasing fecal shedding, treating intestinal colonization, or and increasing weight in the bovine.

32. The method of claim 23 wherein the gram negative microbe is a first gram negative microbe, wherein the antibody specifically binds an SRP present on the surface of a second gram negative microbe.

33. The method of claim 32 wherein the second gram negative microbe is an enteropathogen.

34. The method of claim 32 wherein the second gram negative microbe is a member of the family Enterobacteriaceae, family Vibrionaceae, family Pasteurellaceae, or family Pseudomonadaceae.

35. The method of claim 32 wherein the first and second gram negative microbes are different species.

36. The method of claim 32 wherein the first and second gram negative microbes are different genera.

37. The method of claim 32 wherein the second gram negative microbe is a member of the tribe Escherichieae or Salmonelleae.

38. The method of claim 32 wherein the animal has or is at risk of having a gram negative infection.

39. The method of claim 32 wherein the method further comprises collecting the antibody.

40. The method of claim 39 wherein the method further comprises administering the collected antibody to a second animal.

41. The method of claim 40 wherein the administering the collected antibody comprises administration of colostrum to the second animal.

42. The method of claim 39 wherein the collecting comprises collecting serum, plasma, blood, or colostrum.

43. The method of claim 32 wherein the method further comprises isolating the antibody.

44. The method of claim 41 wherein the at least two porins have molecular weights of between about 30 kDa and about 43 kDa as determined by separation by sodium dodecyl sulfate-polyacrylamide gel electrophoresis.

45. The method of claim 3 wherein the member of the family Enterobacteriaceae is *Shigella* spp., *Proteus* spp., *Klebsiella* spp., *Serratia* spp., or *Yersinia* spp.

46. The method of claim 3 wherein the member of the family Vibrionaceae is *Vibrio cholerae*.

47. The method of claim 3 wherein the member of the family Pasteurellaceae is *Pasturella* spp.

48. The method of claim 47 wherein the *Pasturella* spp, is *Pasturella multocida* or *Pasteurella haemolytica*.

49. The method of claim 3 wherein the member of the family Pseudomonadaceae is *Pseudomonas* spp.

50. The method of claim 49 wherein the *Pseudomonas* spp, is *Pseudomonas aeruginosa*.

51. The method of claim 11 wherein the member of the family Enterobacteriaceae is *Shigella* spp., *Proteus* spp., *Klebsiella* spp., *Serratia* spp., or *Yersinia* spp.

52. The method of claim 11 wherein the member of the family Vibrionaceae is *Vibrio cholerae*.

53. The method of claim 11 wherein the member of the family Pasteurellaceae is *Pasturella* spp.

54. The method of claim 53 wherein the *Pasturella* spp, is *Pasturella multocida* or *Pasteurella haemolytica*.

55. The method of claim 11 wherein the member of the family Pseudomonadaceae is *Pseudomonas* spp.

56. The method of claim 55 wherein the *Pseudomonas* spp, is *Pseudomonas aeruginosa*.

57. The method of claim 25 wherein the member of the family Enterobacteriaceae is *Shigella* spp., *Proteus* spp., *Klebsiella* spp., *Serratia* spp., or *Yersinia* spp.

58. The method of claim 25 wherein the member of the family Vibrionaceae is *Vibrio cholerae*.

59. The method of claim 25 wherein the member of the family Pasteurellaceae is *Pasturella* spp.

60. The method of claim 59 wherein the *Pasturella* spp, is *Pasturella multocida* or *Pasteurella haemolytica*.

61. The method of claim 25 wherein the member of the family Pseudomonadaceae is *Pseudomonas* spp.

62. The method of claim 61 wherein the *Pseudomonas* spp. is *Pseudomonas aeruginosa*.

63. The method of claim 34 wherein the member of the family Enterobacteriaceae is *Shigella* spp., *Proteus* spp., *Klebsiella* spp., *Serratia* spp., or *Yersinia* spp.

64. The method of claim 34 wherein the member of the family Vibrionaceae is *Vibrio cholerae*.

65. The method of claim 34 wherein the member of the family Pasteurellaceae is *Pasturella* spp.

66. The method of claim 65 wherein the *Pasturella* spp, is *Pasturella multocida* or *Pasteurella haemolytica*.

67. The method of claim 34 wherein the member of the family Pseudomonadaceae is *Pseudomonas* spp.

68. The method of claim 67 wherein the *Pseudomonas* spp. is *Pseudomonas aeruginosa*.

69. The method of claim 9 wherein the second gram negative microbe is *Salmonella* spp., *Escherichia coli*, *Actinobacillus* spp., *Haemophilus* spp., or *Campylobacter* spp.

70. The method of claim 32 wherein the second gram negative microbe is *Salmonella* spp., *Escherichia coli*, *Actinobacillus* spp., *Haemophilus* spp., or *Campylobacter* spp.

* * * * *

UNITED STATES PATENT AND TRADEMARK OFFICE
CERTIFICATE OF CORRECTION

PATENT NO. : 7,943,150 B2
APPLICATION NO. : 12/101802
DATED : May 17, 2011
INVENTOR(S) : Daryll A. Emery et al.

Page 1 of 3

It is certified that error appears in the above-identified patent and that said Letters Patent is hereby corrected as shown below:

In the Specification

Column 5, Line 18
Delete "about -20° C." and insert --about -20° C--

Column 5, Line 18
Delete "about -95° C.," and insert --about -95° C,--

Column 5, Line 19
Delete "about -40° C." and insert --about -40° C--

Column 5, Line 19
Delete "about -50° C.," and insert --about -50° C,--

Column 9, Line 39
Delete "animal.uft-edu/short94/rae.htm" and insert --animal.ufl-edu/short94rae.htm)--

Column 12, Line 27
Delete "at -20° C." and insert --at -20° C--

Column 12, Line 50
Delete "about 4° C.," and insert --about 4° C,--

Column 13, Line 38
Delete "instance, -20° C. or" and insert --instance, 20° C or--

Column 20, Line 57 and 60
Delete "37° C." and insert --37° C--

Signed and Sealed this
Twenty-ninth Day of July, 2014

Michelle K. Lee
*Deputy Director of the United States Patent and Trademark Office*

Column 21, Line 25
Delete "to 10° C." and insert --to 10° C--

Column 21, Line 53
Delete "into a -20° C." and insert --into a -20° C--

Column 21, Line 66
Delete "at 4° C.," and insert --at 4° C,--

Column 22, Lines 9 and 51
Delete "4° C." and insert --4° C--

Column 23, Line 21
Delete "4° C." and insert --4° C--

Column 23, Line 46
Delete "into a -20° C." and insert --into a -20° C--

Column 23, Line 60
Delete "25° C." and insert --25° C--

Column 27, Line 16
Delete "at -20° C." and insert --at -20° C--

Column 27, Line 21
Delete "37° C." and insert --37° C--

Column 28, Line 25
Delete "at 4° C.," and insert --4° C,--

Column 28, Lines 28, 36, and 43
Delete "37° C." and insert --37° C--

Column 28, Line 40
Delete "37° C.," and insert --37° C,--

Column 34, Line 26
Delete "OT" and insert --or--

In the Claims

Column 39, Line 45, Claim 7
Delete "Ceridae[, or a human]." and insert --Ceridae.--

CERTIFICATE OF CORRECTION (continued)
U.S. Pat. No. 7,943,150 B2

Column 41, Line 3, Claim 29
Delete "Ceridae[, or a human]." and insert --Ceridae.--

Column 41, Line 9, Claim 31
Delete "or and increasing" and insert --or increasing--